US007569043B2

(12) United States Patent
Fangrow

(10) Patent No.: US 7,569,043 B2
(45) **Date of Patent: *Aug. 4, 2009**

(54) VIAL ADAPTOR FOR REGULATING PRESSURE

(75) Inventor: Thomas F. Fangrow, Mission Viejo, CA (US)

(73) Assignee: ICU Medical, Inc., San Clemente, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/415,969

(22) Filed: May 2, 2006

(65) Prior Publication Data

US 2007/0244462 A1 Oct. 18, 2007

Related U.S. Application Data

(60) Provisional application No. 60/791,364, filed on Apr. 12, 2006.

(51) Int. Cl.
*A61M 5/32* (2006.01)
*A61B 19/00* (2006.01)

(52) U.S. Cl. ........................ 604/411; 604/415; 604/403

(58) Field of Classification Search ................. 604/403, 604/405, 406, 411, 414–416
See application file for complete search history.

(56) References Cited

U.S. PATENT DOCUMENTS

| | | | | |
|---|---|---|---|---|
| 2,074,223 | A | 3/1937 | Horiuchi | |
| 2,409,734 | A | 10/1946 | Bucher | |
| 2,673,013 | A | 3/1954 | Hester | |
| 2,999,500 | A | 9/1961 | Schürer | |
| 3,291,151 | A * | 12/1966 | Loken | 137/565.15 |
| RE26,488 | E | 11/1968 | Bull | |
| 3,584,770 | A | 6/1971 | Taylor | |
| 3,822,700 | A | 7/1974 | Pennington | |

(Continued)

FOREIGN PATENT DOCUMENTS

| | | |
|---|---|---|
| CA | 1037428 | 8/1978 |

(Continued)

OTHER PUBLICATIONS

U.S. Appl. No. 11/414,948, filed May 1, 2006, "Vial Adaptor for Regulating Pressure", listing Thomas F. Fangrow as inventor.

(Continued)

*Primary Examiner*—Leslie R Deak
(74) *Attorney, Agent, or Firm*—Knobbe Martens Olson & Bear LLP

(57) ABSTRACT

In certain embodiments, a vial adaptor for removing liquid contents from a vial comprises a piercing member and a bag. The bag can be contained within the piercing member such that the bag is introduced to the vial when the vial adaptor is coupled with the vial. In some embodiments, the bag expands within the vial as liquid is removed from the vial via the adaptor, thereby regulating pressure within the vial. In other embodiments, a vial comprises a bag for regulating pressure within the vial as liquid is removed therefrom. In some embodiments, a vial adaptor is coupled with the vial in order to remove the liquid. In some embodiments, as the liquid is removed from the vial via the adaptor, the bag expands within the vial, and in other embodiments, the bag contracts within the vial.

13 Claims, 34 Drawing Sheets

U.S. PATENT DOCUMENTS

| | | | | |
|---|---|---|---|---|
| 3,980,082 | A | 9/1976 | Miller | |
| 4,240,433 | A * | 12/1980 | Bordow | 604/540 |
| 4,301,799 | A | 11/1981 | Pope, Jr. et al. | |
| 4,349,035 | A | 9/1982 | Thomas et al. | |
| 4,381,776 | A | 5/1983 | Latham, Jr. | |
| 4,564,054 | A | 1/1986 | Gustavsson | |
| 4,576,211 | A | 3/1986 | Valentini et al. | |
| 4,673,404 | A * | 6/1987 | Gustavsson | 604/411 |
| 4,798,578 | A | 1/1989 | Ranford | |
| 5,176,673 | A | 1/1993 | Marrucchi | |
| 5,478,337 | A | 12/1995 | Okamoto et al. | |
| 5,660,796 | A | 8/1997 | Sheehy | |
| 5,700,245 | A | 12/1997 | Sancoff et al. | |
| 5,725,500 | A | 3/1998 | Micheler | |
| 5,766,147 | A | 6/1998 | Sancoff et al. | |
| 5,772,079 | A | 6/1998 | Gueret | |
| 5,776,125 | A | 7/1998 | Dudar et al. | |
| 6,139,534 | A | 10/2000 | Niedospial, Jr. et al. | |
| 6,715,520 | B2 | 4/2004 | Andréasson et al. | |
| 7,004,926 | B2 * | 2/2006 | Navia et al. | 604/6.14 |
| 7,213,702 | B2 | 5/2007 | Takimoto et al. | |
| 7,354,427 | B2 | 4/2008 | Fangrow | |
| 2003/0070726 | A1 | 4/2003 | Andréasson et al. | |
| 2003/0216695 | A1 | 11/2003 | Yang | |
| 2004/0073169 | A1 | 4/2004 | Amisar et al. | |
| 2004/0073189 | A1 | 4/2004 | Wyatt et al. | |
| 2004/0215147 | A1 | 10/2004 | Wessman et al. | |
| 2006/0149309 | A1 | 7/2006 | Paul et al. | |

FOREIGN PATENT DOCUMENTS

| | | |
|---|---|---|
| EP | 0829250 A2 | 3/1998 |
| WO | WO 84/04672 A | 12/1984 |
| WO | WO 99/27886 | 6/1999 |

OTHER PUBLICATIONS

U.S. Appl. No. 11/415,553, filed May 2, 2006, titled “Vial Adaptor for Regulating Pressure”, listing Thomas F. Fangrow as inventor.

U.S. Appl. No. 11/416,622, filed May 2, 2006, titled “Vial Adaptor for Regulating Pressure”, listing Thomas F. Fangrow as inventor.

U.S. Appl. No. 11/415,652, filed May 2, 2006, titled “Vial Adaptor for Regulating Pressure”, listing Thomas F. Fangrow as inventor.

U.S. Appl. No. 11/415,658, filed May 2, 2006, titled “Vial Adaptor for Regulating Pressure”, listing Thomas F. Fangrow as inventor.

U.S. Appl. No. 11/415,984, filed May 2, 2006, titled “Vial Adaptor for Regulating Pressure”, listing Thomas F. Fangrow as inventor.

U.S. Appl. No. 11/415,978, filed May 2, 2006, titled “Vial Adaptor for Regulating Pressure”, listing Thomas F. Fangrow, Dee E. Warren and Dan Lopez as inventors.

U.S. Appl. No. 11/415,971, filed May 2, 2006, titled “Vial Adaptor for Regulating Pressure”, listing Dee E. Warren and Dan Lopez as inventors.

U.S. Appl. No. 11/415,865, filed May 2, 2006, titled “Vial for Regulating Pressure”, listing Thomas F. Fangrow as inventor.

U.S. Appl. No. 11/472,488, filed Jun. 21, 2006, titled “Vial Adaptor for Regulating Pressure”, listing Thomas F. Fangrow as inventor.

PhaSeal, The PhaSeal® Solution, http://www.phaseal.com/siteUS/page.asp?menuitem=145&right=0, dated Jan. 9, 2006.

PhaSeal, How to Use PhaSeal®, http://www.phaseal.com/siteUS/movies.asp?main=filmsmain&right=filmsright, dated Jul. 25, 2005.

International Search Report dated Jan. 16, 2008, Application No. PCT/US2007/008809, filed Apr. 4, 2007.

Office Action mailed Feb. 1, 2008, U.S. Appl. No. 11/415,622.

Notice of Allowance mailed Jan. 25, 2008, U.S. Appl. No. 11/472,488.

Response to Office Action filed Apr. 22, 2008, U.S. Appl. No. 11/415,971.

Response to Office Action filed Apr. 22, 2008 , U.S. Appl. No. 11/415,865.

Office Action dated May 1, 2008, U.S. Appl. No. 11/414,948.

Office Action dated Apr. 25, 2008, U.S. Appl. No. 11/415,553.

Office Action dated Apr. 25, 2008, U.S. Appl. No. 11/415,652.

Office Action dated Apr. 25, 2008, U.S. Appl. No. 11/415,658.

Office Action dated Apr. 25, 2008, U.S. Appl. No. 11/415,984.

Office Action dated Feb. 27, 2008, U.S. Appl. No. 11/415,978.

Annex to Form PCT/ISA/206 Communication Relating to the Results of the Partial International Search, International Application No. PCT/US2007/008809.

“Protection Safey Products,” IV Sets and Access Devices, Chemo-AIDE Dispensing Pin, Dec. 2002, pp. 7,21, Baxter Healthcare Corporation, Round Lake, IL.

U.S. Appl. No. 11/414,948, filed May 1, 2006.

U.S. Appl. No. 11/415,553, filed May 2, 2006.

U.S. Appl. No. 11/415,622, filed May 2, 2006.

U.S. Appl. No. 11/415,652, filed May 2, 2006.

U.S. Appl. No. 11/415,658, filed May 2, 2006.

U.S. Appl. No. 11/415,978, filed May 2, 2006; Office Actions sent Aug. 24, 2007 and Nov. 30, 2007.

U.S. Appl. No. 11/415,984, filed May 2, 2006.

U.S. Appl. No. 11/415,971, filed May 2, 2006; Office Action sent Oct. 22, 2007.

U.S. Appl. No. 11/415,865, filed May 2, 2006, Office Action sent Oct. 22, 2007.

* cited by examiner

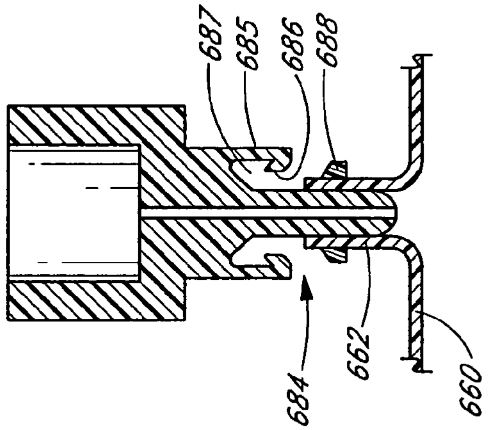
FIG. 15B
FIG. 15A
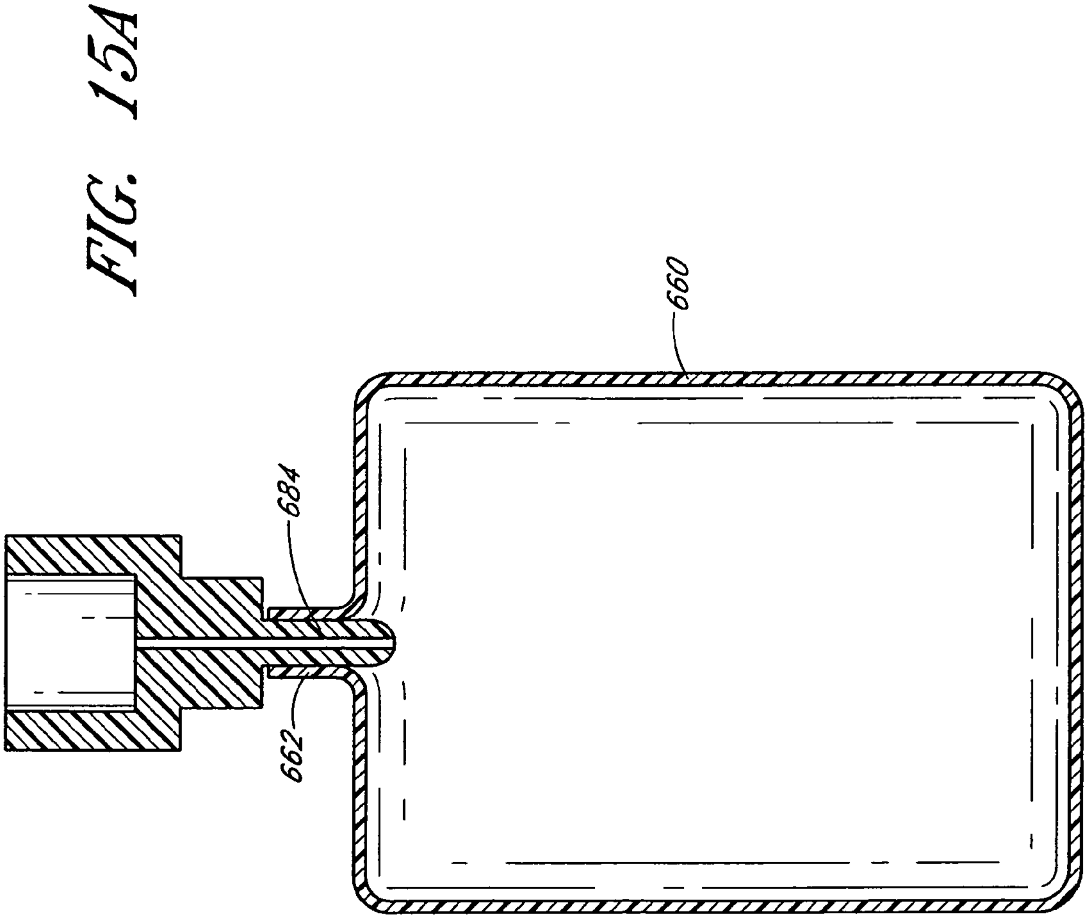

VIAL ADAPTOR FOR REGULATING PRESSURE

RELATED APPLICATIONS

This application claims the benefit under 35 U.S.C. § 119 (e) of U.S. Provisional Application No. 60/791,364, filed Apr. 12, 2006, titled VIAL ADAPTORS AND VIALS FOR REGULATING PRESSURE, the entire contents of which are hereby incorporated by reference herein and made part of this specification.

BACKGROUND OF THE INVENTIONS

1. Field of the Inventions

Certain embodiments disclosed herein relate to novel adaptors for coupling with medicinal vials, and novel medicinal vials, to aid in the removal of contents from the vials and/or to aid in the injection of substances therein, while regulating pressure within such vials.

2. Description of the Related Art

It is a common practice to store medicines or other medically related fluids in vials. In some instances, the medicines or fluids so stored are therapeutic if injected to the bloodstream, but harmful if inhaled or if contacted by exposed skin. Certain known systems for extracting potentially harmful medicines from vials suffer from various drawbacks.

SUMMARY

In certain embodiments, a vial adaptor for removing liquid contents from a vial comprises a piercing member and a bag. The bag can be contained within the piercing member such that the bag is introduced to the vial when the vial adaptor is coupled with the vial. In some embodiments, the bag expands within the vial as liquid is removed from the vial via the adaptor, thereby regulating pressure within the vial.

In other embodiments, a vial comprises a bag for regulating pressure within the vial as liquid is removed therefrom. In some embodiments, a vial adaptor is coupled with the vial in order to remove the liquid. In some embodiments, as the liquid is removed from the vial via the adaptor, the bag expands within the vial, and in other embodiments, the bag contracts within the vial.

BRIEF DESCRIPTION OF THE DRAWINGS

Various embodiments are depicted in the accompanying drawings for illustrative purposes, and should in no way be interpreted as limiting the scope of the inventions. In addition, various features of different disclosed embodiments can be combined to form additional embodiments.

FIG. 15A is a cross-sectional view of a nozzle coupled with a bag.

FIG. 15B is a partial cross-sectional view of a nozzle coupled with a bag.

DETAILED DESCRIPTION OF THE PREFERRED EMBODIMENTS

Figure 1:
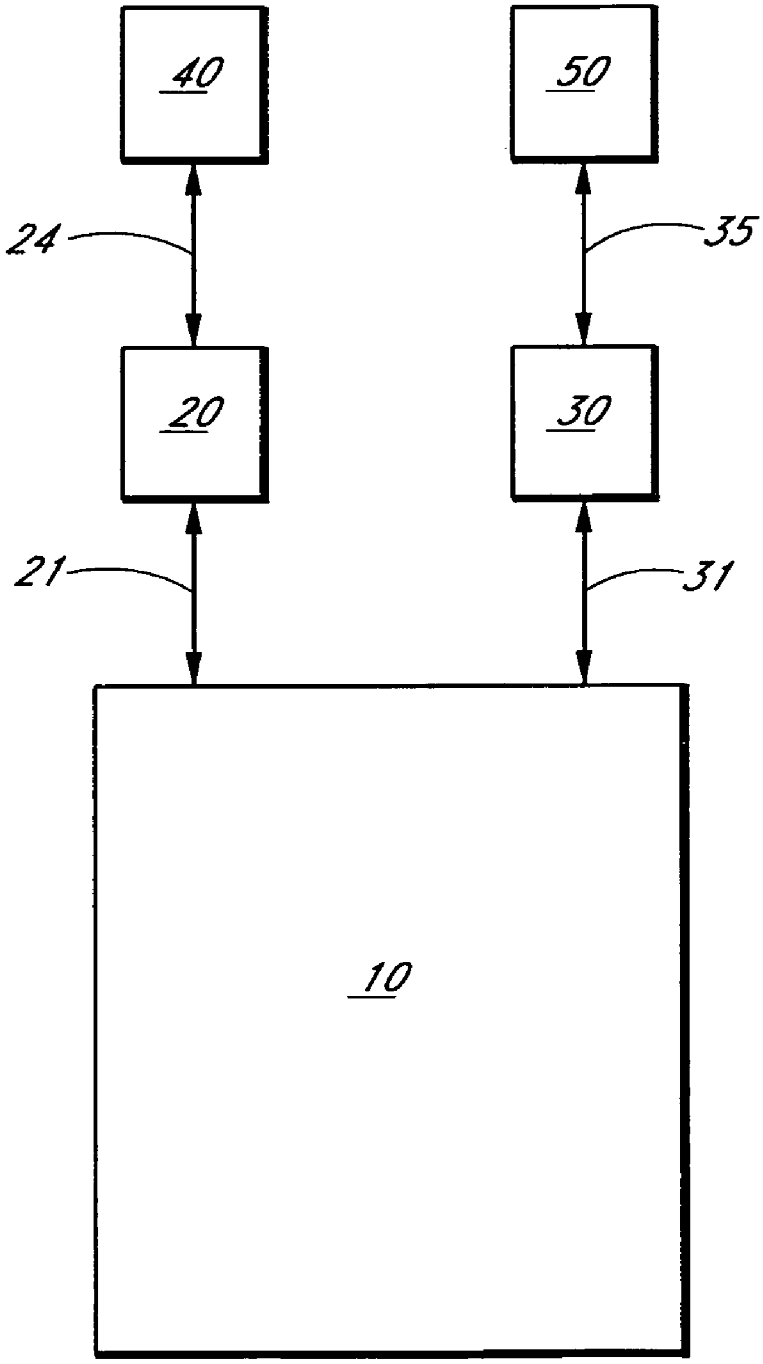
FIG. 1 is a schematic illustration of a system for removing fluid from and/or injecting fluid into a vial.

Numerous medicines and other therapeutic fluids are stored and distributed in medicinal vials of various shapes and sizes. Often, these vials are hermetically sealed to prevent contamination or leaking of the stored fluid. The pressure differences between the interior of the sealed vials and the particular atmospheric pressure in which the fluid is later removed often give rise to various problems.

For instance, introducing the piercing member of a vial adaptor through the septum of a vial can cause the pressure within the vial to rise sharply. This pressure increase can cause fluid to leak from the vial at the interface of the septum and piercing member or at the attachment interface of the adaptor and a medical device, such as a syringe. Also, it can be difficult to withdraw an accurate amount of fluid from a sealed vial using an empty syringe, or other medical instrument, because the fluid may be naturally urged back into the vial once the syringe plunger is released. Furthermore, as the syringe is decoupled from the vial, pressure differences can often cause a small amount of fluid to spurt from either the syringe or the vial. Additionally, in many instances, air bubbles are drawn into the syringe as fluid is withdrawn from the vial. To rid a syringe of bubbles after removal from the vial, medical professionals often flick the syringe, gathering all bubbles near the opening of the syringe, and then force the bubbles out. In so doing, a small amount of liquid usually is expelled from the syringe as well. Medical personnel generally do not take the extra step to re-couple the syringe with the vial before expelling the bubbles and fluid. In some instances, this may even be prohibited by laws and regulations. Such laws and regulations may also necessitate expelling overdrawn fluid at some location outside of the vial in certain cases. Moreover, even if extra air or fluid were attempted to be reinserted in the vial, pressure differences can sometimes lead to inaccurate measurements of withdrawn fluid.

To address these problems caused by pressure differentials, medical professionals frequently pre-fill an empty syringe with a precise volume of ambient air corresponding to the volume of fluid that they intend to withdraw from the vial. The medical professionals then pierce the vial and expel this ambient air into the vial, temporarily increasing the pressure within the vial. When the desired volume of fluid is later withdrawn, the pressure differential between the interior of the syringe and the interior of the vial is generally near equilibrium. Small adjustments of the fluid volume within the syringe can then be made to remove air bubbles without resulting in a demonstrable pressure differential between the vial and the syringe. However, a significant disadvantage to this approach is that ambient air, especially in a hospital setting, may contain various airborne viruses, bacteria, dust, spores, molds, and other unsanitary and harmful debris. The pre-filled ambient air in the syringe may contain one or more of these harmful substances, which may then mix with the medicine or other therapeutic fluid in the vial. If this contaminated fluid is injected directly into a patient's bloodstream, it can be particularly dangerous because it circumvents many of the body's natural defenses to airborne pathogens. Moreover, patients who need the medicine and other therapeutic fluids are more likely to be suffering from a diminished infection-fighting capacity.

In the context of oncology and certain other drugs, all of the foregoing problems can be especially serious. Such drugs, although helpful when injected into the bloodstream of a patient, can be extremely harmful if inhaled or touched. Accordingly, such drugs can be dangerous if allowed to spurt unpredictably from a vial due to pressure differences. Furthermore, these drugs are often volatile and may instantly aerosolize when exposed to ambient air. Accordingly, expelling a small amount of such drugs in order to clear a syringe of bubbles or excess fluid, even in a controlled manner, is generally not a viable option, especially for medical personnel who may repeat such activities numerous times each day. Consequently, there is a need for a vial adaptor that reduces the above-noted problems.

Certain devices exist that allow air to be drawn into a vial as fluid is removed therefrom. These devices generally use filters. Although filters remove a large number of contaminants from air as it enters the vial, the filters are not perfect. In some instances the filters are hydrophobic membranes comprising Gortex® or Teflon®. Multiple problems arise from such assemblies. For example, the hydrophobic nature of the filters prevents a user from returning overdrawn fluid to the vial. For example, in some instances, air is allowed into the vial through a channel as the user withdraws fluid from the vial. However, if the user forces fluid back into the vial, fluid is also forced through the channel until it contacts the filter. Because the filter is a barrier to fluid, the pressure within the vial will increase as the medical professional continues to force fluid into the vial. As stated above, such pressure increases are prohibited by law in some instances, and in any event, can make it difficult for the user to obtain an accurate dosage. In addition, pressure differences can easily damage the thin and delicate membranes, causing the filters to occasionally leak and permit harmful liquids to escape.

Furthermore, the use of Gortex® or Teflon® membranes in filters generally requires ethylene oxide (EtO) sterilization, which is expensive and inconvenient for medical device manufacturers. Preferred alternative methods of sterilization, such as gamma sterilization and electron beam sterilization, generally ruin such filters. In some instances, the latter forms of sterilization degrade the Teflon® membranes, making the filters prone to leakage.

In addition, some existing devices are difficult or complicated to couple with a vial and can require multiple specialized apparatuses to effectuate such coupling. Complicated procedures can become overly burdensome to medical personnel who repeat the procedures numerous times each day. Furthermore, certain of such complicated devices are bulky and unbalanced. Coupling such a device with a vial generally creates a top-heavy, metastable system that is prone to being tipped over and possibly spilled.

Disclosed herein are numerous embodiments of vial adaptors that reduce or eliminate many of the above-noted problems.

FIG. 1 is a schematic illustration of a container 10, such as a medicinal vial, that can be coupled with an extractor 20 and a regulator 30. In certain arrangements, the regulator 30 allows the removal of some or all of the contents of the container 10 via the extractor 20 without a significant change of pressure within the container 10.

In general, the container 10 is hermetically sealed to preserve the contents of the container 10 in a sterile environment. The container 10 can be evacuated or pressurized upon sealing. In some instances, the container 10 is partially or completely filled with a liquid, such as a drug or other medical fluid. In such instances, one or more gases can also be sealed in the container 10. Although embodiments and examples are provided herein in the medical field, the inventions are not confined to the medical field only and certain embodiments can be used in many other fields.

The extractor 20 generally provides access to contents of the container 10 such that the contents may be removed or added to. In certain arrangements, the extractor 20 comprises an opening between the interior and exterior of the container 10. The extractor 20 can further comprise a passageway between the interior and exterior of the container 10. In some configurations, the passageway of the extractor 20 can be selectively opened and closed. In some arrangements, the extractor 20 comprises a conduit extending through a surface of the container 10. The extractor 20 can be integrally formed with the container 10 prior to the sealing thereof or introduced to the container 10 after the container 10 has been sealed.

In some configurations, the extractor 20 is in fluid communication with the container 10, as indicated by an arrow 21. In certain of these configurations, when the pressure inside the container 10 varies from that of the surrounding environment, the introduction of the extractor 20 to the container 10 causes a transfer through the extractor 20. For example, in some arrangements, the pressure of the environment that surrounds the container 10 exceeds the pressure within the container 10, which may cause ambient air from the environment to ingress through the extractor 20 upon insertion of the extractor 20 into the container 10. In other arrangements, the pressure inside the container 10 exceeds that of the surrounding environment, causing the contents of the container 10 to egress through the extractor 20.

In some configurations, the extractor 20 is coupled with an exchange device 40. In certain instances, the extractor 20 and the exchange device 40 are separable. In some instances, the extractor 20 and the exchange device 40 are integrally formed. The exchange device 40 is configured to accept fluids and/or gases from the container 10 via the extractor 20, to introduce fluids and/or gases to the container 10 via the extractor 20, or to do some combination of the two. In some arrangements, the exchange device 40 is in fluid communication with the extractor 20, as indicated by an arrow 24. In certain configurations, the exchange device 40 comprises a medical instrument, such as a syringe.

In some instances, the exchange device 40 is configured to remove some or all of the contents of the container 10 via the extractor 20. In certain arrangements, the exchange device 40 can remove the contents independent of pressure differences, or lack thereof, between the interior of the container 10 and the surrounding environment. For example, in instances where the pressure outside of the container 10 exceeds that within the container 10, an exchange device 40 comprising a syringe can remove the contents of the container 10 if sufficient force is exerted to extract the plunger from the syringe. The exchange device 40 can similarly introduce fluids and/or gases to the container 10 independent of pressure differences between the interior of the container 10 and the surrounding environment.

In certain configurations, the regulator 30 is coupled with the container 10. The regulator 30 generally regulates the pressure within the container 10. As used herein, the term regulate, or any derivative thereof, is a broad term used in its ordinary sense and includes, unless otherwise noted, any active, affirmative, or positive activity, or any passive, reactive, respondent, accommodating, or compensating activity that tends to effect a change. In some instances, the regulator 30 substantially maintains a pressure difference, or equilibrium, between the interior of the container 10 and the surrounding environment. As used herein, the term maintain, or any derivative thereof, is a broad term used in its ordinary sense and includes the tendency to preserve an original condition for some period, whether or not that condition is ultimately altered. In some instances, the regulator 30 maintains a substantially constant pressure within the container 10. In certain instances, the pressure within the container 10 varies by no more than about 1 psi, no more than about 2 psi, no more than about 3 psi, no more than about 4 psi, or no more than about 5 psi. In still further instances, the regulator 30 equalizes pressures exerted on the contents of the container 10. As used herein, the term equalize, or any derivative thereof, is a broad term used in its ordinary sense and includes the movement toward equilibrium, whether or not equilibrium is achieved. In other configurations, the regulator 30 is coupled with the container 10 to allow or encourage equalization of a pressure difference between the interior of the container 10 and some other environment, such as the environment surrounding the container 10 or an environment within the exchange device 40. In some arrangements, a single device comprises the regulator 30 and the extractor 20, while in other arrangements, the regulator 30 and the extractor 20 are separate units.

The regulator 30 is generally in communication with the container 10, as indicated by an arrow 31, and a reservoir 50, as indicated by another arrow 35. In some configurations, the reservoir 50 comprises at least a portion of the environment surrounding the container 10. In other configurations, the reservoir 50 comprises a container, canister, bag, or other holder dedicated to the regulator 30. As used herein, the term bag is a broad term used in its ordinary sense and includes, without limitation, any sack, balloon, bladder, receptacle, reservoir, enclosure, diaphragm, or membrane capable of expanding and/or contracting, including structures comprising a flexible, supple, pliable, resilient, elastic, and/or expandable material. In some embodiments, the reservoir 50 comprises a gas and/or a liquid.

In certain embodiments, the regulator 30 provides fluid communication between the container 10 and the reservoir 50. In certain of such embodiments, it is preferred that the reservoir 50 comprise mainly gas so as not to dilute any liquid contents of the container 10. In some arrangements, the regulator 30 comprises a filter to purify gas or liquid entering the container 10, thereby reducing the risk of contaminating the contents of the container 10. In certain arrangements, the filter is hydrophobic such that air can enter the container 10 but fluid cannot escape therefrom.

In other embodiments, the regulator 30 prevents fluid communication between the container 10 and the reservoir 50. In certain of such embodiments, the regulator 30 serves as an interface between the container 10 and the reservoir 50. In some arrangements, the regulator 30 comprises a substantially impervious bag for accommodating ingress of gas and/or liquid to the container 10 or egress of gas and/or liquid from the container 10.

Figure 2:
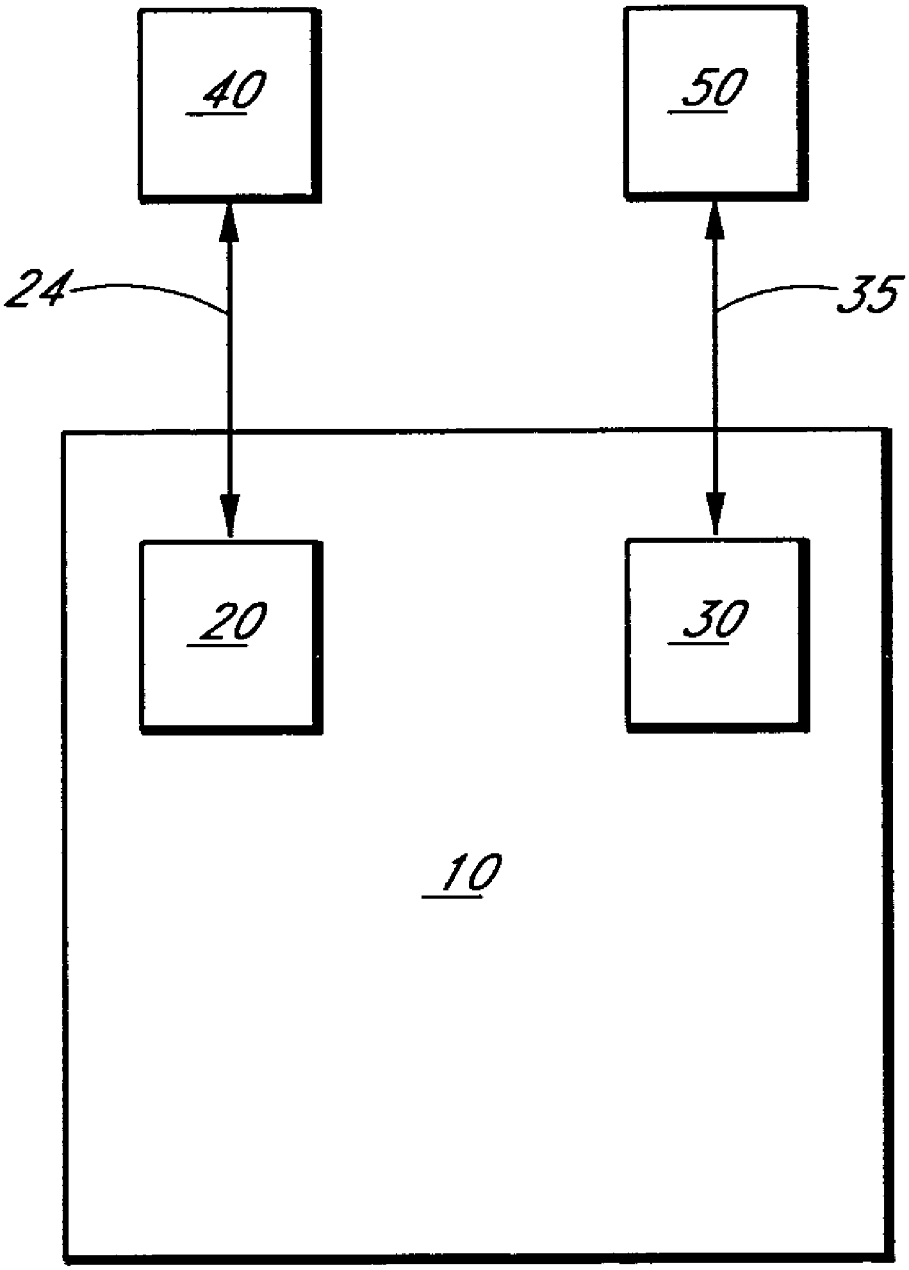
FIG. 2 is a schematic illustration of another system for removing fluid from and/or injecting fluid into a vial.

As schematically illustrated in FIG. 2, in certain embodiments, the extractor 20, or some portion thereof, is located within the container 10. As detailed above, the extractor 20 can be integrally formed with the container 10 or separate therefrom. In some embodiments, the regulator 30, or some portion thereof, is located within the container 10. In such embodiments, the regulator 30 can be placed in the container 10 prior to the sealing thereof or it can be introduced to the container 10 thereafter. In some arrangements, the regulator 30 is integrally formed with the container 10. It is possible to have any combination of the extractor 20, or some portion thereof, entirely within, partially within, or outside of the container 10 and/or the regulator 30, or some portion thereof, entirely within, partially within, or outside of the container 10.

In certain embodiments, the extractor 20 is in fluid communication with the container 10. In further embodiments, the extractor 20 is in fluid communication with the exchange device 40, as indicated by the arrow 24.

The regulator 30 can be in fluid or non-fluid communication with the container 10. In some embodiments, the regulator 30 is located entirely within the container 10. In certain of such embodiments, the regulator 30 comprises a closed bag configured to expand or contract within the container 10 to maintain a substantially constant pressure within the container 10. In other embodiments, the regulator 30 is in communication, either fluid or non-fluid, with the reservoir 50, as indicated by the arrow 35.

Figure 3:
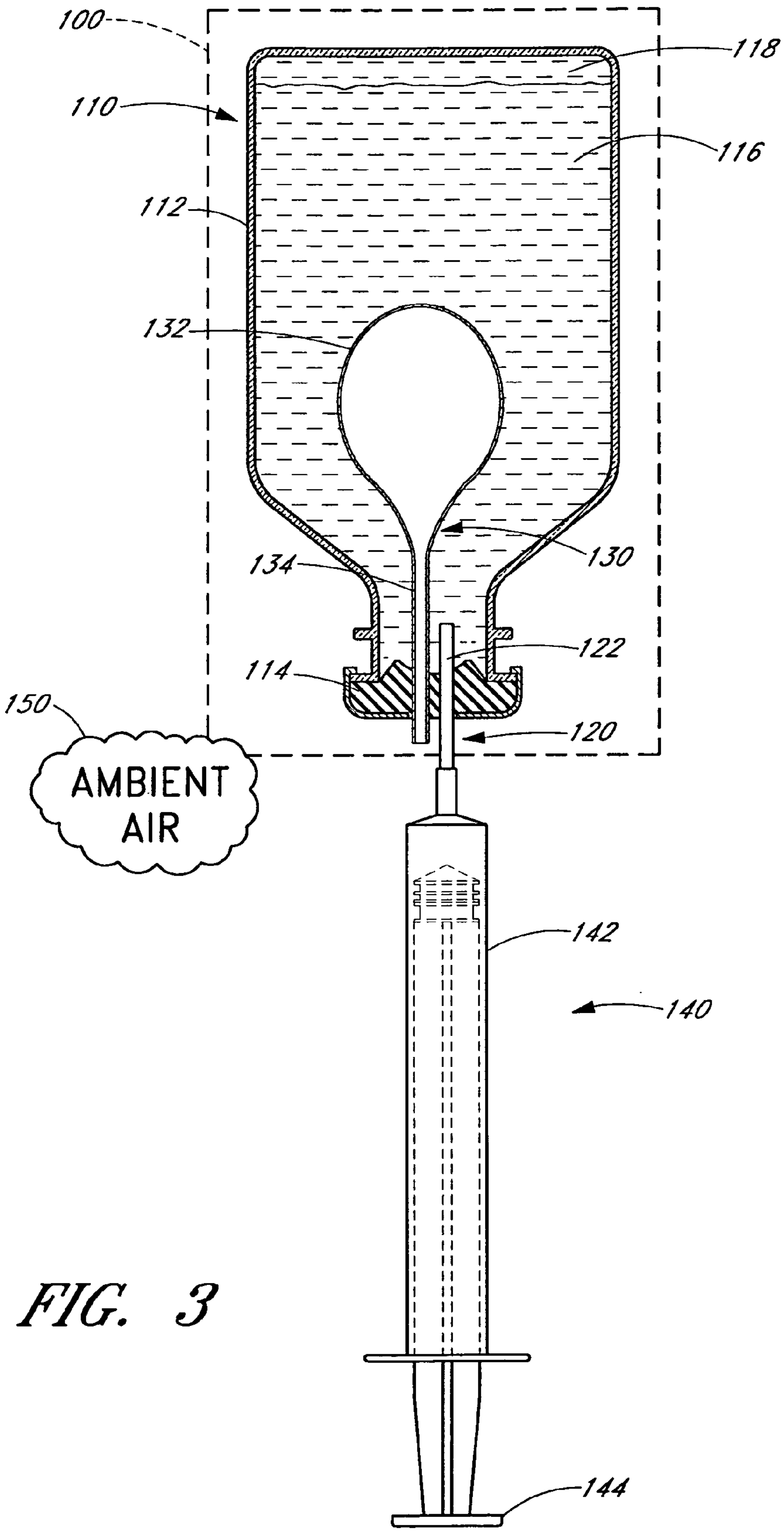
FIG. 3 is an illustration of another system for removing fluid from and/or injecting fluid into a vial.

FIG. 3 illustrates an embodiment of a system 100 comprising a vial 110, an extractor 120, and a regulator 130. The vial 110 comprises a body 112 and a cap 114. In the illustrated embodiment, the vial 110 contains a medical fluid 116 and a relatively small amount of sterilized air 118. In certain arrangements, the fluid 116 is removed from the vial 110 when the vial 110 is oriented with the cap 114 facing downward (i.e., the cap 114 is between the fluid and the ground). The extractor 120 comprises a conduit 122 fluidly connected at one end to an exchange device 140, which comprises a standard syringe 142 with a plunger 144. The conduit 122 extends through the cap 114 and into the fluid 116. The regulator 130 comprises a bag 132 and a conduit 134. The bag 132 and the conduit 134 are in fluid communication with a reservoir 150, which comprises the ambient air surrounding both the system 100 and the exchange device 140. The bag 132 comprises a substantially impervious material such that the fluid 116 and the air 118 inside the vial 110 do not contact the ambient air located at the interior of the bag 132.

In the illustrated embodiment, areas outside of the vial 110 are at atmospheric pressure. Accordingly, the pressure on the syringe plunger 144 is equal to the pressure on the interior of the bag 132, and the system 100 is in equilibrium. The plunger 144 can be withdrawn to fill the syringe 142 with the fluid 116. Withdrawing the plunger 144 increases the effective volume of the vial 110, thereby decreasing the pressure within the vial 110. A decrease of pressure within the vial 110 increases the difference in pressure between the interior and exterior of the bag 132, which causes the bag 132 to expand and force fluid into the syringe 142. In effect, the bag 132 expands within the vial 110 to a new volume that compensates for the volume of the fluid 116 withdrawn from the vial 110. Thus, once the plunger 144 ceases from being withdrawn from the vial 110, the system is again in equilibrium. Advantageously, the system 100 operates near equilibrium, facilitating withdrawal of the fluid 116. Furthermore, due to the equilibrium of the system 100, the plunger 144 remains at the position to which it is withdrawn, thereby allowing removal of an accurate amount of the fluid 116 from the vial 110.

In certain arrangements, the increased volume of the bag 132 is approximately equal to the volume of liquid removed from the vial 110. In some arrangements, the volume of the bag 132 increases at a slower rate as greater amounts of fluid are withdrawn from the vial 110 such that the volume of fluid withdrawn from the vial 110 is greater than the increased volume of the bag 132.

In some arrangements, the bag 132 can stretch to expand beyond a resting volume. In some instances, the stretching gives rise to a restorative force that effectively creates a difference in pressure between the inside of the bag 132 and the inside of the vial 110. For example, a slight vacuum inside the vial 110 can be created when the bag 132 is stretched.

In certain instances, more of the fluid 116 than desired initially might be withdrawn inadvertently. In other instances, some of the air 118 in the vial 110 initially might be withdrawn, creating unwanted bubbles within the syringe 142. It may thus be desirable to inject some of the withdrawn fluid 116 and/or air 118 back into the vial 110, which can be accomplished by depressing the plunger 144. Depressing the plunger 144 increases the pressure inside the vial 110 and causes the bag 132 to contract. When the manual force applied to the plunger 144 ceases, the plunger is again exposed to atmospheric pressure alone, as is the interior of the bag 132. Accordingly, the system 100 is again at equilibrium. Because the system 100 operates near equilibrium as the fluid 116 and/or the air 118 are injected into the vial 110, the pressure within the vial 110 does not significantly increase as the fluid 116 and/or air 118 is returned to the vial 110.

Figure 4:
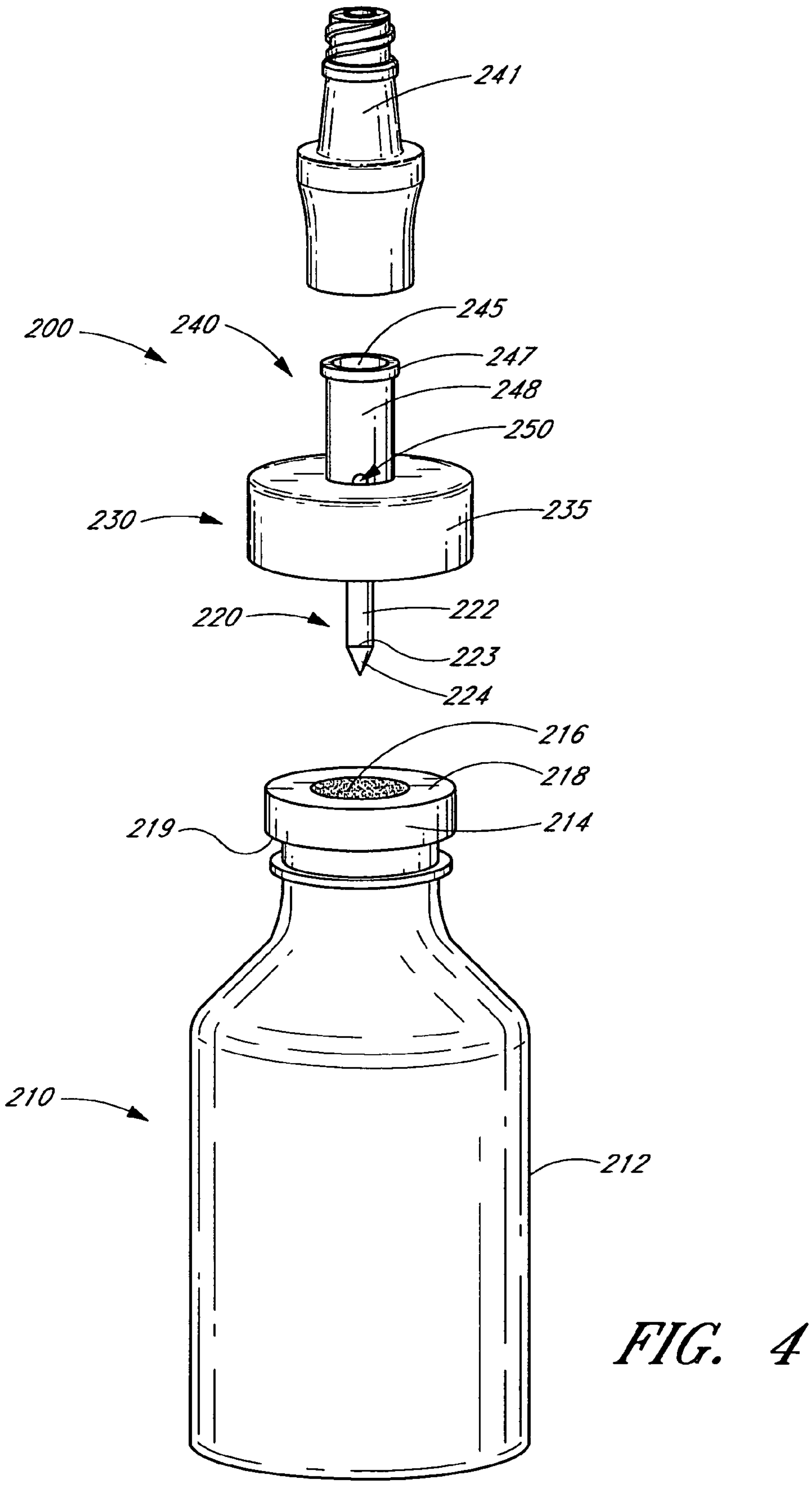
FIG. 4 is a perspective view of a vial adaptor and a vial.

FIG. 4 illustrates an embodiment of a vial adaptor 200 for coupling with a vial 210. The vial 210 can comprise any suitable container for storing medical fluids. In some instances, the vial 210 comprises any of a number of standard medical vials known in the art, such as those produced by Abbott Laboratories of Abbott Park, Ill. Preferably, the vial 210 is capable of being hermetically sealed. In some configurations, the vial 210 comprises a body 212 and a cap 214. The body 212 preferably comprises a rigid, substantially impervious material, such as plastic or glass. In some embodiments, the cap 214 comprises a septum 216 and a casing 218. The septum 216 can comprise an elastomeric material capable of deforming in such a way when punctured by an item that it forms a substantially airtight seal around that item. For example, in some instances, the septum 216 comprises silicone rubber or butyl rubber. The casing 218 can comprise any suitable material for sealing the vial 210. In some instances, the casing 218 comprises metal that is crimped around the septum 216 and a proximal portion of the body 212 in order to form a substantially airtight seal between the septum 216 and the vial 210. In certain embodiments, the cap 214 defines ridge 219 that extends outwardly from the top of the body 212.

In certain embodiments, the adaptor 200 comprises a piercing member 220. In some configurations, the piercing member 220 comprises a sheath 222. The sheath 222 can be substantially cylindrical, as shown, or it can assume other geometric configurations. In some instances, the sheath 222 tapers toward a distal end 223. In some arrangements, the distal end 223 defines a point that can be centered with respect to an axis of the piercing member 220 or offset therefrom. In certain embodiments, the distal end 223 is angled from one side of the sheath 222 to the opposite side. The sheath 222 can comprise a rigid material, such as metal or plastic, suitable for insertion through the septum 216. In certain embodiments the sheath 222 comprises polycarbonate plastic.

In some configurations, the piercing member 220 comprises a tip 224. The tip 224 can have a variety of shapes and configurations. In some instances, the tip 224 is configured to facilitate insertion of the sheath 222 through the septum 216. As illustrated, the tip 224, or a portion thereof, can be substantially conical, coming to a point at or near the axial center of the piercing member 220. In some configurations, the tip 224 angles from one side of the piercing member 220 to the other. In some instances, the tip 224 is separable from the sheath 222. In other instances, the tip 224 and the sheath 222 are permanently joined, and can be integrally formed. In various embodiments, the tip 224 comprises acrylic plastic, ABS plastic, or polycarbonate plastic.

In some embodiments, the adaptor 200 comprises a cap connector 230. As illustrated, the cap connector 230 can substantially conform to the shape of the cap 214. In certain configurations, the cap connector 230 comprises a rigid material, such as plastic or metal, that substantially maintains its shape after minor deformations. In some embodiments, the cap connector 230 comprises polycarbonate plastic. In some arrangements, the cap connector 230 comprises a sleeve 235 configured to snap over the ridge 219 and tightly engage the cap 214. As more fully described below, in some instances, the cap connector 230 comprises a material around an interior surface of the sleeve 235 for forming a substantially airtight seal with the cap 214. In some embodiments, the cap connector 230 comprises an elastic material that is stretched over the ridge 219 to form a seal around the cap 214. In some embodiments, the cap connector 230 resembles the structures shown in FIGS. 6 and 7 of and described in the specification of U.S. Pat. No. 5,685,866, the entire contents of which are hereby incorporated by reference herein and are made a part of this specification.

In certain embodiments, the adaptor 200 comprises a medical connector interface 240 for coupling the adaptor 200 with a medical connector 241, another medical device (not shown), or any other instrument used in extracting fluid from or injecting fluid into the vial 210. In certain embodiments, the medical connector interface 240 comprises a sidewall 248 that defines a proximal portion of an extractor channel 245 through which fluid may flow. In some instances, the extractor channel 245 extends through the cap connector 230 and through a portion of the piercing member 220 such that the medical connector interface 240 is in fluid communication with the piercing member 220. The sidewall 248 can assume any suitable configuration for coupling with the medical connector 241, a medical device, or another instrument. In the illustrated embodiment, the sidewall 248 is substantially cylindrical and extends generally proximally from the cap connector 230.

In certain configurations, the medical connector interface 240 comprises a flange 247 to aid in coupling the adaptor 200 with the medical connector 241, a medical device, or another instrument. The flange 247 can be configured to accept any suitable medical connector 241, including connectors capable of sealing upon removal of a medical device therefrom. In some instances, the flange 247 is sized and configured to accept the Clave® connector, available from ICU Medical, Inc. of San Clemente, Calif. Certain features of the Clave® connector are disclosed in U.S. Pat. No. 5,685,866. Connectors of many other varieties, including other needleless connectors, can also be used. The connector 241 can be permanently or separably attached to the medical connector interface 240. In other arrangements, the flange 247 is threaded, configured to accept a Luer connector, or otherwise shaped to attach directly to a medical device, such as a syringe, or to other instruments.

In certain embodiments, the medical connector interface 240 is advantageously centered on an axial center of the adaptor 200. Such a configuration provides stability to a system comprising the adaptor 200 coupled with the vial 210, thereby making the coupled system less likely to tip over. Accordingly, the adaptor 200 is less likely to cause dangerous leaks or spills occasioned by accidental bumping or tipping of the adaptor 200 or the vial 210.

In some embodiments, the piercing member 220, the cap connector 230, and the medical connector interface 240 are integrally formed of a unitary piece of material, such as polycarbonate plastic. In other embodiments, one or more of the piercing member 220, the cap connector 230, and the medical connector interface 240 comprise a separate piece. The separate pieces can be joined in any suitable manner, such as by glue, epoxy, ultrasonic welding, etc. Preferably, connections between joined pieces create substantially airtight bonds between the pieces. In further arrangements, any of the piercing member 220, the cap connector 230, or the medical connector interface 240 can comprise more than one piece.

In certain embodiments, the adaptor 200 comprises a regulator aperture 250. In many embodiments, the regulator aperture 250 is located at a position on the adaptor 200 that remains exposed to the exterior of the vial 210 when the piercing member 220 is inserted in the vial 210. In the illustrated embodiment, the regulator aperture 250 is located at a junction of the cap connector 230 and the medical connector interface 240. In certain embodiments, the regulator aperture 250 allows fluid communication between the environment surrounding the vial 210 and a regulator channel 225 (see FIG. 5) which extends through the cap connector 230 and through the piercing member 220.

Figure 5:
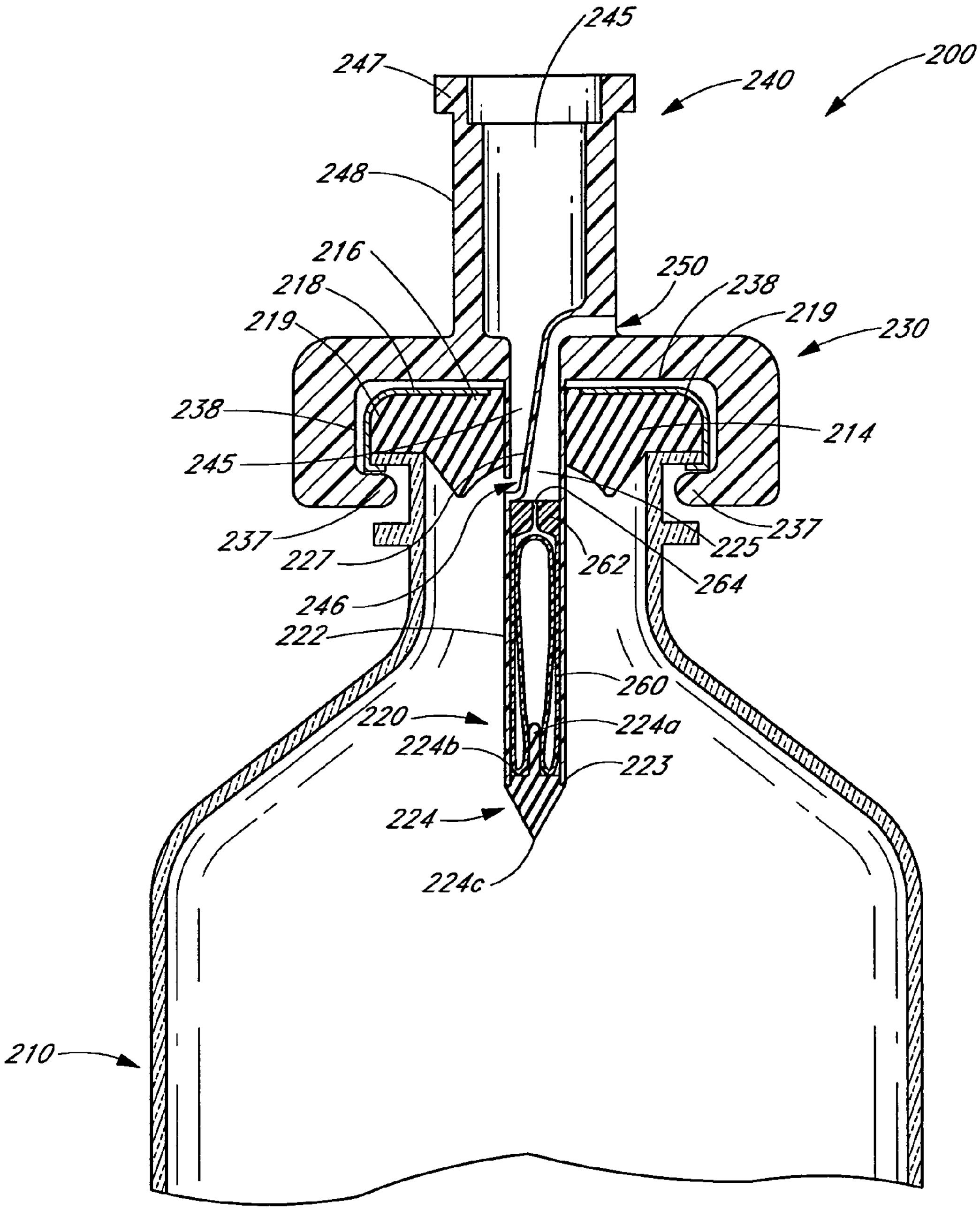
FIG. 5 is a partial cross-sectional view of the vial adaptor of FIG. 4 coupled with a vial in an initial stage.

FIG. 5 illustrates a cross-section of the vial adaptor 200 coupled with the vial 210. In the illustrated embodiment, the cap connector 230 firmly secures the adaptor 200 to the cap 214 and the piercing member 220 extends through the septum 216 into the interior of the vial 210. In some embodiments, the piercing member 220 is oriented substantially perpendicularly with respect to the cap 214 when the adaptor 200 and the vial 210 are coupled. Other configurations are also possible. As shown, in some embodiments, the piercing member 220 houses a bag 260.

In certain embodiments, the cap connector 230 comprises one or more projections 237 that aid in securing the adaptor 200 to the vial 210. The one or more projections 237 extend toward an axial center of the cap connector 230. In some configurations, the one or more projections 337 comprise a single circular flange extending around the interior of the cap connector 330. The cap connector 230 can be sized and configured such that an upper surface of the one or more projections 237 abuts a lower surface of the ridge 219, helping secure the adaptor 200 in place.

The one or more projections 237 can be rounded, chamfered, or otherwise shaped to facilitate the coupling of the adaptor 200 and the vial 210. For example, as the adaptor 200 having rounded projections 237 is introduced to the vial 210, a lower surface of the rounded projections 237 abuts a top surface of the cap 214. As the adaptor 200 is advanced onto the vial 210, the rounded surfaces cause the cap connector 230 to expand radially outward. As the adaptor 200 is advanced further onto the vial 210, a resilient force of the deformed cap connector 220 seats the one or more projections 237 under the ridge 219, securing the adaptor 200 in place.

In some embodiments, the cap connector 230 is sized and configured such that an inner surface 238 of the cap connector 230 contacts the cap 214. In some embodiments, a portion of the cap connector 230 contacts the cap 214 in substantially airtight engagement. In certain embodiments, a portion of the inner surface 238 surrounding either the septum 216 or the casing 218 is lined with a material, such as rubber or plastic, to ensure the formation of a substantially airtight seal between the adaptor 200 and the vial 210.

The piercing member 220 can comprise the tip 224 and the sheath 222, as noted above. In some embodiments, the tip 224 is configured to pierce the septum 216 to facilitate passage therethrough of the sheath 222. In some instances, the tip 224 comprises a proximal extension 224*a* for securing the tip 224 to the sheath 222. As described below, in some arrangements, the bag 260 is folded within the sheath 222. Accordingly, a portion of the folded bag 260 can contact the proximal extension 224*a* and hold it in place. In many arrangements, the proximal extension 224*a* comprises a material capable of frictionally engaging the bag 260. In various embodiments, the proximal extension 224*a* comprises polycarbonate plastic, silicone rubber, butyl rubber, or closed cell foam. In some arrangements, the proximal extension 224*a* is coated with an adhesive to engage the bag 260. The proximal extension 224*a* can be attached to the tip 224 by any suitable means, or it can be integrally formed therewith.

In some arrangements, the tip 224 can be adhered to, friction fit within, snapped into, or otherwise attached in a temporary fashion to the distal end 223 of the sheath 222, either instead of or in addition to any engagement between the proximal extension 224*a* and the bag 260. As discussed below, in some arrangements, the tip 224 disengages from the sheath 222 and/or the bag 260 as fluid is withdrawn from the vial 210. In other arrangements, the tip 224 disengages from the sheath 222 and/or the bag 260 upon passing through the septum 216, such as when atmospheric pressure within the sheath 222 is sufficiently higher than the pressure within the vial 210. In other instances, a volume of air between the tip 224 and the bag 260 is pressurized to achieve the same result.

In some embodiments, the tip 224 comprises a shoulder 224*b*. In some instances, the outer perimeter of the shoulder 224*b* is shaped to conform to the interior perimeter of the sheath 222. Accordingly, the shoulder 224*b* can center the tip 224 with respect to the sheath 222 and keep the tip 224 oriented properly for insertion through the septum 216. In some instances, the outer perimeter of the shoulder 224*b* is slightly smaller than the interior perimeter of the sheath 222, allowing the tip 224 to easily disengage or slide from the sheath 222 as the bag 260 is deployed. In certain embodiments, the tip 224 comprises the shoulder 224*b*, but does not comprise the proximal extension 224*a*.

In certain arrangements, the proximal extension 224*a* serves to maintain a proper orientation of the tip 224 with respect to the sheath 222 for insertion of the tip 224 through the septum 216. In some instances, the tip 224 rotates with respect to the sheath 222 as the tip 224 contacts the septum 216 such that the proximal extension 224*a* is angled with respect to the axial center of the sheath 222. In some arrangements, the proximal extension 224*a* is sufficiently long that an end thereof contacts the interior surface of the sheath 222. In many instances, the contact is indirect, where one or more layers of the balloon 260 are located between the proximal extension 224*a* and the sheath 222. This contact can prevent the tip 224 from rotating too far, such that a distal end 224*c* thereof is not directed at an angle that is relatively perpendicular to the septum 216.

The sheath 222 is generally sized and dimensioned to be inserted through the septum 216 without breaking and, in some instances, with relative ease. Accordingly, in various embodiments, the sheath 222 has a cross-sectional area of between about 0.025 and about 0.075 square inches, between about 0.040 and about 0.060 square inches, or between about 0.045 and about 0.055 square inches. In other embodiments, the cross-sectional area is less than about 0.075 square inches, less than about 0.060 square inches, or less than about 0.055 square inches. In still other embodiments, the cross-sectional area is greater than about 0.025 square inches, greater than about 0.035 square inches, or greater than about 0.045 square inches. In some embodiments, the cross-sectional area is about 0.050 square inches.

The sheath 222 can assume any of a number of cross-sectional geometries, such as, for example, oval, ellipsoidal, square, rectangular, hexagonal, or diamond-shaped. The cross-sectional geometry of the sheath 222 can vary along a length thereof in size and/or shape. In some embodiments, the sheath 222 has substantially circular cross-sections along a substantial portion of a length thereof. A circular geometry provides the sheath 222 with substantially equal strength in all radial directions, thereby preventing bending or breaking that might otherwise occur upon insertion of the sheath 222. The symmetry of an opening created in the septum 216 by the circular sheath 222 prevents pinching that might occur with angled geometries, allowing the sheath 222 to more easily be inserted through the septum 216. Advantageously, the matching circular symmetries of the piercing member 220 and the opening in the septum 216 ensure a tight fit between the piercing member 220 and the septum 216, even if the adaptor 200 is inadvertently twisted. Accordingly, the risk of dangerous liquids or gases escaping the vial 210, or of impure air entering the vial 210 and contaminating the contents thereof, can be reduced in some instances with a circularly symmetric configuration.

In some embodiments, the sheath 222 is hollow. In the illustrated embodiment, the inner and outer surfaces of the sheath 222 substantially conform to each other such that the sheath 222 has a substantially uniform thickness. In various embodiments, the thickness is between about 0.015 inches and 0.040 inches, between about 0.020 inches and 0.030 inches, or between about 0.024 inches and about 0.026 inches. In other embodiments, the thickness is greater than about 0.015 inches, greater than about 0.020 inches, or greater than about 0.025 inches. In still other embodiments, the thickness is less than about 0.040 inches, less than about 0.035 inches, or less than about 0.030 inches. In some embodiments, the thickness is about 0.025 inches.

In other embodiments, the inner surface of the sheath 222 varies in configuration from that of the outer surface of the sheath 222. Accordingly, in some arrangements, the thickness varies along the length of the sheath 222. In various embodiments, the thickness at one end, such as a proximal end, of the sheath is between about 0.015 inches and about 0.050 inches, between about 0.020 inches and about 0.040 inches, or between about 0.025 inches and about 0.035 inches, and the thickness at another end, such as the distal end 223, is between about 0.015 inches and 0.040 inches, between about 0.020 inches and 0.030 inches, or between about 0.023 inches and about 0.027 inches. In other embodiments, the thickness at one end of the sheath 222 is greater than about 0.015 inches, greater than about 0.020 inches, or greater than about 0.025 inches, and the thickness at another end thereof is greater than about 0.015 inches, greater than about 0.020 inches, or greater than about 0.025 inches. In still other embodiments, the thickness at one end of the sheath 222 is less than about 0.050 inches, less than about 0.040 inches, or less than about 0.035 inches, and the thickness at another end thereof is less than about 0.045 inches, less than about 0.035 inches, or less than about 0.030 inches. In some embodiments, the thickness at a proximal end of the sheath 222 is about 0.030 inches and the thickness at the distal end 223 is about 0.025 inches. In some arrangements, the cross-section of the inner surface of the sheath 222 is shaped differently from that of the outer surface. The shape and thickness of the sheath 222 can be altered to optimize the strength of the sheath 222.

In some instances the length of the sheath 222, as measured from a distal surface of the cap connector 230 to the distal end 223 is between about 0.8 inches to about 1.4 inches, between about 0.9 inches and about 1.3 inches, or between about 1.0 inches and 1.2 inches. In other instances the length is greater than about 0.8 inches, greater than about 0.9 inches, or greater than about 1.0 inches. In still other instances, the length is less than about 1.4 inches, less than about 1.3 inches, or less than about 1.2 inches. In some embodiments, the length is about 1.1 inches.

In certain embodiments, the sheath 222 at least partially encloses one or more channels. In the illustrated embodiment, the sheath 222 defines the outer boundary of a distal portion of a regulator channel 225 and the outer boundary of a distal portion of the extractor channel 245. An inner wall 227 extending from an inner surface of the sheath 222 to a distal portion of the medical connector interface 240 defines an inner boundary between the regulator channel 225 and the extractor channel 245. The regulator channel 225 extends from a proximal end 262 of the bag 260, through the cap connector 230, between the cap connector 230 and the medical connector interface 240, and terminates at a regulator aperture 250. The extractor channel 245 extends from an extractor aperture 246 formed in the sheath 222, through the cap connector 230, and through the medical connector interface 240.

In certain embodiments, the sheath 222 contains the bag 260. The bag 260 is generally configured to unfold, expand, compress, and/or contract, and can comprise any of a wide variety of materials, including Mylar®, polyester, polyethylene, polypropylene, saran, latex rubber, polyisoprene, silicone rubber, and polyurethane. In some embodiments, the bag 260 comprises a material capable of forming a substantially airtight seal with the sheath 222. In other embodiments, the bag 260 comprises a material that can be adhered to the sheath 222 in substantially airtight engagement. In many instances, the bag 260 comprises a material that is generally impervious to liquid and air. In certain embodiments, it is preferred that the bag 260 comprise a material that is inert with respect to the intended contents of the vial 210. In some embodiments, the bag 260 comprises latex-free silicone having a durometer between about 10 and about 40.

In some configurations, at least the proximal end 262 of the bag 260 is in substantially airtight engagement with the sheath 222. In some instances, such as that of the illustrated embodiment, a substantially airtight seal is achieved when the proximal end 262 is thicker than other portions of the bag 260 and fits more snugly within the sheath 222 than the remainder of the bag 260. In certain instances, the thicker proximal end 262 comprises a higher durometer material than the remainder of the bag 260. In some instances, the proximal end 262 comprises latex-free silicone having a durometer between about 40 and about 70. In other instances, the proximal end 262 is retained in the sheath 222 by a plastic sleeve (not shown) that presses the proximal end 262 against the sheath 222. In still further instances, the proximal end 262 is adhered to the sheath 222 by any suitable manner, such as by heat sealing or gluing. In some embodiments, a greater portion of the bag 260 than just the proximal end 262 is in substantially airtight contact with the sheath 222.

In certain embodiments, the proximal end 262 of the bag 260 defines a bag aperture 264. In some instances, the bag aperture 264 allows fluid communication between the interior of the bag 260 and the regulator channel 225. In certain arrangements, the bag aperture 264 extends along an axial center of the proximal end 262. Accordingly, in certain of such arrangements, a lower portion of the interior wall 227 is angled (as shown), offset, or positioned away from the center of the sheath 222 so as not to obstruct the bag aperture 264.

In certain arrangements, the entire bag 260 is located within the sheath 222 prior to insertion of the adaptor 200 into the vial 210. Accordingly, the bag 260 is generally protected by the sheath 222 from rips or tears when the adaptor 200 is inserted in the vial 210. In some instances, a liquid or gel lubricant is applied to an outer surface of the bag 260 to facilitate the insertion thereof into the sheath 222. In certain instances, isopropyl alcohol is applied to the bag 260 for this purpose. Alcohol is preferred because it is sterile, readily evaporates, and provides sufficient lubrication to allow relatively simple insertion of the bag 260.

In the illustrated embodiment, a portion of the bag 260 is internally folded or doubled back within the sheath 222. In certain of such embodiments, the bag 260 comprises a material that does not readily cling to itself, thereby allowing the bag 260 to easily be deployed. In some arrangements, a gel or liquid is applied to the interior surface of the bag 260 to encourage an easier deployment of the bag 260. In still other embodiments, one or more portions of the bag 260 are folded multiple times within the sheath 222. In certain of such embodiments, liquid or gel can be applied to portions of the interior and exterior surfaces of the bag 260 to allow easy deployment of the bag 260.

Figure 6A:
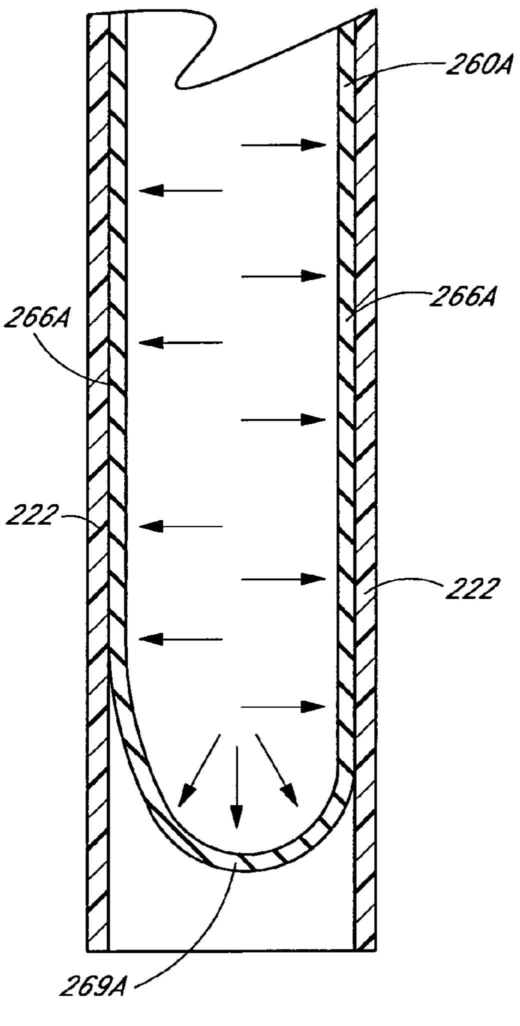
FIG. 6A is a cross-sectional view depicting a distal portion of a piercing member of a vial adaptor.
Figure 6B:
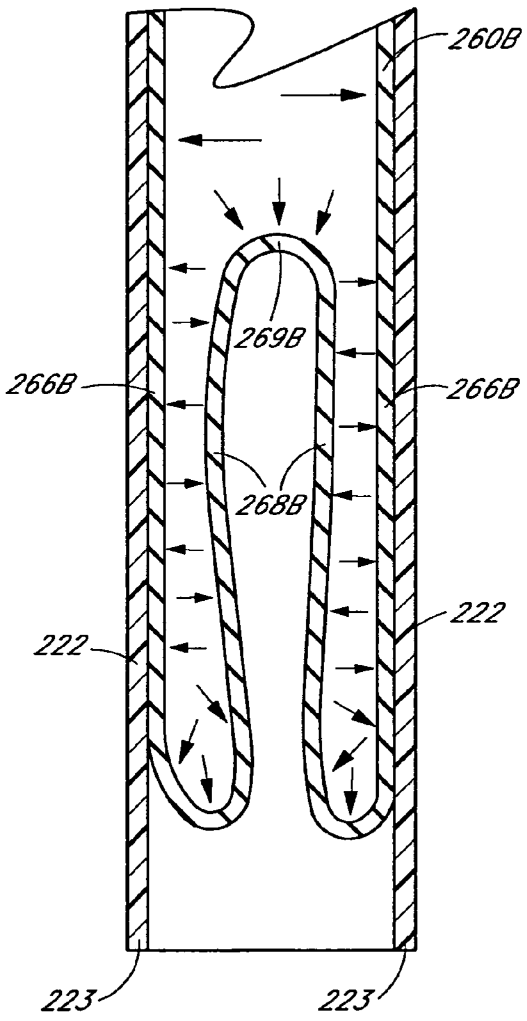
FIG. 6B is a cross-sectional view depicting a distal portion of a piercing member of a vial adaptor.

FIGS. 6A and 6B schematically illustrate why it can be desirable to fold the bag 260 within the sheath 222 in some instances. FIG. 6A illustrates a distal portion of the sheath 222 of the adaptor 200. The sheath 222 houses a substantially impervious bag 260A comprising a proximal portion 266A and a tip 269A. The adaptor 200 is coupled with a partially evacuated vial 210 (not shown) such that the pressure outside the vial 210 (e.g., atmospheric pressure) is higher than the pressure inside the vial 210. Accordingly, one side of the bag 260A can be exposed to the higher pressure outside the vial 210 and the other side of the bag 260A can be exposed to the lower pressure inside the vial 210. As a result of the pressure difference, the proximal portion 266A of the bag 260A is forced toward the inner surface of the sheath 222, as schematically depicted by various arrows. The friction thus generated tends to prevent the proximal portion 266A from expanding toward the distal end of the sheath 222. Consequently, in the illustrated configuration, only the tip 269A is able to expand when fluid is withdrawn from the vial 210. Withdrawing a large amount of fluid could put excessive strain on the tip 269A, causing it to tear or burst. In some embodiments, the composition of the bag 260A and/or the interface between the bag 260A and the interior wall of the sheath 222 permit much further expansion of the bag 260A in the distal direction.

FIG. 6B similarly illustrates a distal portion of the sheath 222 housing a substantially impervious bag 260B. The bag 260B comprises an outer portion 266B, an inner portion 268B, and a tip 269B. As in FIG. 6A, the adaptor 200 is coupled with a partially evacuated vial 210 such that the pressure outside the vial 210 is higher than the pressure inside the vial 210. The resulting pressure difference forces the outer portion 266B toward the sheath 222, as schematically depicted by various outward-pointing arrows. However, the pressure difference forces the inner portion 268B toward the center of the sheath 222, as schematically depicted by various inward-pointing arrows. As a result, friction between the inner portion 268B and the outer portion 266B of the bag 260B is reduced or eliminated, thereby facilitating expansion of the inner portion 268B and of the tip 269B toward and through the distal end 223 of the sheath 222. Consequently, in the illustrated embodiment, a larger portion of the bag 260B than that of the bag 260A is able to expand within the vial 210.

Figure 7:
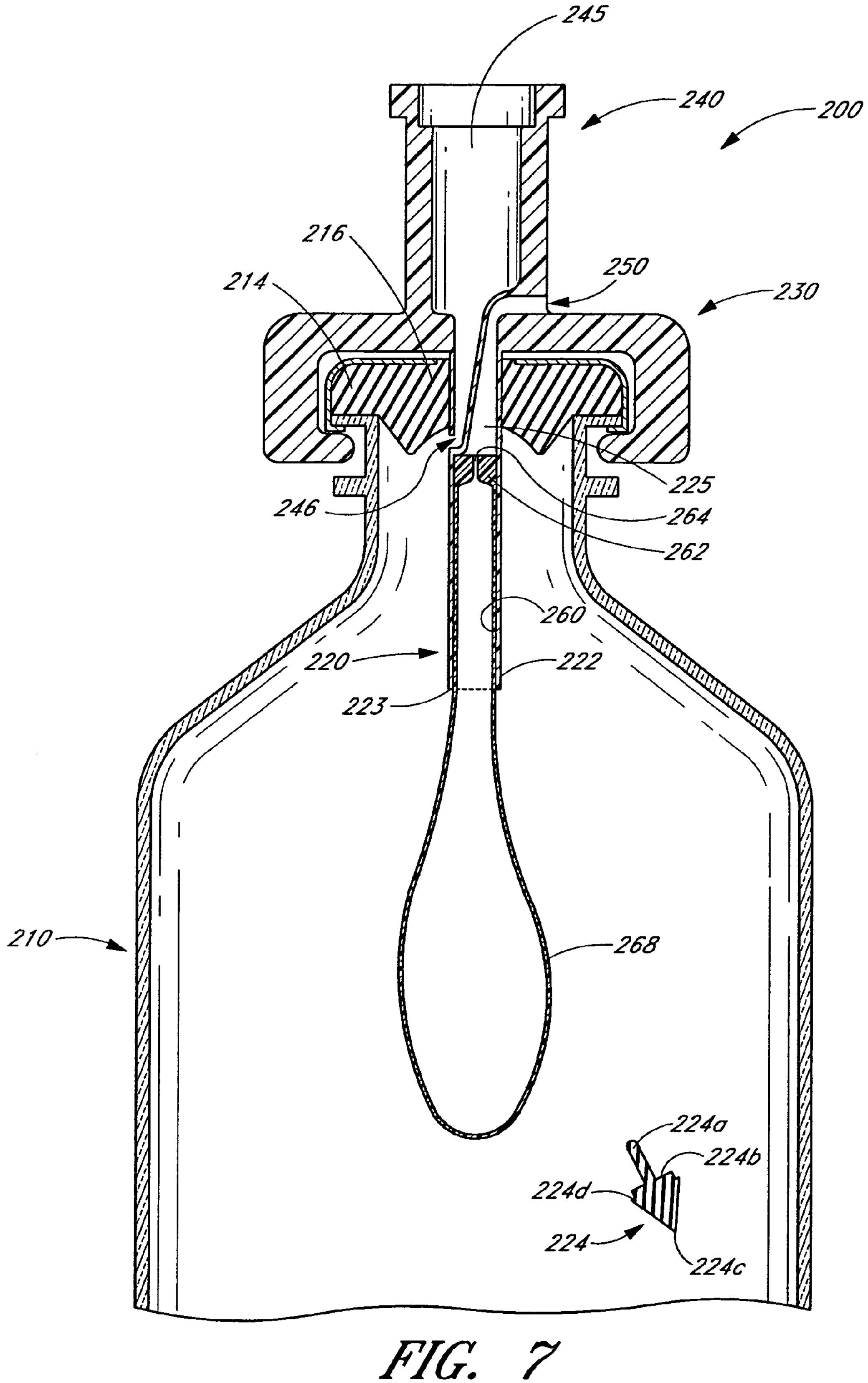
FIG. 7 is a partial cross-sectional view of the vial adaptor of FIG. 4 coupled with a vial in a subsequent stage.

FIG. 7 illustrates an embodiment of the adaptor 200 with the bag 260 deployed. As shown, in some embodiments, a distal portion 268 of the bag 260 extends beyond the sheath 222. In certain arrangements, a portion of the bag 260 that contacts the distal end 223 of the sheath 222 is thicker than surrounding portions in order to protect the bag 260 from ripping, puncturing, or tearing against the sheath 222.

In some embodiments, the bag 260 is sized and configured to substantially fill the vial 210. For example, in some arrangements, the bag 260 comprises a flexible, expandable material sized and configured to expand to fill a substantial portion of the volume within the vial 210. In some instances, the bag 260 is expandable to substantially fill a range of volumes such that a single adaptor 200 can be configured to operate with vials 210 of various sizes. In other arrangements, the bag 260 comprises a flexible, non-expandable material and is configured to unfold within the vial 210 to fill a portion thereof. In some embodiments, the bag 260 is configured to fill at least about 25, 30, 35, 40, 45, 50, 60, 70, 80, or 90 percent of one vial 210. In other embodiments, the bag 260 is configured to fill a volume equal to at least about 30, 40, 45, 50, 55, 60, 65, 70, 75, 80, 85, or 90 percent of the volume of fluid contained within the vial 210 prior to the coupling of the adapter 200 and the vial 210. In some embodiments, the bag 260 is configured to fill a volume equal to about 70 percent of the volume of fluid contained within the vial 210 prior to the coupling of the adaptor 200 and the vial 210. In other embodiments, the bag 260 is configured to fill at least about 25, 30, 35, 40, 45, 50, 60, 70, 80, or 90 percent of a first vial 210 having a first volume, and at least about 25, 30, 35, 40, 45, 50, 60, 70, 80, or 90 percent of a second vial 210 having a second volume larger than the first volume.

In some configurations, the distal portion 268 of the bag 260 is substantially bulbous, as shown. In some embodiments, the bulbous bag 260 comprises expandable material. In various arrangements, the distal portion 268 in an unexpanded state has an outer diameter of between about 0.10 inches and about 0.40 inches, between about 0.15 inches and about 0.35 inches, or between about 0.20 inches and about 0.30 inches. In some arrangements, the outer diameter is greater than about 0.10, greater than about 0.15 inches, or greater than about 0.20 inches. In other arrangements, the outer diameter is less than about 0.40 inches, less than about 0.35 inches, or less than about 0.30 inches. In some arrangements, the outer diameter is about 0.188 inches. In various arrangements, the distal portion 268 in an unexpanded state has a height of between about 0.50 inches and 1.00 inches, between about 0.60 inches and 0.90 inches, and between about 0.70 inches and 0.80 inches. In some arrangements, the height is greater than about 0.50 inches, greater than about 0.60 inches, or greater than about 0.70 inches. In other arrangements, the height is less than about 1.00 inches, less than about 0.90 inches, or less than about 0.80 inches. In some arrangements, the height is about 0.75 inches. In some embodiments, the distal portion is generally spherical. Various other embodiments of the distal portion 268 include, for example, generally conical, generally cylindrical, generally rectangular, and generally triangular.

In some configurations, the distal portion 268 of the bag 260 has a thickness between about 0.001 and 0.025 inches, between about 0.001 and 0.010 inches, or between about 0.010 and 0.025 inches. In other configurations, the thickness is greater than about 0.001 inches, greater than about 0.005 inches, greater than about 0.010 inches, greater than about 0.015 inches, or greater than about 0.020 inches. In still other configurations, the thickness is less than about 0.025 inches, less than about 0.020 inches, less than about 0.015 inches, less than about 0.010 inches, or less than about 0.005 inches. In some configurations, the thickness is about 0.015 inches.

As noted above, in some instances the body 212 of the vial 210 comprises a substantially rigid material, such as glass or plastic. Accordingly, configurations wherein the bag 260 is deployed within the vial 210 advantageously shield the bag 260 from accidental snags, rips, or tears. Furthermore, configurations wherein the bag 260 is located within the vial 210 can have a lower center of mass than other configurations, which helps to prevent accidental tipping and spilling of the vial 210.

With continued reference to FIG. 7, certain processes for using the adaptor 200 comprise inserting the piercing member 220 through the septum 216 until the cap connector 230 is firmly in place. Accordingly, the coupling of the adaptor 200 and the vial 210 can be accomplished in one simple step. In certain instances, the medical connector 241 is coupled with the medical connector interface 240. A medical device or other instrument (not shown), such as a syringe, can be coupled with the interface 240 or, if present, with the medical connector 241 (see FIG. 4). For convenience, reference will be made hereafter only to a syringe as an example of a medical device suitable for attachment to the medical connector interface 240, although numerous medical devices or other instruments can be used in connection with the adaptor 200 or the medical connector 241. In some instances, the syringe is placed in fluid communication with the vial 210. In some instances, the vial 210, the adaptor 200, the syringe, and, if present, the medical connector 241 are inverted such that the cap 214 is pointing downward (i.e., toward the ground). Any of the above procedures, or any combination thereof, can be performed in any possible order.

In some instances, a volume of fluid is withdrawn from the vial 210 via the syringe. As described above, the pressure within the vial 210 decreases as the fluid is withdrawn. Accordingly, in some instances, pressure within the regulator channel 225 forces the tip 224 away from the sheath 222. In other instances, pressure at the interior of the bag 260 causes the bag 260 to emerge from the sheath 222. In certain of such instances, as the bag 260 is deployed, it rolls outward and releases the proximal extension 224*a*, thus discharging the tip 224. The bag 260 is thus free to expand within the vial 210. In certain arrangements, therefore, it is desirable for the tip 224 to be engaged with the sheath 222 and/or bag 260 with sufficient strength to ensure that the tip 224 remains in place until the sheath 222 is inserted into the vial 210, yet with insufficient strength to prevent the tip 224 from separating from the sheath 222 and/or the bag 260 within the vial 210.

In some embodiments, the distal end 224*c* of the tip 224 is rounded such that it is sufficiently pointed to pierce the septum 216 when the adaptor 200 is coupled with the vial 210, but insufficiently pointed to pierce the bag 260 as the bag 260 is deployed or as it expands within the vial 210. In some arrangements, the proximal extension 224*a* is rounded for the same purpose.

In some instances, it is desirable to prevent the bag 260 from bearing against the distal end 224*c* of the tip 224 as the bag 260 expands within the vial 210. Accordingly, in certain arrangements, the proximal extension 224*a* is configured such that the tip 224, once separated from the sheath 222, naturally settles with the distal end 224*c* pointed away from the bag 260. For example, in some instances, the distal end 224*c* settles against the septum 216 when the vial 210 is oriented with the cap 214 pointing downward (i.e., with the cap 214 located between a volumetric center of the vial 210 and the ground). In some arrangements, the proximal extension 224*a* is relatively lightweight such that the center of mass of the tip 224 is located relatively near the distal end 224*c*. Accordingly, in some instances, when the tip 224 contacts the septum 216, the tip 224 is generally able to pivot about an edge 224*d* to reach a stable state with the distal end 224*c* pointed downward. In some arrangements, the edge 224*d* comprises the perimeter of the largest cross-section of the tip 224.

In certain embodiments, the proximal extension 224*a* is configured to allow the tip 224 to pivot such that the distal end 224*c* ultimately points downward, even when the proximal extension 224*a* is pointed downward upon initial contact with some surface of the vial 210, such as the septum 216. In certain instances, the length and/or weight of the proximal extension 224*a* are adjusted to achieve this result. In some instances, the length of the proximal extension 224*a* is between about 30 percent and about 60 percent, between about 35 percent and about 55 percent, or between about 40 percent and about 50 percent of the full length of the tip 224. In certain embodiments, the length of the proximal extension 224*a* is less than about 60 percent, less than about 55 percent, or less than about 50 percent of the full length of the tip 224. In other embodiments, the length is greater than about 60 percent of the full length of the tip 224. In still other embodiments, the length is less than about 30 percent of the full length of the tip 224. In some embodiments, the length is about 45 percent of the full length of the tip 224. Other arrangements are also possible to ensure that the distal end 224*c* does not bear against the bag 260 as the bag expands within the vial 210.

In some arrangements, it is also desirable that the proximal extension 224*a* not rigidly bear against the bag 260 as the bag 260 expands within the vial 210. Accordingly, in some embodiments, the proximal extension 224*a* comprises a flexible or compliant material, such as silicone rubber, butyl rubber, or closed cell foam. In other embodiments, the proximal extension 224*a* comprises a joint, such as a hinge or a ball-and-socket, that allows the proximal extension 224*a* to bend when contacted by the bag 260.

In certain configurations, fluid withdrawn from the vial 210 flows through the extractor aperture 246 and through the extractor channel 245 to the syringe. Simultaneously, in such configurations, ambient air flows from the surrounding environment, through the regulator aperture 250, through the regulator channel 225, through the bag aperture 264, and into the bag 260 to expand the bag 260. In certain arrangements, the increased volume of the bag 260 is approximately equal to the volume of liquid removed from the vial 210. In other arrangements, the volume of the bag 260 increases at a slower rate as greater amounts of fluid are withdrawn from the vial 210 such that the volume of fluid withdrawn from the vial 210 is greater than the increased volume of the bag 260. As noted above, the bag 260 can be configured to fill a substantial portion of the vial 210. In some configurations, the tip 224 is sized and configured such that it will not settle against the extractor aperture 246 and prevent fluid passage therethrough.

In some instances, more fluid than is desired may inadvertently be withdrawn from the vial 210 by the syringe. Accordingly, the excess fluid may be injected from the syringe back into the vial 210. In some configurations, when the fluid is injected to the vial 210, the fluid flows from the syringe, through the extractor channel 245, and through the extractor aperture 246 into the vial 210. As the fluid is forced into the vial 210, the pressure within the vial 210 increases. Consequently, in some configurations, the bag 260 contracts to a smaller volume to compensate for the volume of the returned fluid. As the bag 260 contracts, ambient air flows from the bag 260, through the bag aperture 264, through the regulator channel 225, and through the regulator aperture 250 to the surrounding environment, in some arrangements.

Thus, in certain embodiments, the adaptor 200 accommodates the withdrawal of fluid from, or the addition of fluid to, the vial 210 in order to maintain the pressure within the vial 210. In various instances, the pressure within the vial 210 changes no more than about 1 psi, no more than about 2 psi, no more than about 3 psi, no more than about 4 psi, or no more than about 5 psi.

As is evident from the embodiments and processes described above, the adaptor 200 advantageously allows a user to return unwanted liquid (and/or air) to the vial 210 without significantly increasing the pressure within the vial 210. As detailed earlier, the ability to inject air bubbles and excess fluid into the vial 210 is particularly desirable in the context of oncology drugs.

Furthermore, the above discussion demonstrates that certain embodiments of the adaptor 200 are configured to regulate the pressure within the vial 210 without introducing outside air into the vial 210. For example, in some embodiments, the bag 260 comprises a substantially impervious material that serves as a barrier, rather than a passageway, between the exterior and interior of the vial 210. Accordingly, such embodiments of the adaptor 200 substantially reduce the risk of introducing airborne contaminants into the bloodstream of a patient, as compared with the systems that employ imperfect and fault-prone Gortex® or Teflon® air filters. Furthermore, elimination of such filters eliminates the need for EtO sterilization. Consequently, more efficient and convenient forms of sterilization, such as gamma sterilization and electron beam sterilization, can be used to sterilize certain embodiments of the adaptor 200. Manufacturers can thereby benefit from the resulting cost savings and productivity increases. In some embodiments, filters can be used at one or more points between the bag 260 and the regulator aperture 250.

Advantageously, in certain embodiments, the bag 260 comprises an elastic material. Accordingly, as the bag 260 expands within the vial 210, a restorative force arises within the bag 260 that tends to contract the bag 260. In some instances the restorative force is fairly small, and can be balanced by a force within a syringe that is coupled to the adaptor 200. For example, the restorative force can be balanced by friction between the plunger and the interior wall of the syringe. Consequently, in some instances, the restorative force does not affect the withdrawal of an accurate amount of fluid from the vial 210. However, when the syringe is decoupled from the adaptor 200, the restorative force of the expanded bag 260 is no longer balanced. As a result, the bag 260 tends to contract, which encourages fluid within the extractor channel 245 to return to the vial 210. Accordingly, the adaptor 200 reduces the likelihood that fluid will spurt from the vial 210 when the syringe is decoupled therefrom, which is particularly beneficial when oncology drugs are being removed from the vial 210. When the adaptor 200 is used with the medical connector 241 (see FIG. 4), such as the Clave® connector, attached to the medical connector interface 240, the adaptor 200 can be substantially sealed in a rapid manner after removal of the syringe from the proximal end of the medical connector 240.

As noted above, in some instances the vial 210 is oriented with cap 214 pointing downward when liquid is removed from the vial 210. In certain advantageous embodiments, the extractor aperture 246 is located adjacent a bottom surface of the cap 214, thereby allowing removal of most or substantially all of the liquid in the vial 210. In other arrangements, the adaptor 200 comprises more than one extractor aperture 246 to aid in the removal of substantially all of the liquid in the vial 210. In some embodiments, the distal end 223 of the piercing member 220 is spaced away from the extractor aperture 246. Such arrangements advantageously allow fluid to flow through the extractor aperture 246 unobstructed as the distal portion 268 of the bag 260 expands.

Figure 8:
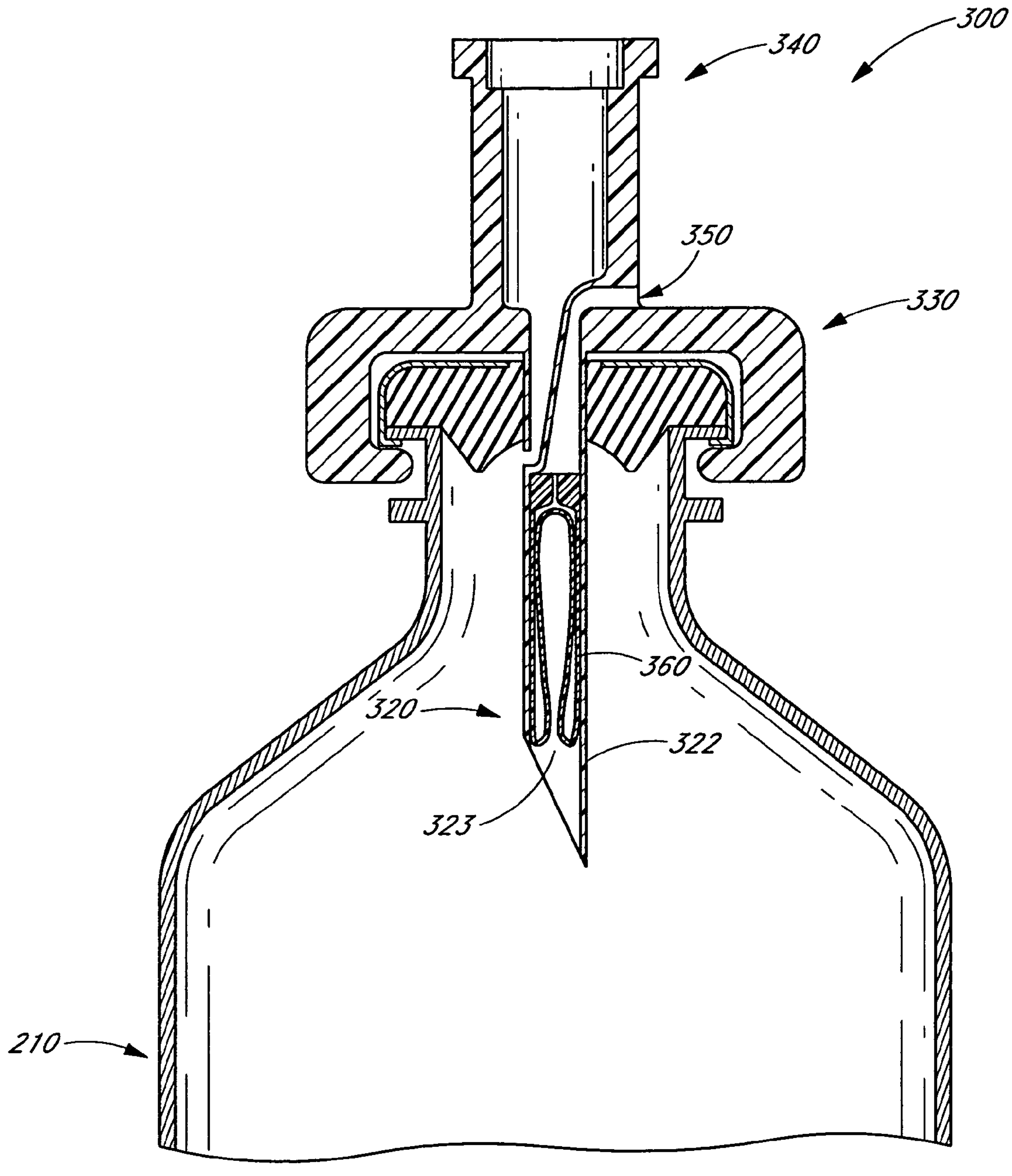
FIG. 8 is a partial cross-sectional view of a vial adaptor coupled with a vial.

FIG. 8 illustrates another embodiment of an adaptor 300. The adaptor 300 resembles the adaptor 200 discussed above in many respects. Accordingly, numerals used to identify features of the adaptor 200 are incremented by a factor of 100 to identify like features of the adaptor 300. This numbering convention applies to the remainder of the figures.

In certain embodiments, the adaptor 300 comprises a medical connector interface 340, a cap connector 330, a piercing member 320, and a bag 360. The piercing member comprises a sheath 322 having a distal end 323. The piercing member 320 differs from the piercing member 220 in that it does not comprise a separate tip. Rather, the distal end 323 is configured to pierce the septum 216. In the illustrated embodiment, the distal end 323 is angled from one side of the sheath 322 to another. Other configurations and structures are also possible. In many embodiments, the distal end 323 provides a substantially unobstructed path through which the bag 360 can be deployed. The distal end 323 preferably comprises rounded or beveled edges to prevent the bag 360 from ripping or tearing thereon. In some instances, the distal end 323 is sufficiently sharp to pierce the septum 216 when the adaptor 300 is coupled with the vial 210, but insufficiently sharp to pierce or damage the bag 360 when the bag 360 is deployed or expanded within the vial 210.

Figure 9:
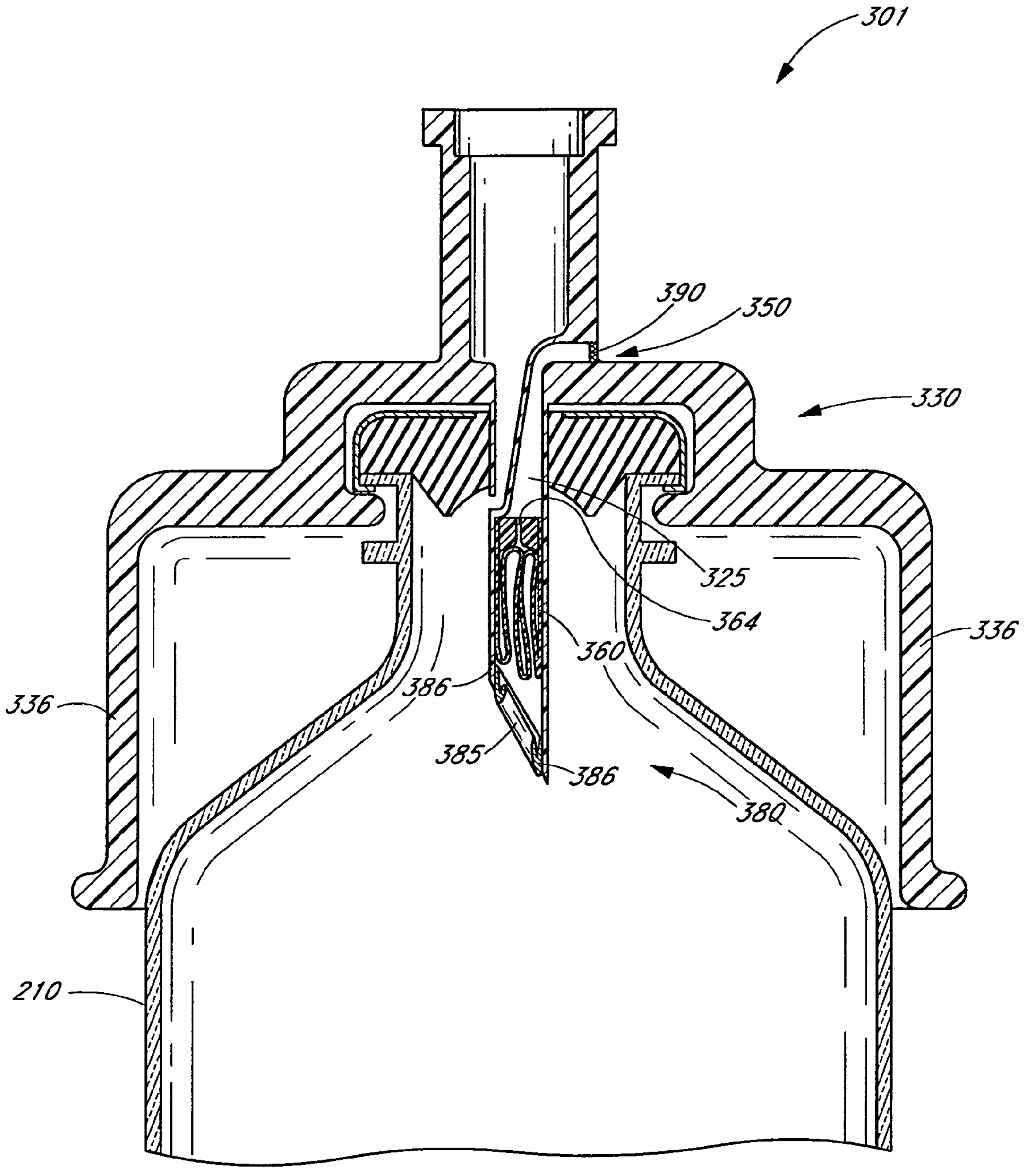
FIG. 9 is a partial cross-sectional view of a vial adaptor coupled with a vial.

FIG. 9 illustrates another embodiment of an adaptor 301 that is similar to the adaptor 300 in some respects, but differs in others such as those noted hereafter. The adaptor 301 comprises a piercing member 380 that substantially resembles the piercing member 320. In certain embodiments, however, the piercing member 380 is shorter than the piercing member 320, and thus does not extend as far into the vial 210. Accordingly, the piercing member 380 provides less of an obstruction to the bag 360 as it expands to fill (or partially fill) the vial 210. In further embodiments, the piercing member 380 comprises a bag 360 having multiple folds. The multiple folds allow the bag 360 to fit more compactly into the smaller volume of the piercing member 380 than is available in the piercing member 320.

In certain embodiments, the piercing member 380 comprises a flexible shield 385 extending around the periphery of a tip 386 of the piercing member 380. The shield can comprise, for example, plastic or rubber. The shield 385 can be adhered to an inner wall of the piercing member 380, or it can be tensioned in place. In certain embodiments, at least a portion of the shield 385 is inverted (as shown) when in a relaxed state. As the bag 360 is deployed, it forces a portion of the shield 385 outward from the tip 386. In some embodiments, the shield 385 is sized and dimensioned to extend to an outer surface of the tip 386 as the bag 360 expands. The shield 385 thus constitutes a barrier between the tip 386 and the bag 360 that protects the bag 360 from punctures, rips, or tears as the bag 360 expands.

In some arrangements, the adaptor 301 comprises a filter 390. In many embodiments, the filter 390 is associated with the regulator channel 325. The filter 390 can be located at the regulator aperture 350, within the regulator channel 325, or within the bag 360. For example, in some instances, the filter 390 extends across the regulator aperture 350, and in other instances, the filter 390 extends across the bag aperture 364. In some arrangements, the filter 390 is a hydrophobic filter which could prevent fluid from exiting the vial 210 in the unlikely event that the bag 360 ever ruptured during use. In such arrangements, air would be able to bypass the filter in proceeding into or out of the bag 360, but fluid passing through the ruptured bag 360 and through the regulator channel 325 would be stopped by the filter 390.

In the illustrated embodiment, the cap connector 330 of the adaptor 301 comprises a skirt 336 configured to encircle a portion of the vial 210. In some embodiments, the skirt 336 can extend around less than the entire circumference of the vial 210. For example, the skirt 336 can have a longitudinal slit. Advantageously, the skirt 336 can extend distally beyond the tip 386 of the piercing member 380. This configuration partially shields the tip 386 from users prior to insertion of the piercing member 380 into the vial 210, thereby helping to prevent accidental contact with the tip 386. The skirt 336 further provides a coupled adaptor 301 and vial 210 with a lower center of mass, thereby making the coupled items less likely to tip over.

Figure 10:
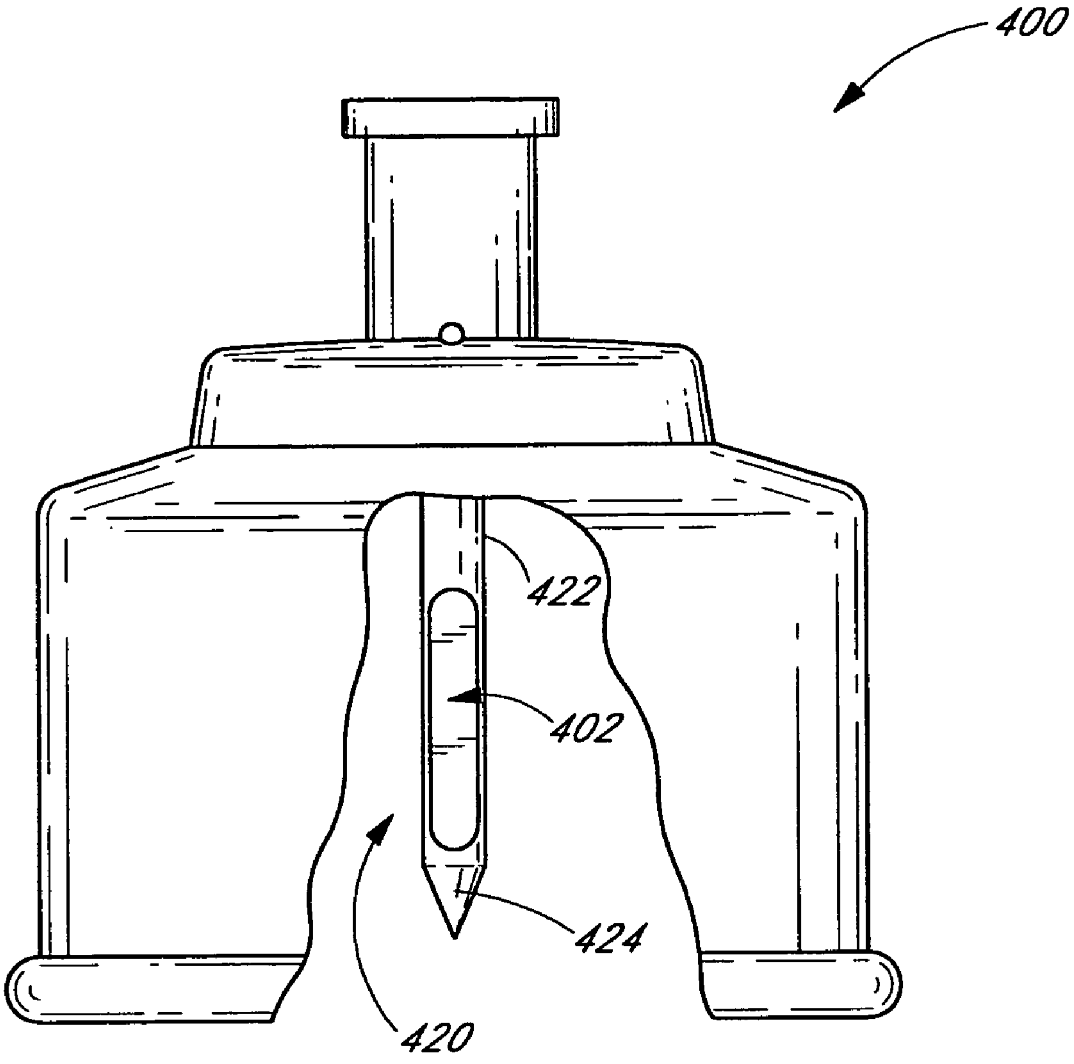
FIG. 10 is a cutaway perspective view of a vial adaptor.

FIG. 10 illustrates an embodiment of an adaptor 400 that resembles the adaptors 200, 300 described above in many ways, but comprises a piercing member 420 that differs from the piercing members 220, 320 in manners such as those now described. The piercing member 420 comprises a sheath 422, a tip 424, and a piercing member aperture 402. In certain embodiments, the tip 424 is substantially conical and comes to a point near an axial center of the piercing member 420. In some embodiments, the tip 424 is permanently attached to the sheath 422, and can be integrally formed therewith. The piercing member aperture 402 can be located proximal to the tip 424. The piercing member aperture 402 can assume a wide variety of shapes and sizes. In some configurations, it is desirable that a measurement of the piercing member aperture 402 in at least one direction (e.g., the longitudinal direction) have a measurement greater than the cross-sectional width of the piercing member 420 to facilitate the insertion of a bag 460 (shown in FIG. 11) through the aperture 402 during assembly of the adaptor 400. In some instances, the size and shape of the piercing member aperture 402 is optimized to allow a large portion of the bag 460 to pass therethrough when the bag 460 is deployed within the vial 210, while not compromising the structural integrity of the piercing member 420.

Figure 11:
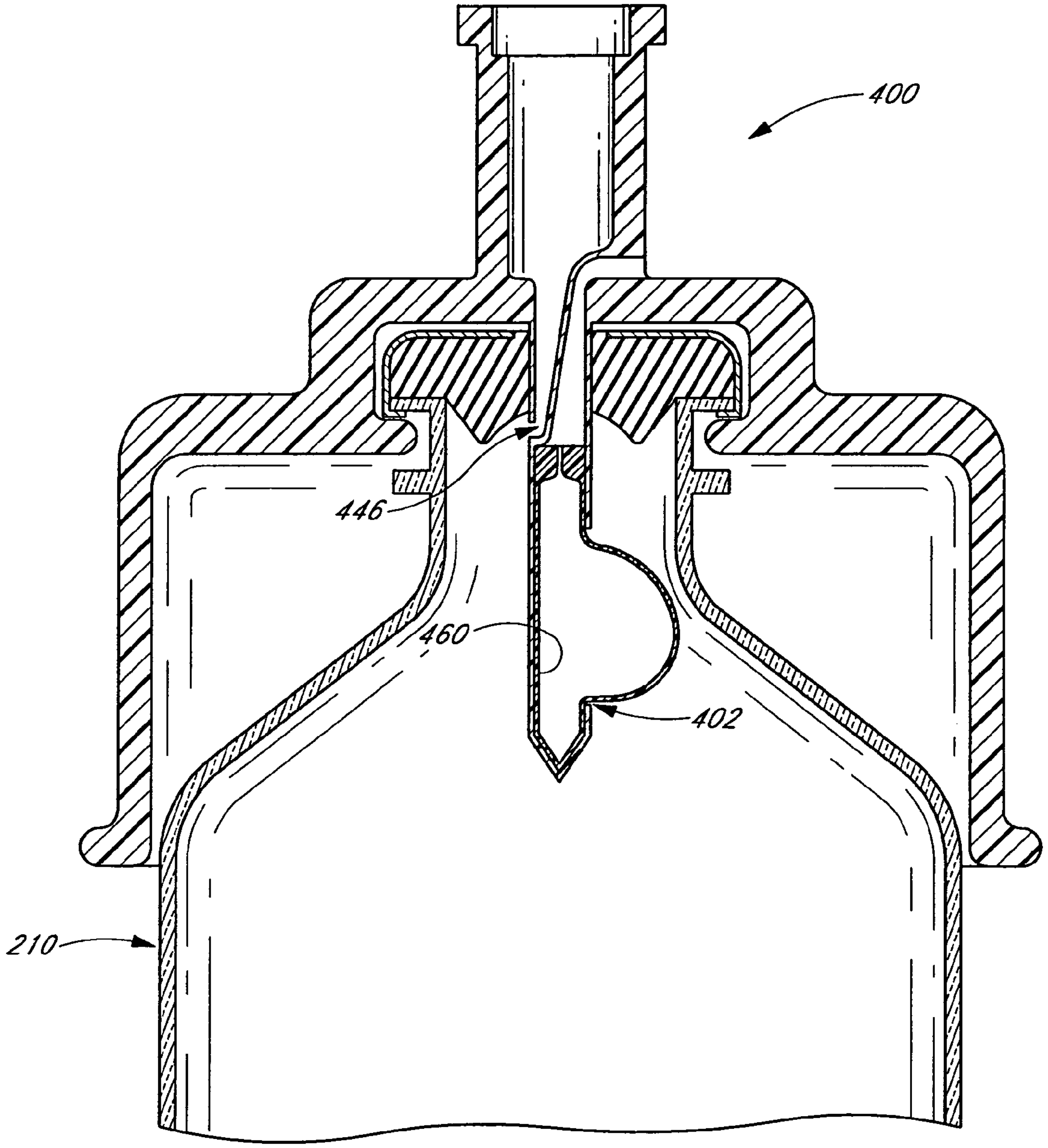
FIG. 11 is a partial cross-sectional view of a vial adaptor coupled with a vial.

FIG. 11 illustrates the adaptor 400 coupled with the vial 210. In the illustrated embodiment, the bag 460 is partially deployed within the vial 210. In certain embodiments, the bag 460 is configured to expand within the vial 210 and to fill a substantial portion thereof. As with the bag 260, the bag 460 can comprise an expandable material or a non-expandable material. In certain embodiments, the bag 460 comprises portions that are thicker near the piercing member aperture 402 in order to prevent rips or tears. In some instances, the piercing member aperture 402 comprises rounded or beveled edges for the same purpose.

As illustrated, in certain embodiments, the piercing member aperture 402 is located on a side of the piercing member 420 opposite an extractor aperture 446. Such arrangements can allow fluid to pass through the extractor aperture 446 unobstructed as the bag 460 expands within the vial 210.

FIGS. 12A-12D illustrate two embodiments of an adaptor 500. The adaptor 500 resembles the adaptors 200, 300 described above in many ways, but comprises a piercing member 520 that differs in manners such as those now described. In certain embodiments, the piercing member 520 comprises two or more sleeve members 503 that house a bag 560 (shown in FIGS. 12B and 12D). In certain arrangements, the sleeve members 503 meet at a proximal base 504 of the piercing member 520. As described more fully below, in some configurations, the sleeve members 503 are integrally formed from a unitary piece of material. In other configurations, the sleeve members 503 comprise separate pieces that are coupled with the proximal base 504.

Figure 12A:
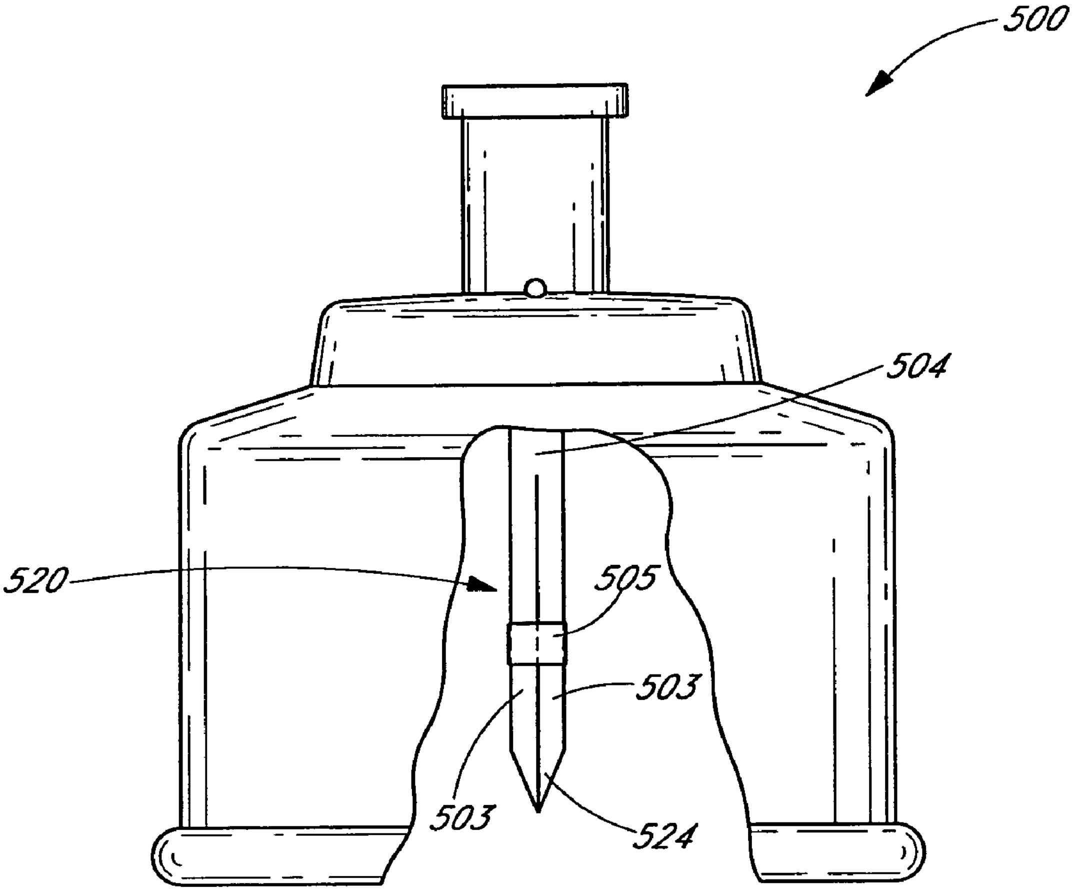
FIG. 12A is a cutaway perspective view of a vial adaptor.
Figure 12B:
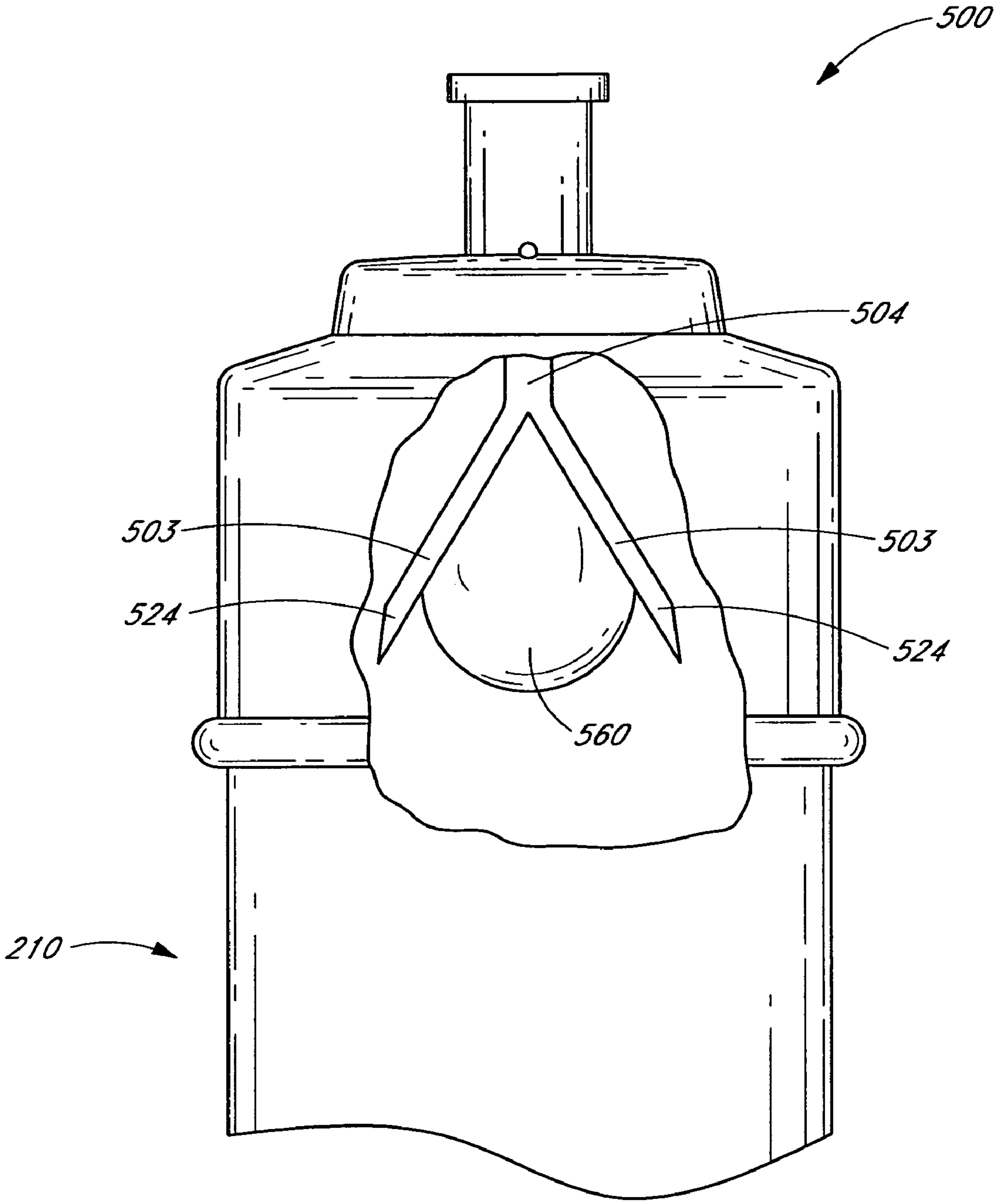
FIG. 12B is a partial cutaway perspective view of the vial adaptor of FIG. 12A coupled with a vial.

In certain embodiments, such as the embodiment illustrated in FIGS. 12A and 12B, the sleeve members 503 are biased toward an open configuration. In some instances, the bias is provided by the method used to create the sleeve members 503. For example, in some instances, two sleeve members 503 and the proximal base 504 are integrally formed from a unitary piece of pliable, molded plastic that substantially assumes a Y-shape, with each sleeve member 503 comprising one branch of the "Y." In other instances, the two sleeve members 503 comprise separate pieces that are coupled with the proximal base 504. In certain of such instances, the sleeve members 503 are pivotally mounted to or bendable with respect to the proximal base 504. The sleeve members 503 can be biased toward an open configuration by a spring or by any other suitable biasing device or method. While configurations employing two sleeve members 503 have been described for the sake of convenience, the piercing member 520 can comprise more than two sleeve members 503, and in various configurations, comprises three, four, five, six, seven, or eight sleeve members 503. In some instances, the number of sleeve members 503 of which the piercing member 520 is comprised increases with increasing size of the bag 560 and/or increasing size of the vial 210.

In some configurations, the bag 560 is inserted into the proximal base 504. As described above with respect to the bag 260, the bag 560 may be secured within the proximal base 504 by some form of adhesive, by a plastic sheath, via tension provided by a relatively thick proximal end of the bag 560, or by any other suitable method.

In many embodiments, after insertion of the bag 560 into the proximal base 504, the sleeve members 503 are brought together to form a tip 524. The tip 524 can assume any suitable shape for insertion through the septum 216 (not shown) of the vial 210. In some arrangements, a jacket 505 is provided around the sleeve members 503 to keep them in a closed configuration. The jacket 505 can be formed and then slid over the tip 524, or it may be wrapped around the sleeve members 503 and secured thereafter. The jacket 505 preferably comprises a material sufficiently strong to keep the sleeve members 503 in a closed configuration, yet capable of easily sliding along an exterior surface thereof when the piercing member 520 is inserted in the vial 210. In some instances, it is desirable that the material be capable of clinging to the septum 216. In various instances, the jacket 505 comprises heat shrink tubing, polyester, polyethylene, polypropylene, saran, latex rubber, polyisoprene, silicone rubber, or polyurethane. The jacket 505 can be located anywhere along the length of the piercing member 520. In some embodiments, it can be advantageous to position the jacket 505 on the distal portion of the sleeve members 503 to maintain the sleeve members 503 close together to provide a sharp point for piercing the septum 216.

FIG. 12B illustrates an embodiment of the adaptor 500 having sleeve members biased toward an open position coupled with the vial 210. In certain embodiments, as the piercing member 520 is inserted into the vial 210, the jacket 505 catches on the septum 216 and remains on the exterior of the vial 210. As the piercing member 520 continues through the septum 216, the sleeve members 503 return to their naturally open state, thus deploying the bag 560 within the vial 210. As fluid is withdrawn from the vial 210, the bag 560 expands within the vial 210 in a manner such as that described above with respect to the bag 260.

Figure 12C:
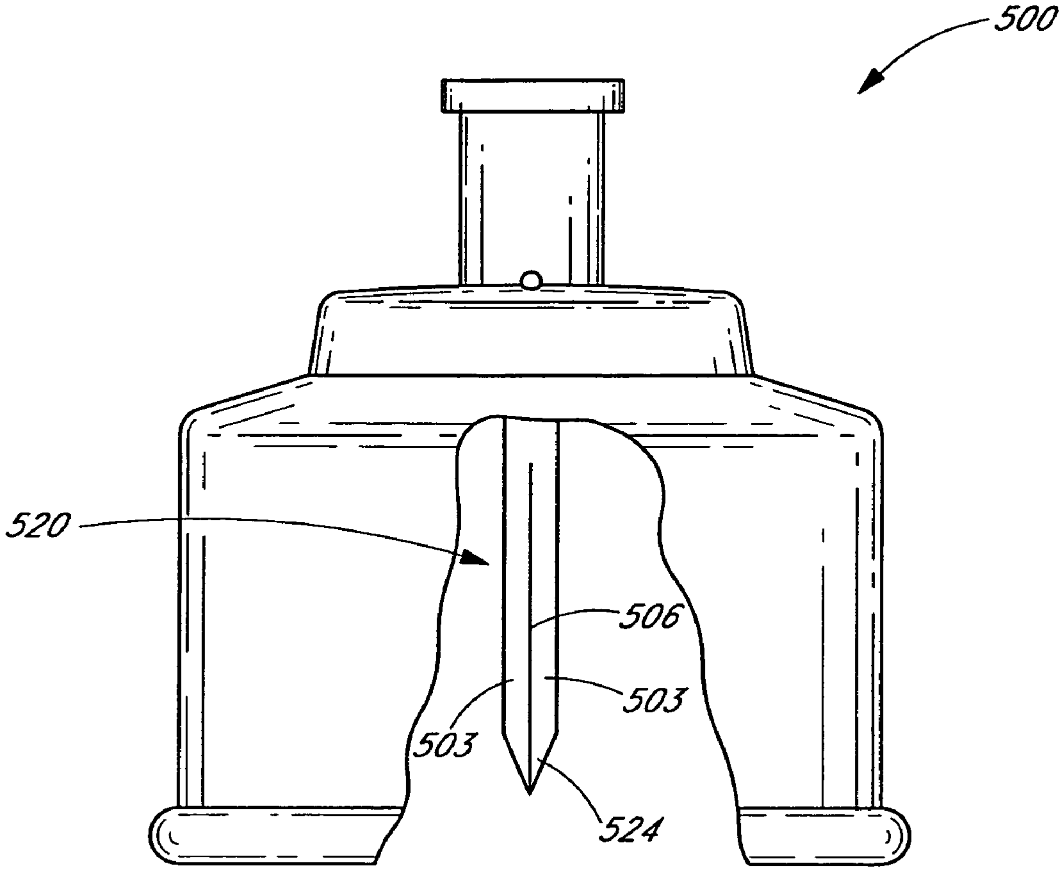
FIG. 12C is a cutaway perspective view of a vial adaptor.
Figure 12D:
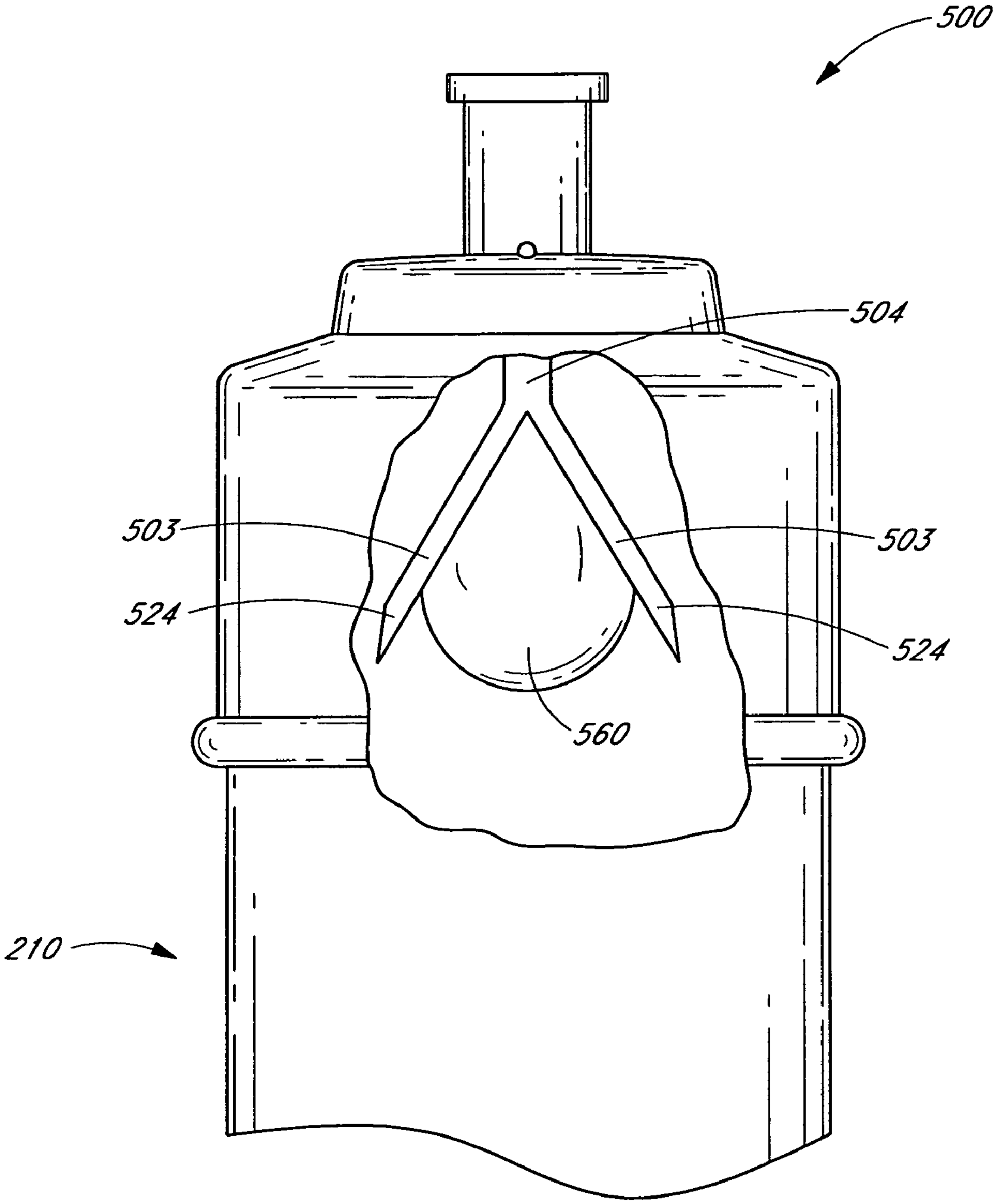
FIG. 12D is a partial cutaway perspective view of the vial adaptor of FIG. 12C coupled with a vial.

In certain embodiments, such as the embodiment illustrated in FIGS. 12C and 12D, the sleeve members 503 are biased toward a closed configuration. In some instances, the bias is provided by the method used to create the sleeve members 503. For example, the sleeve members 503 and the proximal base 504 can be integrally formed from a unitary piece of molded plastic. During the molding process, or sometime thereafter, one or more slits 506 are formed in the molded plastic, thereby separating the sleeve members 503. In other instances the sleeve members 503 comprise separate pieces that are attached to the proximal base 504. In certain of such instances, the sleeve members 503 are pivotally mounted to the proximal base. The sleeve members 503 can be biased toward a closed configuration by a spring or by any other suitable biasing device.

In some configurations, the sleeve members 503 are opened to allow the insertion of the bag 560 into the piercing member 520. The sleeve members 503 return to their naturally closed state after insertion of the bag 560. As described above, the bag 560 can be secured within the proximal base 504 by any of numerous methods.

FIG. 12D illustrates an embodiment of the adaptor 500 having sleeve members biased toward a closed position coupled with the vial 210. In certain embodiments, the piercing member 520 is inserted into the vial 210. As fluid is withdrawn from the vial 210, unbalanced pressure between the interior of the bag 560 and the interior of the vial 210 causes the bag 560 to expand within the vial 210, thereby forcing open the sleeve members 503. The bag 560 can continue to expand and further separate the sleeve members 503.

Figure 13:
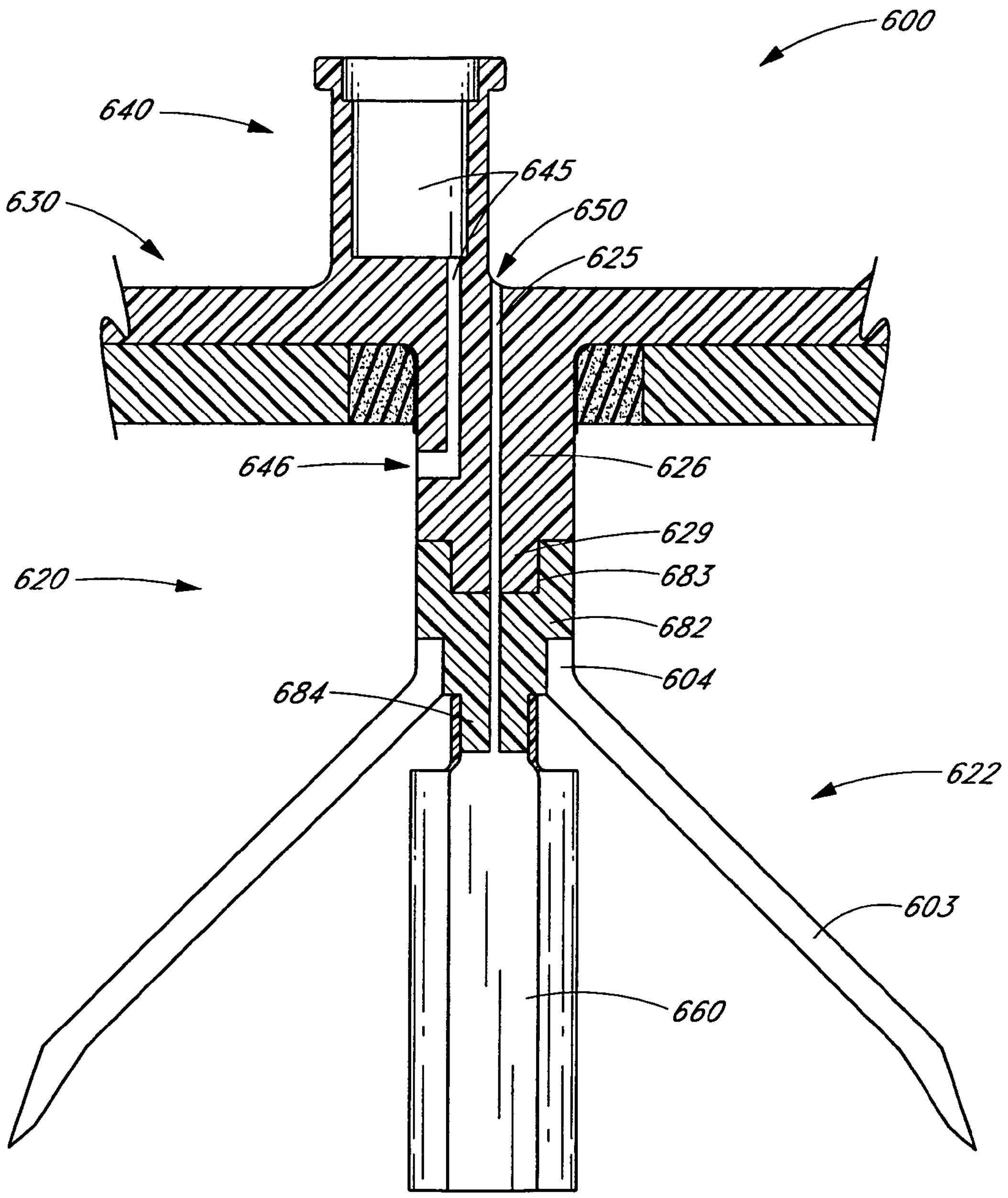
FIG. 13 is a partial cross-sectional view of a vial adaptor coupled with a vial.

FIG. 13 illustrates an embodiment of an adaptor 600 comprising a plurality of sleeve members 603. The adaptor 600 resembles the adaptors 200, 300, 500 described above in many ways, but differs in manners such as those now described. In certain embodiments, the adaptor 600 comprises a medical connector interface 640, a cap connector 630, and a piercing member 620. In some embodiments, the piercing member 620 comprises a projection 626, a bag connector 682, a sleeve 622, and a bag 660. In some configurations, the interface 640, the cap connector 630, and the projection 626 are integrally formed of a unitary piece of material, such as polycarbonate plastic. In certain of such configurations, the bag connector 682 is also integrally formed therewith.

In certain embodiments, the bag connector 682 is attached to the projection 626, preferably in substantially airtight engagement. In some embodiments, the bag connector 682 comprises a chamber 683 configured to accept a distal extension 629 of the projection 626. In the illustrated embodiment, the bag connector 682 and chamber 683 define complimentary cylinders. A portion of the chamber 683, preferably a sidewall thereof, can be adhered to the distal extension 629 by glue, epoxy, or other suitable means. A variety of other configurations for joining the bag connector 682 and proximal portion 626 can be employed.

Figure 14:
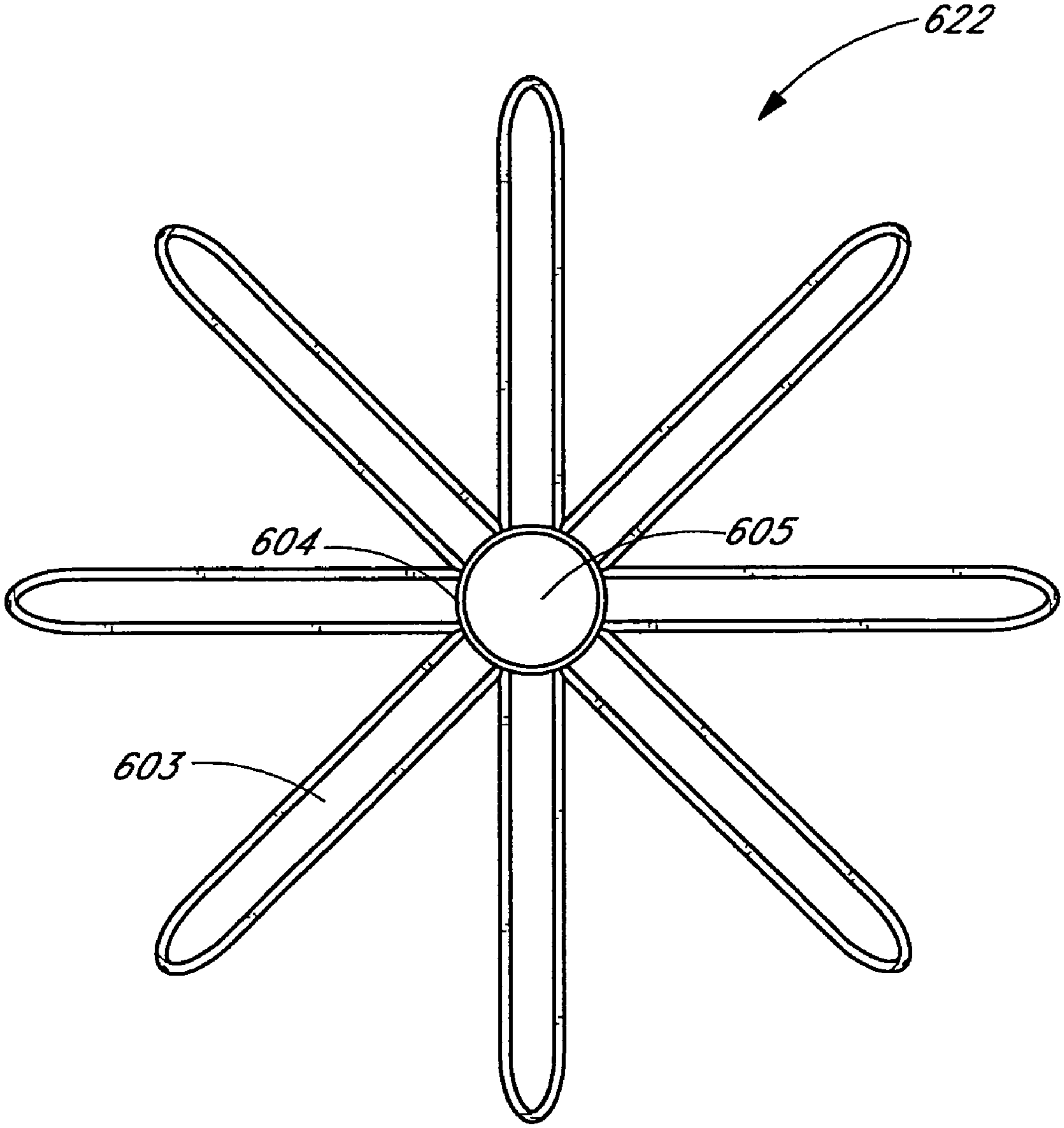
FIG. 14 is a bottom plan view of a sleeve comprising multiple sleeve members.

In some arrangements, the bag connector 682 is also attached to the sleeve 622. As illustrated in FIG. 14, in some arrangements, the sleeve 622 comprises a proximal base 604 from which a plurality of sleeve members 603 extend. In some instances, the proximal base 604 can define an opening 605. In various configurations, the sleeve 622 comprises two, three, four, five, six, seven, or eight sleeve members 603. More sleeve members 603 are also possible. The sleeve members 603 can cooperate to form a cavity for housing the bag 660.

With reference again to FIG. 13, a portion of the bag connector 682 can be inserted through the opening 605 of the proximal base 604. The connector 682 and proximal base 604 can be adhered to each other in some instances, and can be secured to each other by a friction fit in others. Other methods of attachment are also possible. In many instances, the proximal base 604 remains fixed while the sleeve members 603 are allowed to move. The sleeve members 603 resemble the sleeve members 503 described above, and can thus be biased toward an open configuration or a closed configuration. Accordingly, in some arrangements, a jacket (not shown) is used to retain sleeve members 603 that are biased toward an open configuration in a closed configuration until the piercing member 620 is inserted through the septum 216. In some instances, the jacket is trapped between the septum 216 and an interior surface of the cap connector 630, thereby helping to form a substantially airtight seal between the adaptor 600 and the vial 210.

In the illustrated embodiment, the bag connector 682 defines a portion of a regulator channel 625, which also extends through the projection 626 of the piercing member 620, the cap connector 630, and a regulator aperture 650. An extractor channel 645 extends from an extractor aperture 646 and through the proximal portion 626, the cap connector 630, and the medical connector interface 640. In certain embodiments, the extractor aperture 646 is spaced away from the bag 660.

In some instances, the bag connector 682 comprises a nozzle 684 to which the bag 660 can be coupled. FIGS. 15A and 15B illustrate two embodiments of the nozzle 684. In the embodiment illustrated in FIG. 15A, the nozzle 684 is inserted into a proximal end 662 of the bag 660. The bag 660 can be coupled to the nozzle 684 by any suitable means, such as by an adhesive, a plastic sleeve, a heat seal, or a tension fit. As describe above with respect to the bag 360, in certain embodiments, a substantially airtight tension fit is achieved when the proximal end 662 of the bag 660 is sufficiently thick and stiff.

In the embodiment illustrated in FIG. 15B, the nozzle 684 comprises one or more clip extensions 685. In some embodiments, a single clip extension 685 encircles the nozzle 684. Each of the one or more clip extensions 685 comprises a detent 686 and defines a recess 687. In certain embodiments, a collar 688 is placed around the proximal end 662 of the bag 660. The collar 688 is preferably sized and configured to fit snugly within the recess 687 and to be held securely in place by the detent 686 of each clip extension 685. Consequently, the one or more clip extensions 685 in cooperation with the collar 688 form a substantially airtight seal between the proximal end 662 of the bag 660 and the nozzle 684.

With reference again to FIG. 15A, in certain embodiments, the bag 660 is substantially cylindrical. In some embodiments, the walls of the bag 660 are thicker than the base thereof. In certain embodiments, the walls of the bag 660 are between about 0.001 inches and 0.004 inches, between about 0.001 inches and about 0.002 inches, between about 0.002 inches and about 0.003 inches, or between about 0.003 inches and about 0.004 inches thick. In other arrangements, the walls are greater than 0.001 inches, greater than 0.002 inches, or greater than 0.003 inches thick. In still other arrangements, the walls are less than about 0.004 inches, less than about 0.003 inches, or less than about 0.002 inches thick. Cylindrical configurations can be advantageous for use with the vial 210 when a large portion the vial 210 is generally cylindrical, as is often the case with standard medicinal vials. The cylindrical bag 660 can expand to a shape that substantially conforms to the interior volume of the vial 210.

Figure 16:
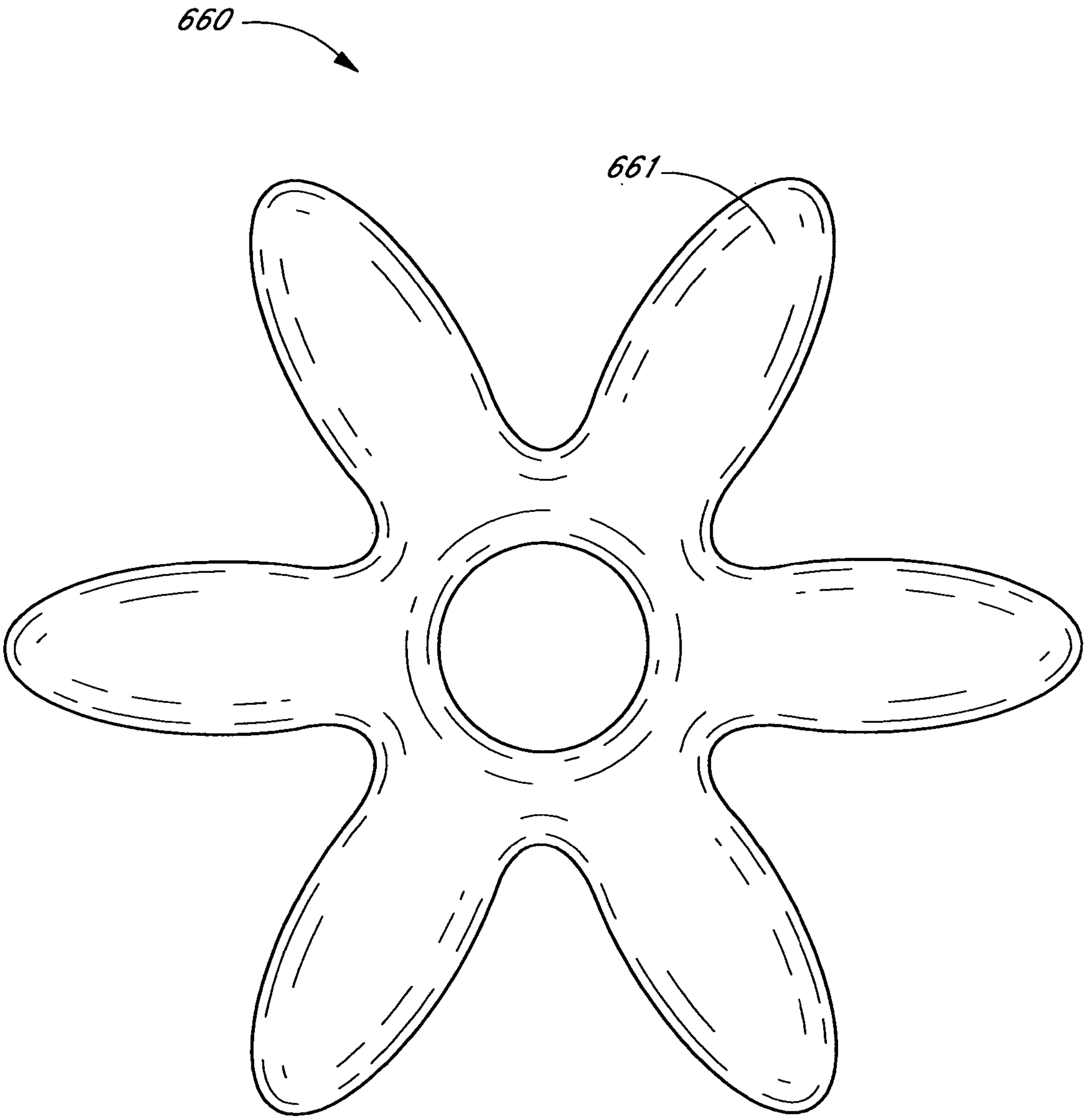
FIG. 16 is a top plan view of a folded bag.

As illustrated in FIG. 16, in some instances, the bag 660 can be folded in a star-like configuration having multiple arms 661. Each arm 661 can be folded, rolled, crumpled, or otherwise manipulated to fit within the piercing member 620 when it is closed. Any number of arms 661 can be formed from the bag 660, and in certain instances, the number of arms 661 increases with increasingly larger bags 660. In other configurations, the bag 660 is molded or shaped such that it naturally has a star-shaped cross-section and is capable of expanding to fill substantially cylindrical vials 210. Other configurations of the bag 660 are also possible, as discussed above in connection with the bag 260, and similar folding patterns may be employed.

Figure 17:
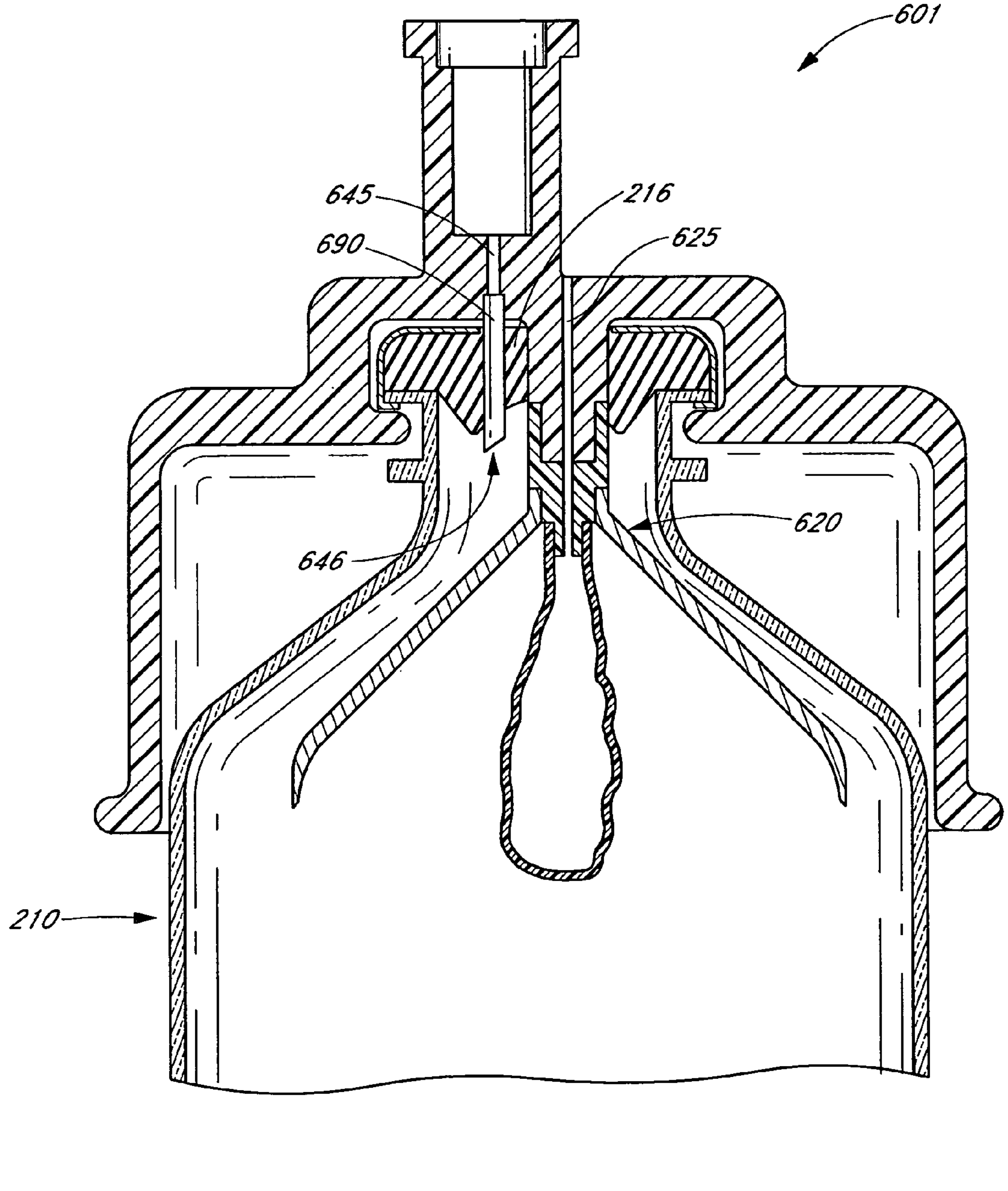
FIG. 17 is a partial cross-sectional view of a vial adaptor coupled with a vial.

FIG. 17 illustrates an embodiment of an adaptor 601 that resembles the adaptor 600 in many ways, but differs in manners such as those now described. The adaptor 601 comprises the piercing member 620 that partially defines the regulator channel 625, and further comprises a secondary piercing member 690 that partially defines the extractor channel 645. Accordingly, the adaptor 601 punctures the septum 216 in two distinct locations when coupled with the vial 210.

The secondary piercing member 690 can comprise any suitable material for puncturing the septum 216. In various embodiments, the secondary piercing member 690 comprises metal or plastic. In many configurations, the secondary piercing member 690 is significantly smaller than the piercing member 620, which allows both piercing members 620, 690 to be readily inserted through the septum 216. Furthermore, a smaller secondary piercing member 690 can position the extractor aperture 646, which is located at the tip of the secondary piercing member 690 in some configurations, adjacent an interior surface of the septum 216 when the adaptor 601 is coupled to the vial 210. Accordingly, most of the liquid contents of the vial 210 may be removed when the vial 210 is turned upside-down.

Figure 18:
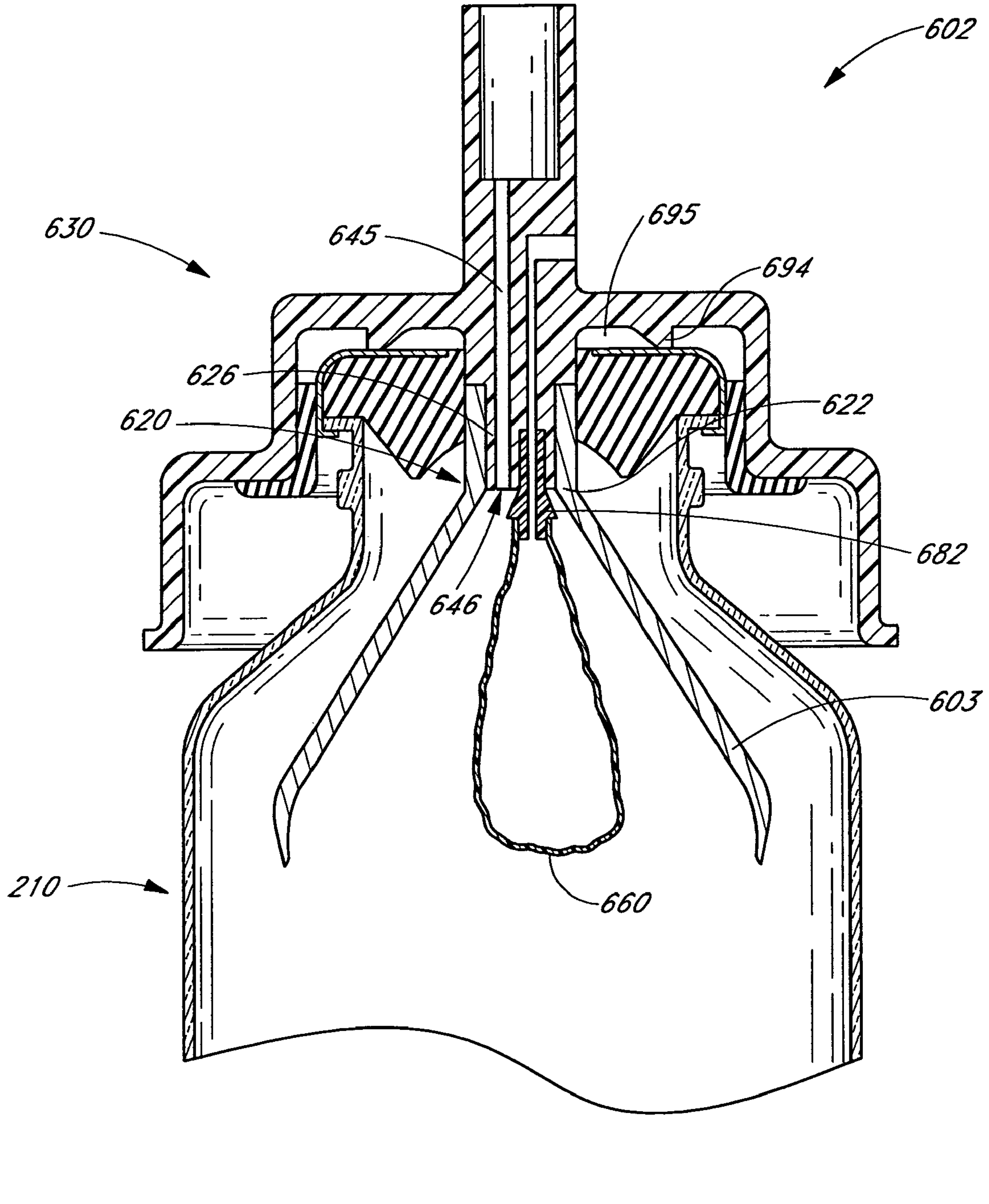
FIG. 18 is a partial cross-sectional view of a vial adaptor coupled with a vial.

FIG. 18 illustrates an embodiment of an adaptor 602 that resembles the adaptor 600 in many ways, but differs in manners such as those now described. In the illustrated embodiment, the extractor channel 645 extends through the proximal portion 626 of the piercing member 620 such that the extractor aperture 646 is located within, or at a position interior to an outer surface of, the sleeve 622. More generally, the extractor aperture 646 is located within, or at a position interior to an outer surface of, the piercing member 620. In certain embodiments, as shown, the bag connector 682 is configured to space the bag 660 away from the extractor aperture 646 so that fluid may flow through the aperture 646 unobstructed as the bag 660 expands.

In certain embodiments, a ridge 694 extends around an inner surface of the cap connector 630 and defines a space 695 for accepting a jacket (not shown) used to keep the sleeve members 603 in a closed configuration. The space 695 can be of particular utility when the jacket has a substantial length or otherwise comprises a large amount of material.

Figure 19:
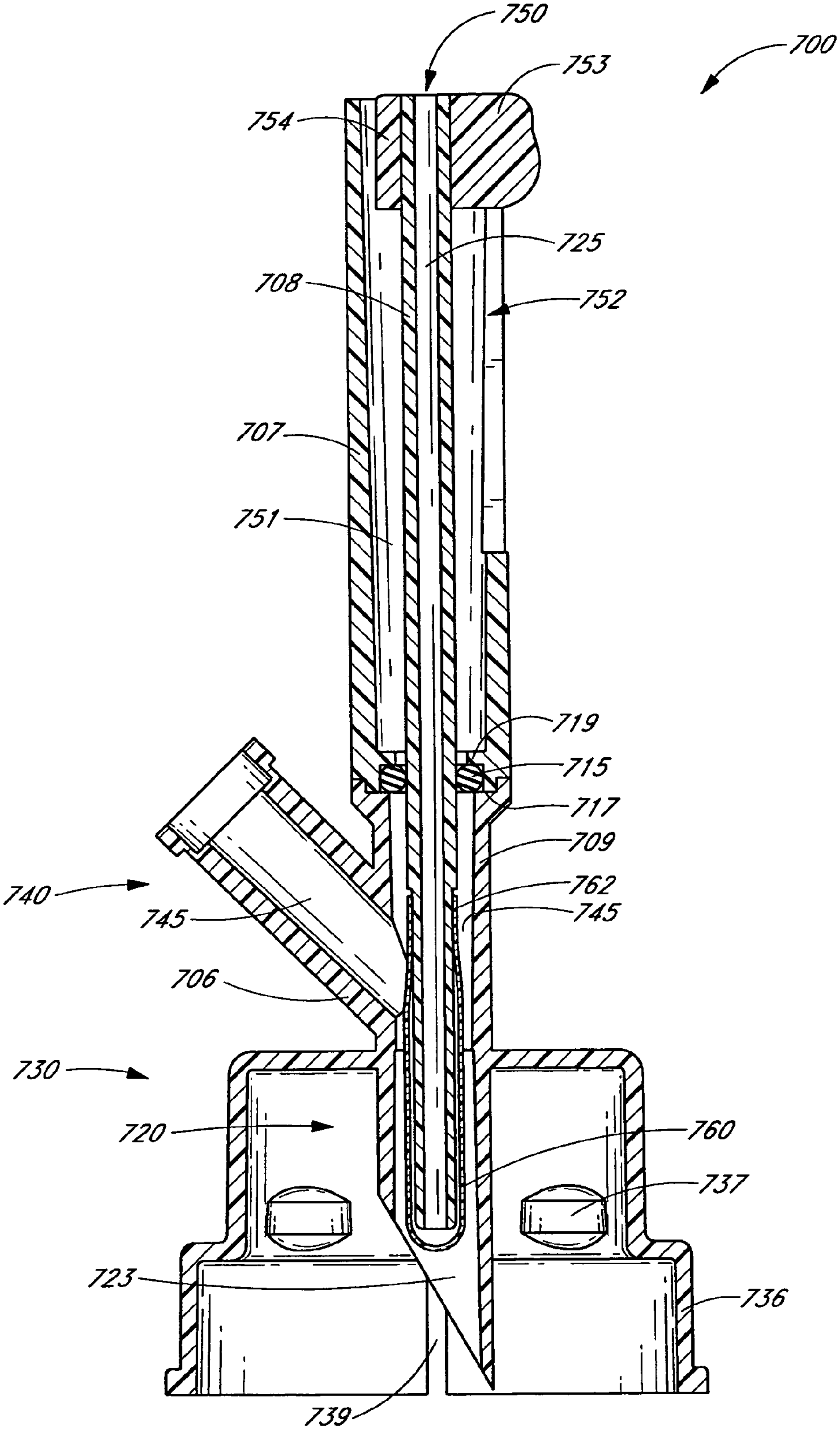
FIG. 19 is a cross-sectional view of a vial adaptor.

FIG. 19 illustrates an embodiment of a vial adaptor 700. In certain embodiments, the adaptor 700 comprises a housing member 706, a sheath 707, and a bag insertion member 708. In some embodiments, the housing member 706 comprises a piercing member 720, a cap connector 730, and a medical connector interface 740 that in some ways resemble similarly numbered features of various other adaptor embodiments described herein.

In certain embodiments, the medical connector interface 740 branches from a proximal extension 709 of the housing member 706. The medical connector interface 740 defines a branch of a substantially "y"-shaped extractor channel 745. The piercing member 720 and the proximal extension 709 define the remainder of the extractor channel 745.

In certain embodiments, the cap connector 730 comprises one or more projections 737 for securing the adaptor 700 to the cap 214 of the vial 210 (not shown). In some embodiments, the cap connector 730 comprises one or more slits 739 that facilitate the coupling of the adaptor 700 to the vial 210 by allowing the cap connector 730 to expand. In some configurations, the cap connector 730 comprises a skirt 736.

The piercing member 720 can resemble the piercing members described herein. In some embodiments, the piercing member 720 comprises an angled distal end 723 which allows the passage therethrough of the bag insertion member 708. Advantageously, in some embodiments, the piercing member

720 is configured to extend only a short distance into the vial 210. Accordingly, a large amount of fluid can be withdrawn from the vial 210 when the vial 210 is oriented with the cap 214 facing downward. By being shorter, the piercing member 720 can also have thinner walls without the risk of bending or breaking upon insertion into the vial 210. Thinner walls can allow the insertion of a larger bag 760 than would otherwise be possible, thus permitting the safe and accurate withdrawal of a larger amount of fluid from the vial 210 in some instances. In some embodiments, the piercing member 720 does not extend beyond the skirt 736, which helps to shield users from accidental contact with the piercing member 720.

In some embodiments, the proximal extension 709 of the housing member 706 is coupled with the sheath 707. In certain instances, the proximal extension 709 and the housing member 706 are joined in threaded, snapped, or friction-fit engagement. In some instances, the proximal extension 709 and the housing member 706 are joined by glue, epoxy, ultrasonic welding, etc. In further arrangements, the proximal extension 709 and the housing member 706 are integrally formed of a unitary piece of material. In some arrangements, the proximal extension 709 and the housing member 706 are coupled in substantially airtight engagement.

In some embodiments, the proximal extension 709 and the sheath 707 are configured to secure a sealing member 715 in place. In some configurations, the proximal extension 709 comprises a shelf 717 that extends around an inner perimeter thereof, and the sheath 707 comprises ridge 719 that extends around an inner perimeter thereof. The shelf 717 and the ridge 719 can be configured to tension the sealing member 715 in place. In some arrangements, the sealing member 715 is slightly compressed by the shelf 717 and the ridge 719. In further arrangements, the sealing member 715 is held in place by glue or some other adhesive. In other embodiments, the sealing member 715 is retained in a groove in the bag insertion member 708.

The sealing member 715 can comprise any suitable material for forming a substantially airtight seal with the bag insertion member 708 while being slidably engaged therewith. In some instances, the sealing member 715 comprises a standard O-ring as is known in the art. In other instances, the sealing member 715 comprises a flange or other configuration that permits movement of the bag insertion member 708 in one direction only, such as to be inserted in the vial 210. In some instances, the substantially airtight seal between the sealing member 715 and the bag insertion member 708 defines a proximal boundary of the extractor channel 745.

In certain embodiments, the sheath 707 is sized and dimensioned to be gripped by a user—in various instances, with one, two, three, or four fingers of one hand of the user. The sheath 707 can be substantially hollow, defining a chamber 751 through which the bag insertion member 708 can move. In some embodiments, the chamber 751 narrows toward the distal end thereof. The sheath 707 can also define a slot 752. In some instances, the slot 752 has a substantially constant width, while in others, the slot 752 narrows toward a distal end thereof. The slot 752 can comprise a locking mechanism, as described below.

In various arrangements, a tab 753 is attached to or integrally formed with the bag insertion member 708. The tab 753 can be sized and dimensioned to be easily manipulated by a user—in some instances, by a thumb of the user. The tab 753 can be rounded to prevent any snags thereon by gloves that might be worn by the user. The tab 753 is generally configured to cooperate with the slot 752. In some arrangements, the tab 753 extends radially outward from the proximal end of the bag insertion member 753 and through the slot 752. The tab 753 and the slot 752 can be sized and configured such that the tab 753 can slide along a length of the slot 752. In some arrangements, the distal end of the slot 752 is sized such that the tab 753 fits snugly therein.

Figure 20A:
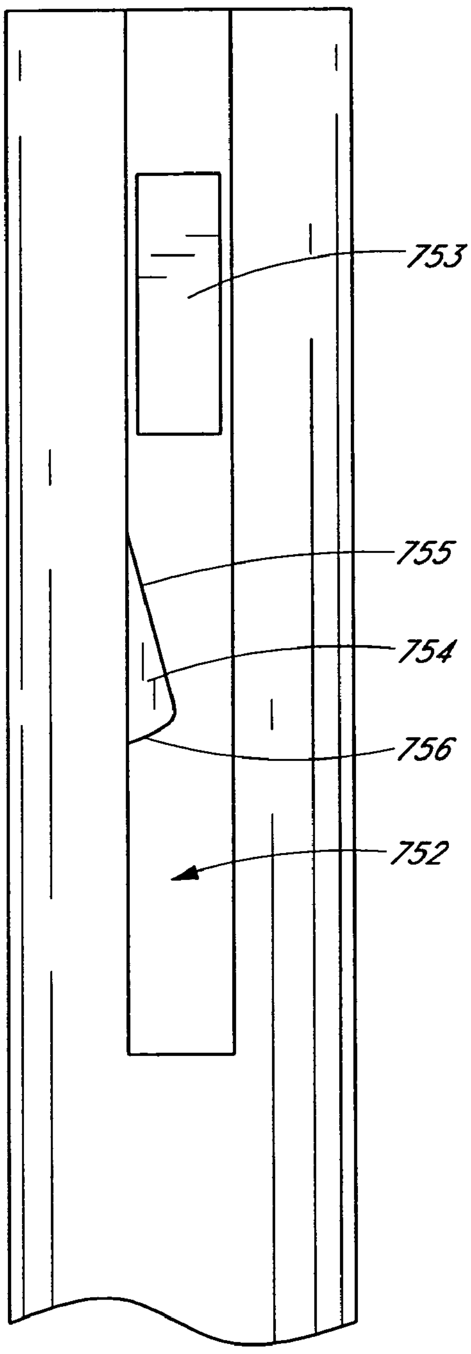
FIG. 20A is a partial front plan view of a tab locking mechanism for a vial adaptor.
Figure 20B:
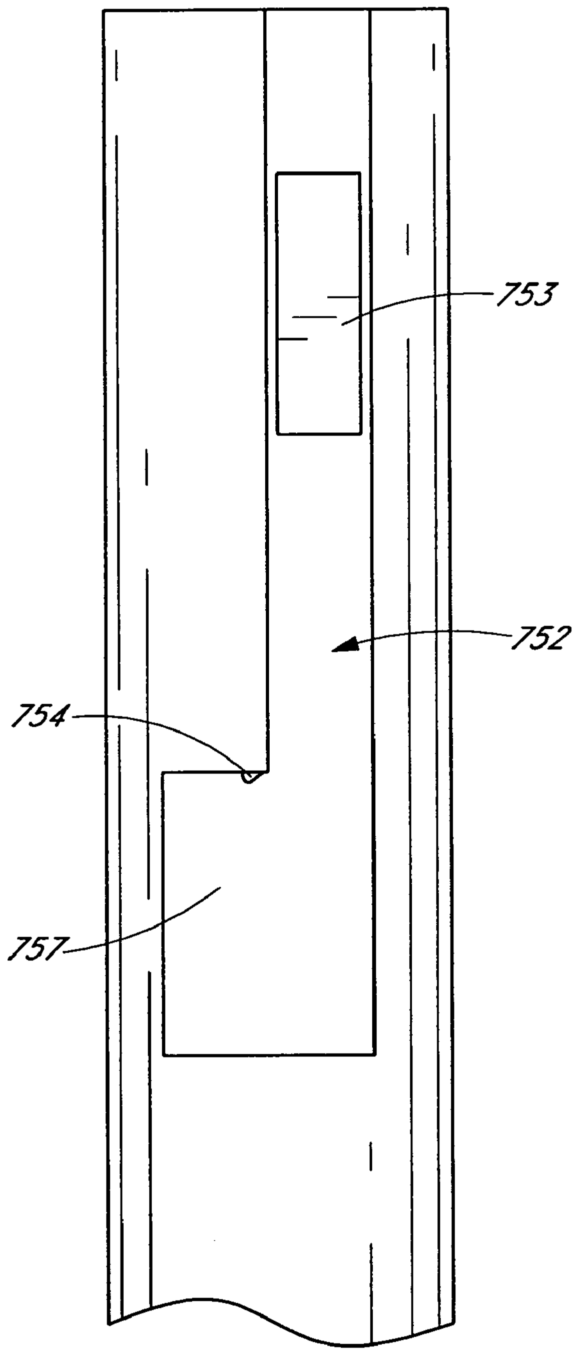
FIG. 20B is a partial front plan view of a tab locking mechanism for a vial adaptor.

FIGS. 20A and 20B illustrate two separate locking mechanisms that can be used to secure the tab 753 at some fixed position in the slot 752. FIG. 20A illustrates a clip 754. The clip 754 comprises an angled face 755 and a ridge 756, and is biased toward a closed position, as illustrated. As the tab 753 is advanced toward the distal end of the slot 752, it contacts the face 755 and forces the clip 754 toward an open position. Once the tab 753 has been advanced to the distal end of the slot 752, the clip 754 is free to return to its natural, closed position. Accordingly, the ridge 756 contacts a proximal surface of the tab 753 and holds the tab 753 in place. As shown, in some arrangements, the ridge 756 is curved such that the clip 754 will not spring back into place until the tab 753 has reached the distal end of the slot 752, and once the clip 754 does spring back into place, a portion of the ridge 756 remains in contact with the clip 754. In other arrangements, more than one clip 754 can be used. For example, one clip 754 can be located on each side of the slot 752 to provide greater stability to the tab 753 when locked in place. In other instances, the one or more clips 754 comprise ridges extending from the sides of the slot 752 and are integrally formed with the sheath 707. In such instances, the clips 754 can be substantially smaller than those shown, and need not move independently from the sheath 707.

FIG. 20B illustrates an alternative arrangement of the slot 752 that can provide a locking mechanism for the tab 753. In the illustrated embodiment, the slot 752 comprises a lateral extension 757 that has a height corresponding to the height of the tab 753. Accordingly, once the tab 753 is advanced to the distal end of the slot 752, the tab 753 can be rotated into the lateral extension 757. In some instances, the tab 753 is secured in the lateral extension 757 by a friction fit. In other instances, a clip 754 can be used. Any other suitable means for locking the tab 753 in place can be employed.

With reference again to FIG. 19, in certain embodiments, the bag insertion member 708 comprises a flange 754 configured to help securely lock the tab 753 in place. The flange 754 can be attached to or integrally formed with the bag insertion member 708, and in certain instances, comprises a unitary piece with the tab 753. As noted above, in certain arrangements, the chamber 751 narrows toward the distal end of the sheath 707. Accordingly, as the bag insertion member 708 is advanced toward the distal end of the sheath 707, the flange 754 contacts a sidewall of the chamber 751, thereby restricting movement of the proximal end of the bag insertion member 708.

In certain embodiments, the bag insertion member 708 comprises a hollow shaft 753. In some arrangements, the shaft 753 extends from a proximal end of the sheath 707 to the distal end 723 of the piercing member 720. The shaft 753 can define a regulator channel 725 through which ambient air may flow.

In some arrangements, the bag insertion member 708 comprises thinner walls at its distal end to allow room for the bag 760 within the extractor channel 745. The bag 760 can be attached to the bag insertion member 708 by any suitable means, such as those described above with respect to the bag 260. In some arrangements, only the distal end 762 of the bag 760 is attached to the bag insertion member 708, thus freeing the remainder of the bag 760 to expand within the vial 210. In some instances, the bag 760 is substantially cylindrical in order to conform to the volume of the vial 210. The bag 760 can be configured to expand both laterally and longitudinally.

In certain arrangements, the bag insertion member 708 is configured to advance the bag 760 to a distance within the vial 210 sufficient to ensure that the bag 760 does not obstruct fluid flow through the distal end 723 of the piercing member 720. As indicated above, in some embodiments, the bag insertion member 708 is locked in place once it is advanced into the vial 210. Because the bag insertion member 708 generally cannot thereafter be withdrawn from the vial 210, there is a reduced chance of puncturing or tearing the bag 760 on the distal tip 723 after the bag 760 has expanded laterally.

Certain processes for using the adaptor 700 resemble those described above with respect to the adaptor 200 in many ways, and can include additional or alternative procedures such as those now described. In certain instances, once the adaptor 700 is coupled with the vial 210, the tab 753 is advanced distally along the slot 752, thus advancing the bag 760 toward the interior of the vial 210. In some instances, the tab 753 is locked in place at the distal end of the slot 752. In some instances, a user grips the sheath 707 with one or more fingers of one hand and advances the tab 753 distally within the slot 752 with the thumb of the hand until the tab 753 locks in place. Other gripping arrangements can also be employed.

In some instances, fluid is withdrawn from the vial 210 through the distal end 723 and through the extractor channel 745, and the bag 760 consequently expands with air. The air can flow through a regulator aperture 750, through the regulator channel 725 and into the bag 760. In other instances, fluid is injected into the vial 210 via the extractor channel 745 and the distal end 723, and air is forced from the bag 760. The expelled air can follow the reverse path through the regulator channel 725.

Figure 21:
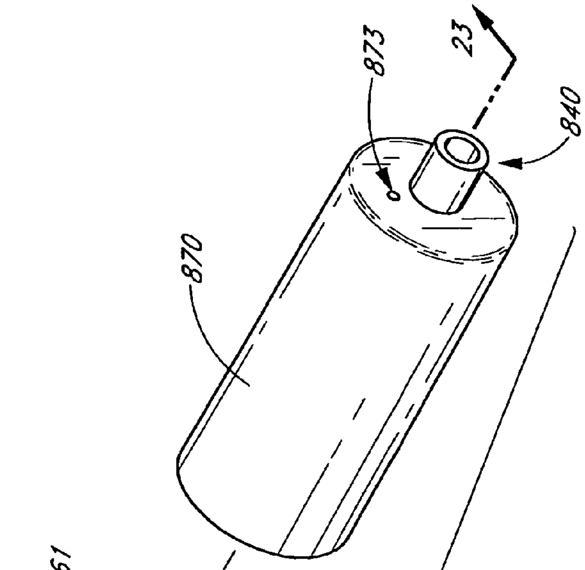
FIG. 21 is an exploded perspective view of a vial adaptor.
Figure 21:
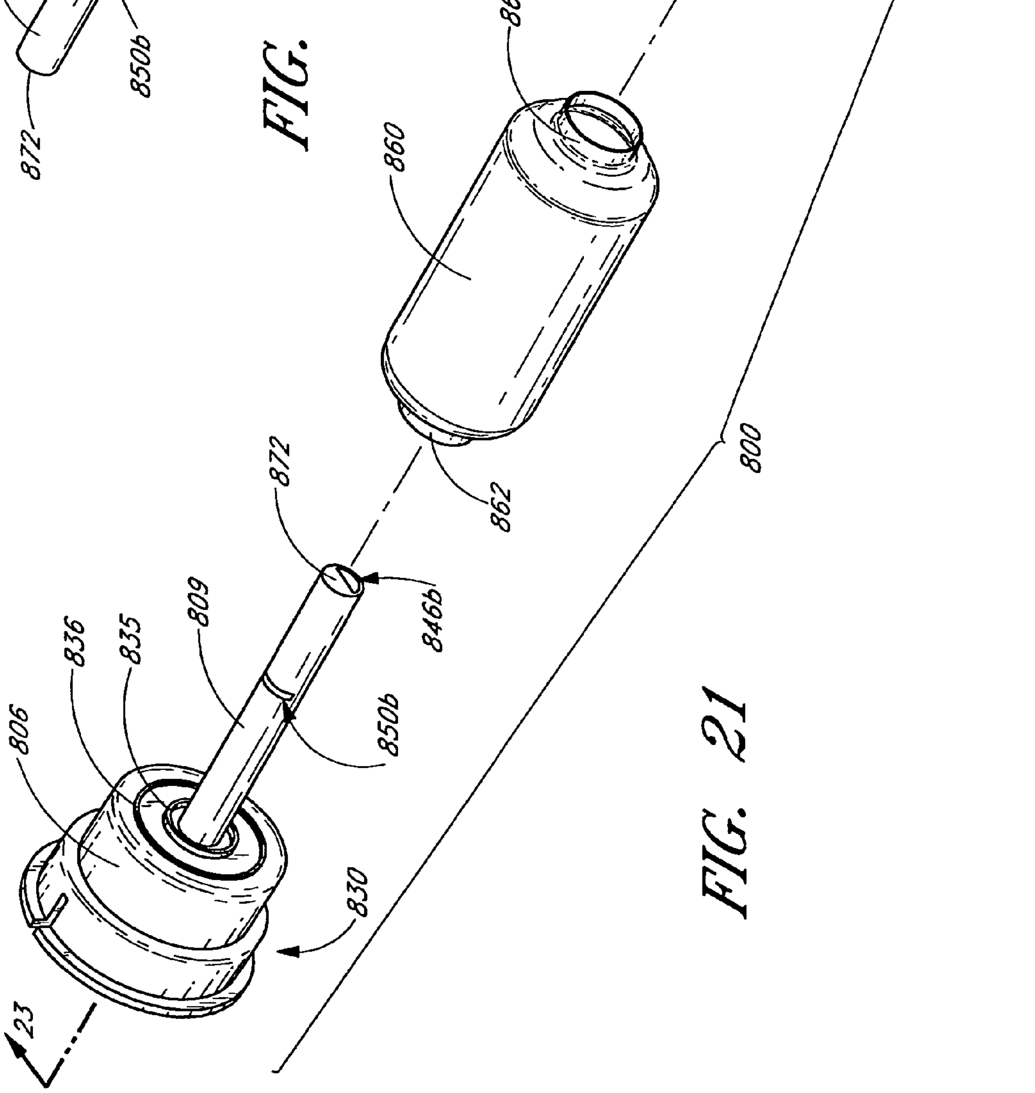

FIG. 21 illustrates an embodiment of an adaptor 800 in a disassembled state. The adaptor 800 comprises a housing member 806, a bag 860, and a casing member 870. In certain embodiments, the adaptor 800 is configured to provide sterilized air to the vial 210 as fluid is withdrawn therefrom.

Figure 22:
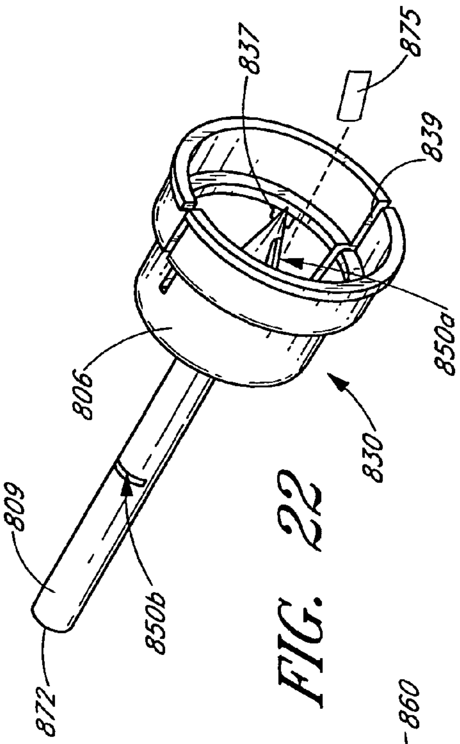
FIG. 22 is a perspective view of a housing member of the vial adaptor of FIG. 21.
Figure 23:
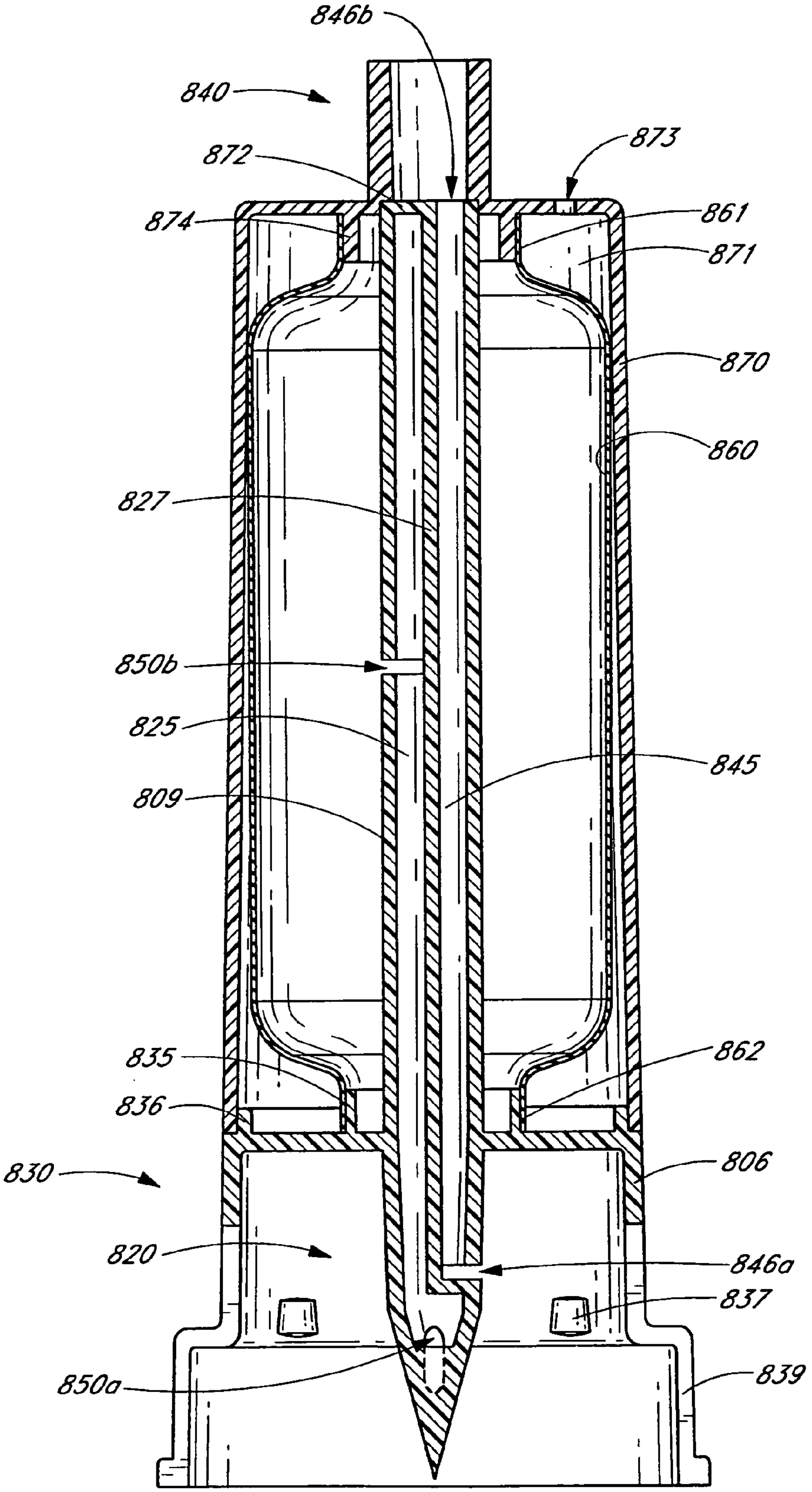
FIG. 23 is a cross-sectional view of the vial adaptor of FIG. 21 after assembly.

With reference to FIGS. 21, 22, and 23, in certain embodiments, the housing member 806 comprises a cap connector 830, a piercing member 820, and a proximal extension 809 which, in some arrangements, are integrally formed of a unitary piece of material. In some embodiments, the housing member comprises polycarbonate plastic.

The cap connector 830 resembles similarly numbered cap connectors described above in many ways. In some instances, the cap connector 830 comprises one or more projections 837 and/or one or more slits 839. In some arrangements, an inner ring 835 and an outer ring 836 project from a proximal surface of the cap connector 830. The inner ring 835 can be configured to couple with the bag 860, as described below. The outer ring 836 can be configured to couple with the casing member 870, preferably in substantially airtight engagement via any suitable means, including those described herein.

In certain arrangements, the piercing member 820 extends distally from a central portion of the cap connector 830 and the proximal extension 809 extends proximally from the central portion of the cap connector 830. Together, the piercing member 820 and proximal extension 809 define an outer boundary of both a regulator channel 825 and an extractor channel 845. An inner wall 827 defines an inner boundary between the regulator channel 825 and the extractor channel 845.

In some arrangements, the piercing member 820 defines a distal regulator aperture 850*a* configured to be located within the vial 210 when the adaptor 800 is coupled therewith. The distal regulator aperture 850*a* permits fluid communication between the vial 210 and the regulator channel 825. The piercing member 820 can also define a distal extractor aperture 846*a*. Advantageously, the distal extractor aperture 846*a* can be configured to be located adjacent an interior surface of the septum 216 when the adaptor 800 is coupled with the vial 210, thereby permitting withdrawal of most or all of the liquid from the vial 210 through the extractor channel 845.

In certain configurations, the proximal extension 809 defines a proximal regulator aperture 850*b* that allows fluid communication between the bag 860 and the regulator channel 825. The proximal regulator aperture 850*b* can be located anywhere along the length of the portion of the proximal extension 809 that defines the outer boundary of the regulator channel 825, and can assume various sizes. In some instances, the proximal regulator aperture 805*b* is located at or adjacent the longitudinal center of the proximal extension 809. In certain configurations, the purpose of the above-noted portion of the proximal extension 809 is primarily structural. Accordingly, in some arrangements, this portion is eliminated, and the proximal regulator aperture 850*b* is instead defined by the cap connector 830. The proximal extension 809 can also define a proximal extractor aperture 846*b* that allows fluid communication between a medical connector interface 840 and the extractor channel 845.

With reference to FIGS. 21 and 23, in certain embodiments, the casing member 870 defines a cavity 871 for housing the bag 860. The casing member 870 can comprise the medical connector interface 840, which resembles similarly numbered medical connector interfaces described above in many ways. In certain arrangements, a base portion of the medical connector interface 840 is configured to accept a proximal end 872 of the proximal extension 809. In some arrangements, the proximal end 872 is attached to the casing member 870 in substantially airtight engagement via any suitable means, including those disclosed herein. In some arrangements, the casing member 870 comprises a venting aperture 873. The venting aperture 873 allows ambient air to enter the chamber 871, thereby exposing an exterior surface of the bag 860 to atmospheric pressure, described in more detail below. The casing member 870 can comprise a proximal ring 874 for coupling the casing member 870 with the bag 860, as discussed below. The casing member 870 preferably comprises a rigid material capable of protecting the bag 860, and in some instances comprises polycarbonate plastic.

In some arrangements, the bag 860 comprises a proximal flange 861 and a distal flange 862. The proximal flange 861 can be sized and configured to couple with the proximal ring 874 of the casing member 870, and the distal flange 862 can be sized and configured to couple with the inner ring 835 of the housing member 806, preferably in substantially airtight engagement. In some instances, a substantially airtight engagement is achieved with flanges 861, 862 that comprise stiffer and/or thicker material than the remainder of the bag 860. In further arrangements, an inner diameter of the flanges 861, 862 is slightly smaller than an outer diameter of the rings 874, 835, respectively. In some arrangements, the flanges 861, 862 are adhered to the rings 874, 835, respectively.

In various configurations, the inner diameter of either of the flanges 861, 862 is from about 0.10 to about 0.40 inches, from about 0.15 to about 0.35, or from about 0.20 to about 0.30 inches. In other configurations, the inner diameter is at least about 0.10 inches, at least about 0.15 inches, at least about 0.20 inches, or at least about 0.25 inches. In still other configurations, the inner diameter is no more than about 0.30 inches, no more than about 0.35 inches, or no more than about 0.40 inches. In some embodiments, the inner diameter is about 0.25 inches.

In various configurations, the height of the bag 860, as measured from tip to tip of the flanges 861, 862, is from about 1.00 to 3.00 inches, from about 1.50 to 2.50 inches, or from about 1.75 to about 2.25 inches. In other configurations, the height is at least about 1.00 inches, at least about 1.50 inches, at least about 1.75 inches, or at least about 2.00 inches. In still other configurations, the height is no more than about 2.25 inches, no more than about 2.50 inches, or no more than about 3.00 inches. In some embodiments, the height is about 2.00 inches.

In various configurations, the width of the bag 860 is from about 0.80 inches to about 1.00 inches, from about 0.85 inches to about 0.95 inches, or from about 0.87 to about 0.89 inches. In other configurations, the width is at least about 0.80 inches, at least about 0.85 inches, or at least about 0.87 inches. In still other configurations, the width is no more than about 0.89 inches, no more than about 0.95 inches, or no more than about 1.00 inches. In some configurations, the width is about 0.875 inches. In some configurations, the thickness of the bag 860 is from about 0.0005 inches to about 0.010 inches. In many arrangements, the bag 860 is sufficiently thick to resist tearing or puncturing during manufacture or use, but sufficiently flexible to contract under relatively small pressure differentials, such as pressure differentials no more than about 1 psi, no more than about 2 psi, no more than about 3 psi, no more than about 4 psi, or no more than about 5 psi.

In some embodiments, the bag 860 is both circularly symmetric and symmetric about a latitudinal plane passing through a center of the bag 860. In such embodiments, assembly of the adaptor 800 is facilitated because the bag 860 can assume any of a number of equally acceptable orientations within the adaptor 800.

In certain arrangements, the bag 860 comprises sterilized air that can be drawn into the vial 210 (not shown) as fluid is withdrawn therefrom. In some arrangements, the air within the bag 860 is pressurized to correspond with the approximate atmospheric pressure at which the adaptor 800 is expected to be used. In some instances, a removable cover or tab 875 (shown in FIG. 22) is placed over the distal regulator aperture 850*a* in order to maintain the pressure within the bag 860 and to ensure that the air within the bag 860 remains sterile up through coupling of the adaptor 800 with the vial 210. As with the jacket 505 described above, the tab 875 can be configured to catch on the septum 216 and remain there as the piercing member 820 is inserted through the septum 216. Other suitable methods can also be used for maintaining the pressure within the bag 860 and ensuring that the air within the bag 860 remains sterile up through coupling of the adaptor 800 with the vial 210.

In some instances, when the adaptor 800 is coupled with the vial 210, the atmospheric pressure within the extractor channel 845 corresponds with the pressure within the bag 860. As fluid is withdrawn from the vial 210, the pressure within the vial 210 drops. Accordingly, sterilized air flows from the bag 860 into the vial 210. For reasons discussed above in connection with other adaptors, in some embodiments, the bag 860 comprises a volume of air equal to or greater than the volume of fluid contained in the vial 210. In some arrangements, the bag 860 is also preferably configured to readily collapse.

In certain configurations, as fluid is withdrawn from the vial 210, it flows through the distal extractor aperture 846*a*, the extractor channel 845, the proximal extractor aperture 846*b*, and the medical connector interface 840. As pressure drops within the vial 210, sterilized air is withdrawn from the bag 860, through the proximal regulator aperture 850*b*, through the regulator channel 825, through the distal regulator aperture 850*a*, and into the vial 210.

In some instances, excess fluid and/or bubbles are returned to the vial 210. Injecting fluid and/or air into the vial 210 increases pressure within the vial 210. As a result, in some arrangements, air and/or fluid within the vial 210 flows through the distal regulator aperture 850*a* into the regulator channel 825. In some instances, the air and/or fluid additionally flows into the bag 860. In many instances, it is desirable to prevent fluid from flowing into the bag 860. Accordingly, in some arrangements, the proximal regulator aperture 850*b* can be small so as permit air to flow therethrough but resist introduction of fluid to the bag 860. In other arrangements, a hydrophobic filter, membrane, or mesh is disposed over the proximal regulator aperture 850*b*. The adaptor 800 thus can be particularly suited to allow the expulsion of excess fluid or air bubbles from a syringe or other medical instrument.

Figure 24:
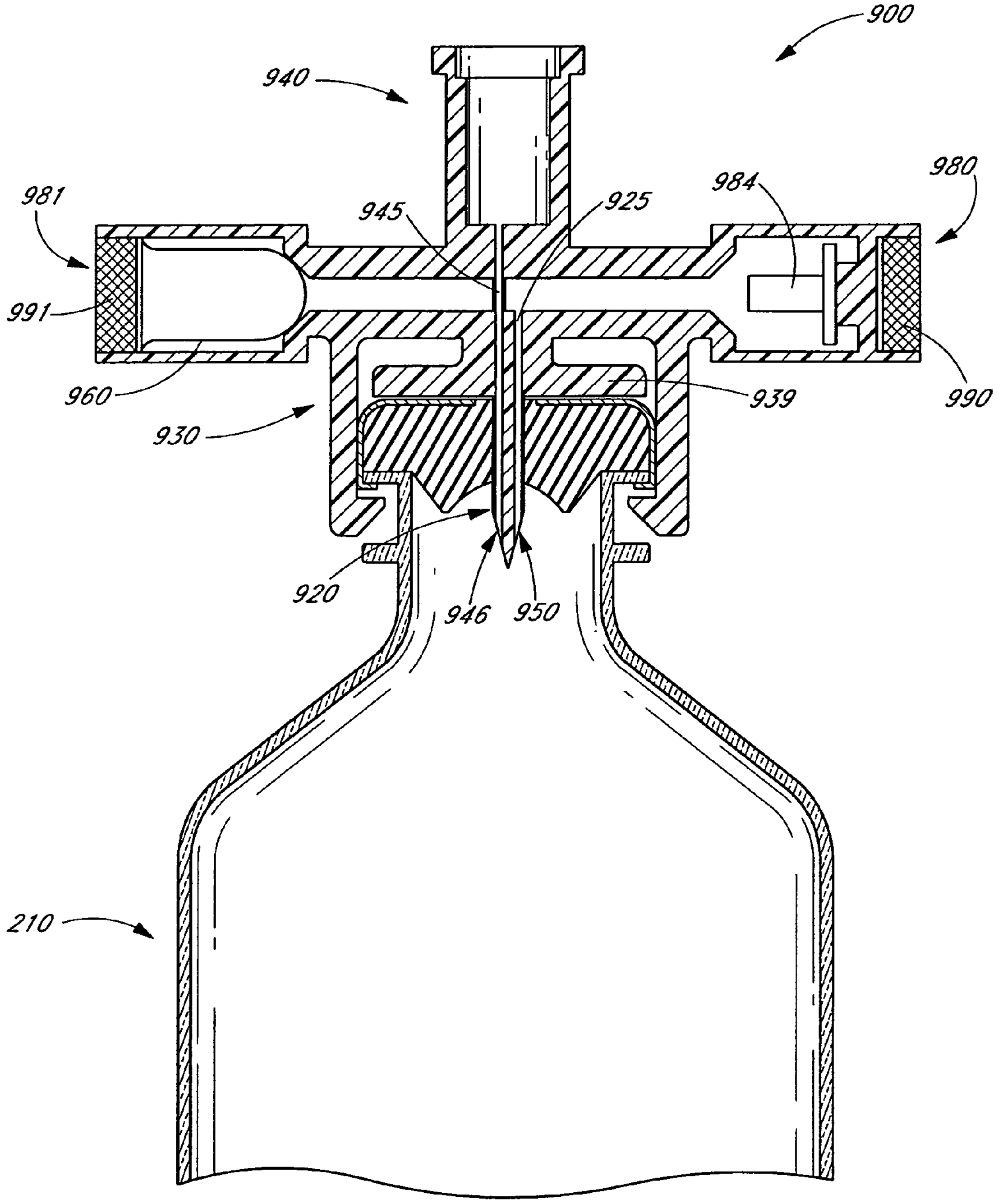
FIG. 24 is a partial cross-sectional view of a vial adaptor coupled with a vial.

FIG. 24 illustrates an embodiment of a vial adaptor 900 coupled with the vial 210. The adaptor 900 comprises a medical connector interface 940, a cap connector 930, and a piercing member 920. The adaptor 900 further comprises an input port 980 and regulator port 981. In certain embodiments, the ports 980, 981 are disposed at opposite ends of the adaptor 900 in order to balance the adaptor 900. As shown, in some embodiments, a single housing comprises each of the above-noted features. The housing can comprise any rigid material, such as plastic.

In some embodiments, the medical connector interface 940 and the cap connector interface 930 represent similarly numbered features described above. In the illustrated embodiment, the cap connector 930 comprises a platform 939.

In certain embodiments, the piercing member 920 defines an extractor aperture 946, a distal portion of an extractor channel 945, a regulator aperture 950, and a distal portion of a regulator channel 925. The apertures 946, 950 can be positioned on the sides of the piercing member 920 or at a distal end 923 thereof, as illustrated.

In certain embodiments, the extractor channel 945 extends through the piercing member 920, through the cap connector 930, and through the medical connector interface 940. The regulator channel 925 extends through the piercing member 920, through the cap connector 930, and into the ports 980, 981.

In some embodiments, the input port 980 comprises a hydrophobic filter 990. Such filters are generally known in the art. The filter 990 prevents dust, bacteria, microbes, spores, and other contaminants from entering the vial 210. In some embodiments, the input port 980 comprises a valve 984. The valve 984 is configured to permit air that has passed through the filter 990 to pass into the regulator channel 925, but to prevent any air or fluid from passing through the valve 984 in the other direction.

In some embodiments, the regulator port 981 comprises a hydrophobic filter 991. In some instances, the filter 991 is identical to the filter 990. However, in many embodiments, the hydrophobic filter need only be capable of prohibiting the passage therethrough of liquids or vapors, whether or not it is capable of filtering out dust, bacteria, etc. In many embodiments, the regulator port 981 comprises a bag 960 in substantially airtight engagement with the port 981. In some instances, the bag 960 comprises a flexible material capable of expanding and contracting. In many instances, the bag 960 comprises a substantially impervious material. In certain configurations, the bag 960 comprises Mylar®, polyester, polyethylene, polypropylene, saran, latex rubber, polyisoprene, silicone rubber, and polyurethane.

In some configurations, as fluid is withdrawn from the vial 210 through the extractor channel 945, ambient air passes through the filter 990, through the valve 984, through the regulator channel 925, and into the vial 210. The bag 960, if not already inflated, tends to inflate within the regulator port 981 due to pressure within the vial 210 being lower than atmospheric pressure.

In certain configurations, as fluid and/or air is returned to the vial 210, pressure within the vial 210 increases. Fluid is thus forced into the regulator channel 925. Because the valve 984 prevents passage therethrough of fluid, the fluid fills the regulator channel 925 and collapses the bag 960. So long as the volume of fluid returned to the vial 210 is smaller than the volume of the bag 960, the pressure within the vial 210 generally does not increase significantly. However, once the bag 960 is completely collapsed, additional return of fluid to the vial 210 generally increases the pressure within the vial 210. Accordingly, in some arrangements, the size of the bag 960 determines the amount of overdrawn fluid that can be returned to the vial 210 without causing any of the pressure-related problems described above. In various embodiments, the bag 960, when expanded, has a volume of between about 0.5 cc and 5 cc, between about 1 cc and 4 cc, or between about 1.5 cc and about 2 cc. In some embodiments the volume is no more than about 2 cc or no more than about 1 cc. In some instances, the adaptor 900 houses a relatively small bag 960 having a volume of about 1 cc or about 2 cc, for example, which permits the return of bubbles or small amounts of overdrawn fluid while keeping the adaptor 900 from being overly bulky.

In certain embodiments, the presence of filters 990, 991 that are hydrophobic can be precautionary and may not be warranted. In principle, the valve 984 and the substantially impervious bag 960 should prevent any fluid from passing from the vial 210 to the exterior of the adaptor 900. However, in the unlikely event that the valve 984 were to fail or the bag 960 were to rupture, the hydrophobic filters 990, 991 could serve to prevent fluid from exiting the adaptor 900. Similarly, in some instances, the collapsible bag 960 is removed from the regulator port 991 and/or the valve 984 is removed from the input port 980 without affecting the operation of the adaptor 900.

Figure 25:
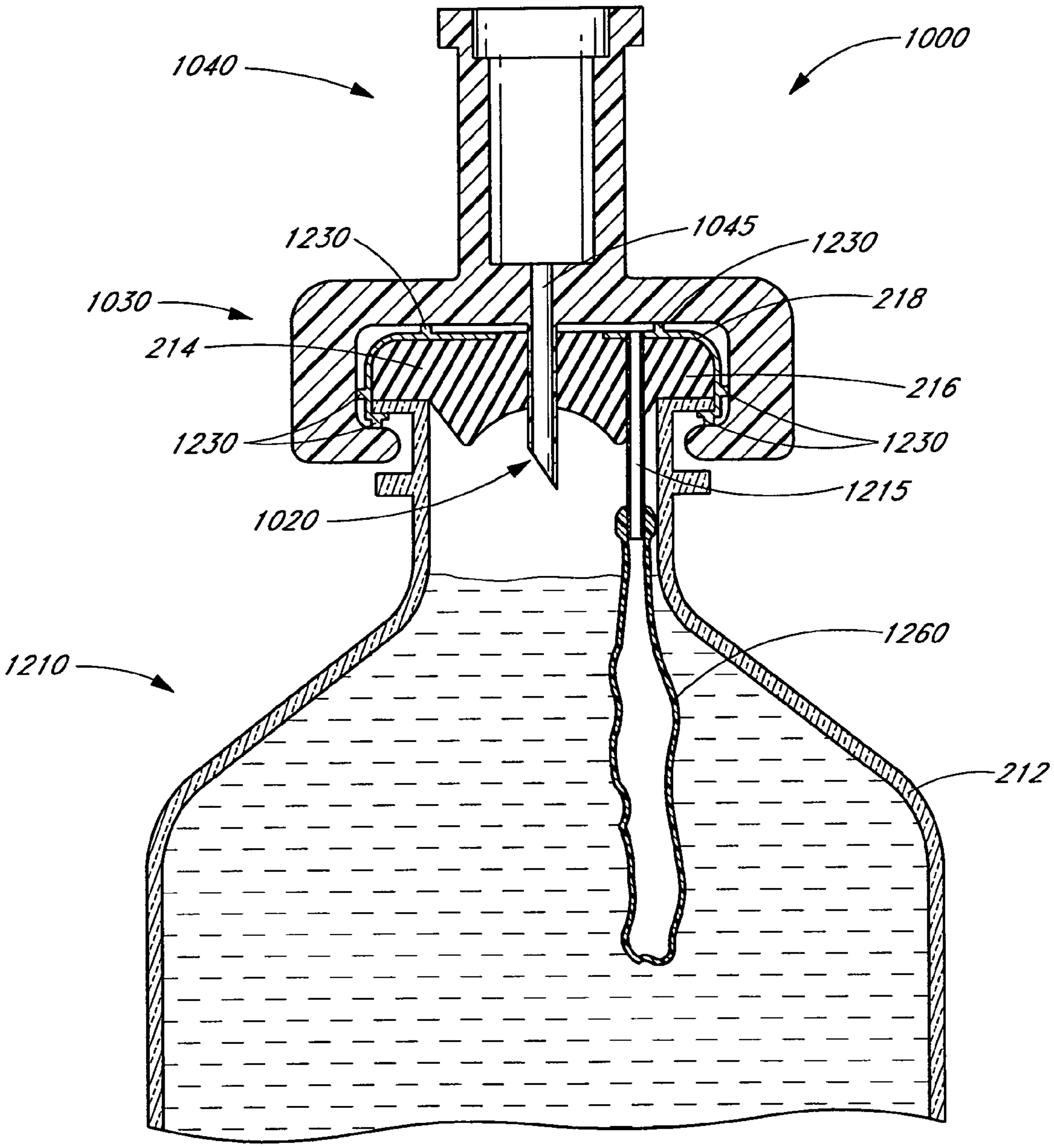
FIG. 25 is a partial cross-sectional view of a vial adaptor coupled with a vial.

FIG. 25 illustrates an embodiment of an adaptor 1000 coupled with a vial 1210. The adaptor 1000 comprises a medical device interface 1040, a cap connector 1030, and a piercing member 1020, each of which resembles similarly numbered features described herein in many ways. In some embodiments, the adaptor 1000 comprises an extractor channel 1045 for removing fluid from the vial 1210, but does not comprise a regulator channel. The vial 1210 resembles the vial 210 except as detailed hereafter.

Figure 26:
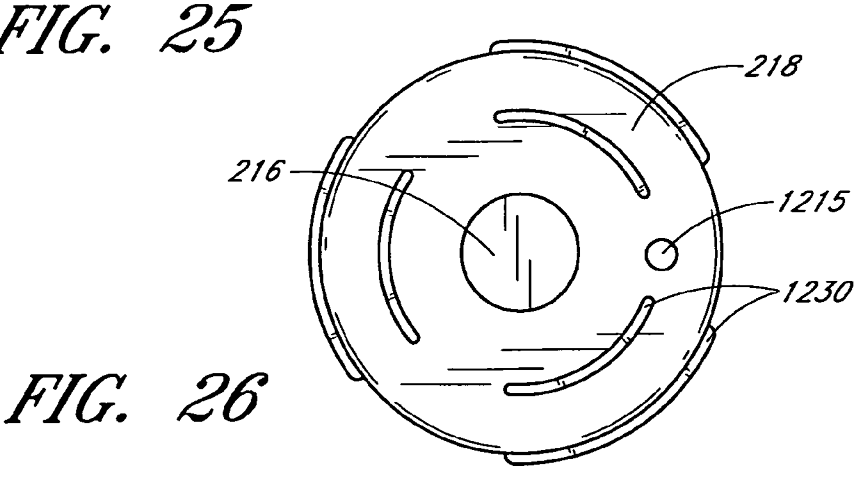
FIG. 26 is a top plan view of a cap of a vial.

In certain embodiments, the vial 1210 comprises a regulator conduit 1215 coupled at one end with a bag 1260, preferably in substantially airtight engagement. In some embodiments, the regulator conduit 1215 extends through the septum 216 and through the casing 218. In such embodiments, the portion of the septum 216 that is normally visible to a user is substantially unaffected by the presence of the conduit 1215, as illustrated in FIG. 26. Accordingly, a user would generally not risk accidentally trying to insert the piercing member 1020 into or over the regulator conduit 1215. In other embodiments, the regulator conduit 1215 extends through the septum 216 only. In still other embodiments, the regulator conduit 1215 extends through the body 212 of the vial 1210. In some embodiments, especially those in which a syringe with a needle is expected to pierce the vial 1210, the regulator conduit 1215 can be substantially longer than is shown in the illustrated embodiment to avoid puncture of the bag 1260 by the needle. In some instances, the regulator conduit 1215 can extend further into the vial 1210 than the maximum distance that a needle can extend into the vial 1210. The regulator conduit 1215 can extend at least about ¼, ⅓, ½, ¾, or substantially all of the distance from the interior wall of the vial 1210. The regulator conduit 1215 can also be curved to conform with the curved shape of the neck portion of a standard vial. In this way, the regulator conduit 1215 can help to position the bag 1260 as far as possible from a needle or piercing member 1020 that penetrates the septum 216. In certain instances, the vial 1210 is filled with a medical fluid, is slightly evacuated, and is then hermetically sealed. In many embodiments, the bag 1260 is included in the sealed vial 1210 in a generally collapsed state. However, atmospheric pressure acting on the interior of the bag 1260 can cause it to expand slightly within the sealed vial 1210 in some instances.

The adaptor 1000 can be coupled to the vial 1210. In some instances, insertion of the piercing member 1020 results in slight pressure changes within the vial 1210 that force the bag 1260 away from the piercing member 1020. In certain arrangements, the piercing member 1020 extends just beyond a distal surface of the septum 216, and is spaced away from the bag 260. It is appreciated that any adaptor disclosed herein could be coupled with the vial 1210, as could numerous other adaptors configured to be coupled with a standard medicinal vial. As fluid is withdrawn from the vial 1210 or injected into the vial 1210, the bag 1260 expands and contracts, respectively, in a manner as disclosed herein.

In certain embodiments, the vial 1210 comprises one or more extensions 1230. The extensions 1230 can be disposed around the perimeter of the cap 214, as shown, or they can be located at other points on the cap 214. In some instances, the one or more extensions 1230 are located on a distal side of the cap 214, on a proximal side of the cap 214, and/or around a surface extending between the proximal and distal sides of the cap 214. In many arrangements, the extensions 1230 extend only a short distance around the perimeter of the cap 214. In many arrangements, the extensions 1230 maintain space between the cap 214 and the cap connector 1030 when the vial adaptor 1000 is coupled with the vial 1210, thus allowing ambient air to flow freely into and/or out of the regulator conduit 1215. In other embodiments, the vial adaptor 1000 comprises extensions 1230 for the same purpose. Other arrangements are possible for permitting air to flow freely into and/or out of the regulator conduit 1215. For example, the vial adaptor 1000 can comprise a venting channel (not shown) extending through the cap connector 1230.

Figure 27:
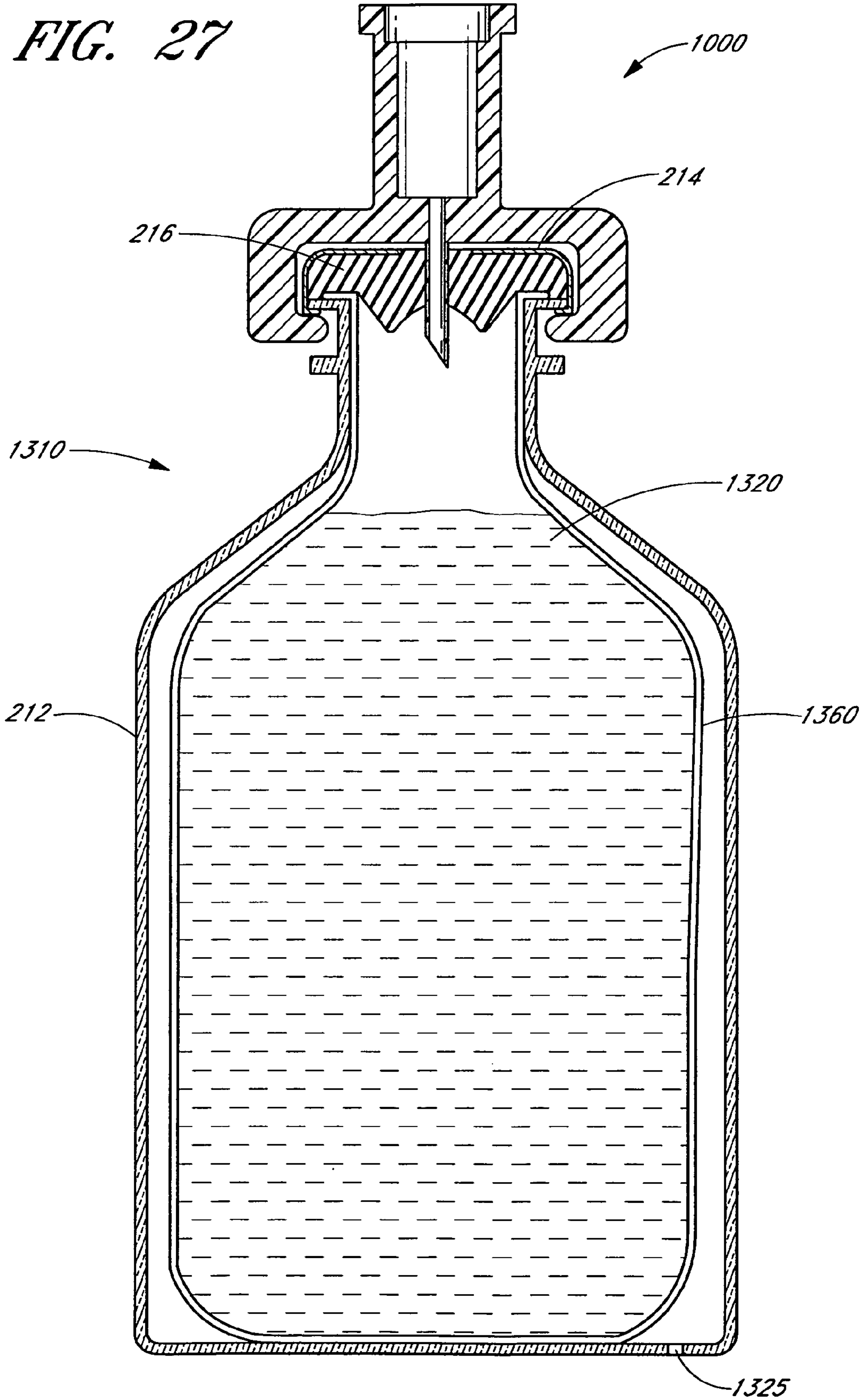
FIG. 27 is a cross-sectional view of a vial adaptor coupled with a vial.

FIG. 27 illustrates an embodiment of a vial 1310 comprising a bag 1360 coupled with the adaptor 1000. In some embodiments, the bag 1360 is filled with a medical fluid 1320. A distal end 1362 of the bag 1360 can be hermetically sealed to the cap 214. In some instances, the distal end 1362 is sealed between the septum 216 and a proximal end of the body 212. In certain embodiments, the vial 1310 comprises a venting aperture 1325. The venting aperture 1325 can be located anywhere on the body 212. In some arrangements, the venting aperture 1325 is located at a distal end of the body 212. Accordingly, the bag 1360 does not obstruct the venting aperture 1325 when fluid is withdrawn from the vial 1310 in an upside-down configuration. In some instances, the venting aperture 1325 is covered by a filter or a screen to prevent debris or other items from entering the vial 1310 and possibly puncturing the bag 1360.

In certain instances, as a volume of fluid is withdrawn from the vial 1310, the bag 1360 contracts to a new smaller volume to account for the amount of fluid withdrawn. In some instances, due to the venting aperture 1325, the pressure surrounding the bag 1360 and the pressure acting on a device used to extract the fluid, such as a syringe, are the same when fluid ceases to be withdrawn from the vial 1310. Accordingly, extraction of fluid from the vial 1310 can be similar to other methods and systems described herein in many ways.

Figure 28:
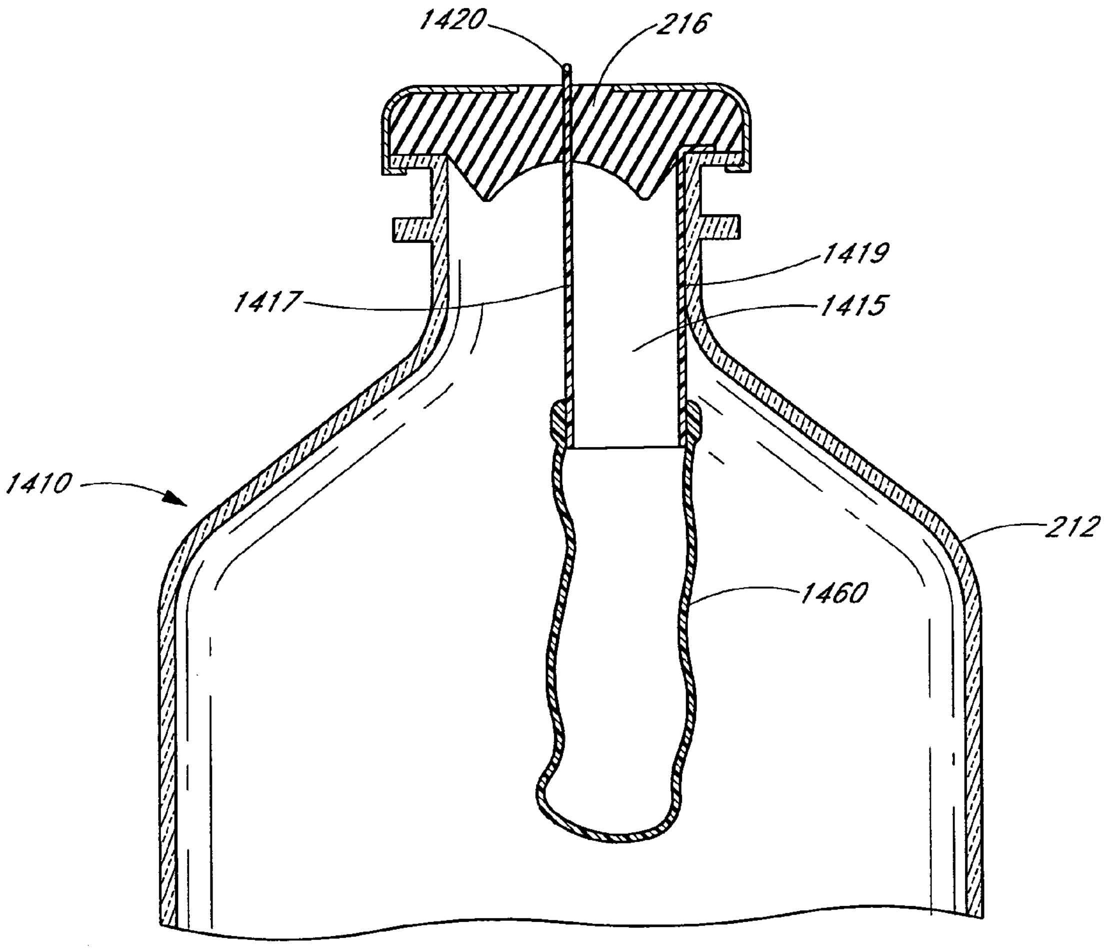
FIG. 28 is a partial cross-sectional view of a vial.

FIG. 28 illustrates an embodiment of a vial 1410 comprising a bag 1460. In some arrangements, the vial 1410 comprises a regulator conduit 1415 coupled at one end with the bag 1460, preferably in substantially airtight engagement. In certain configurations, the regulator conduit 1415 comprises a center wall 1417 and an outer wall 1419. In some arrangements, the center wall 1417 bisects the septum 216, extending along the diameter of the septum 216. The center wall 1417 can comprise a flange 1420 that extends proximally from the septum 216 along a portion thereof not covered by the casing 218. In some arrangements, the outer wall 1419 is sealed in substantially airtight engagement between the septum 216 and a proximal end of the body 212. In some configurations, the outer wall 1419 is substantially semicircular.

Accordingly, in some embodiments, the septum 216 is divided into two portions by the regulator conduit 1415. Piercing one portion of the septum 216 provides access to the contents of the vial 1410, and piercing the other portion of the septum 216 provides access to the regulator conduit 1415 and the bag 1460. In some configurations, at least a proximal surface of the septum 216 is colored, painted, or otherwise marked to indicate the different portions of the septum 216.

Figure 29:
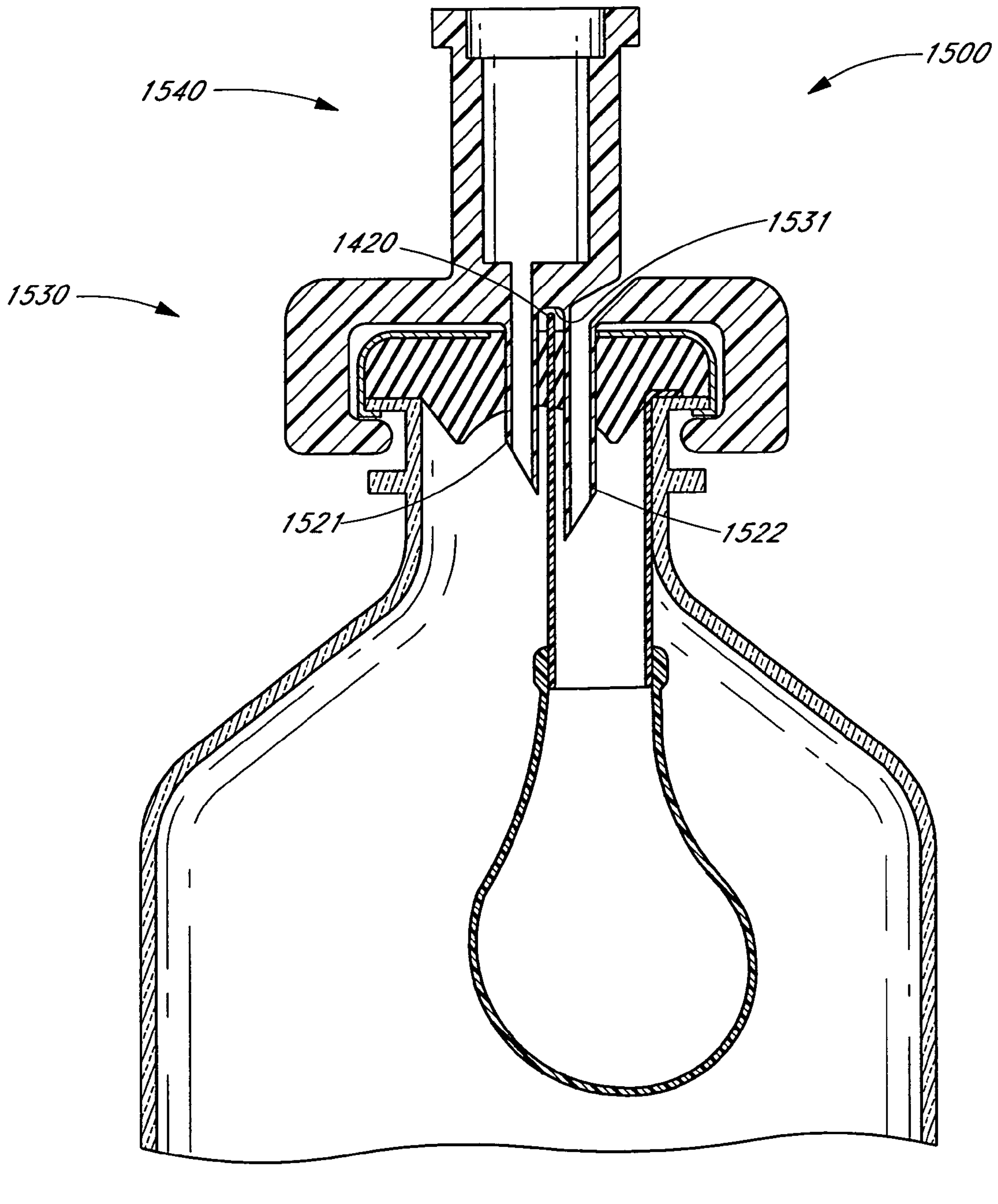
FIG. 29 is a partial cross-sectional view of a vial adaptor coupled with a vial.

FIG. 29 illustrates an embodiment of an adaptor 1500 coupled with the vial 1410. The adaptor 1500 comprises a medical connector interface 1540 and a cap connector 1530 that resemble similarly numbered features described herein. The cap connector 1530 can define a groove 1531 having sufficient depth to accept the flange 1420 or to avoid contact therewith.

In some configurations, the adaptor 1500 comprises an extractor piercing member 1521 and a regulator piercing member 1522. In some embodiments, the extractor piercing member 1521 is configured to extend just beyond a distal surface of the septum 216. Accordingly, in some instances, the regulator piercing member 1522 is longer than the extractor piercing member 1521, which provides a means for distinguishing the piercing members 1521, 1522 from each other. Other methods for distinguishing the piercing members 1521, 1522 can also be employed. The adaptor 1500 can be colored, painted, or otherwise marked to indicate correspondence with the different sections of the septum 216.

In some instances, the extractor piercing member 1521 provides fluid communication with the liquid contents of the vial 1410, and the regulator piercing member 1522 provides fluid communication with the bag 1460. Accordingly, removal of liquid from the vial 1410 via the adaptor 1500 can be similar to other liquid removal methods and systems described herein in many ways.

Figure 30:
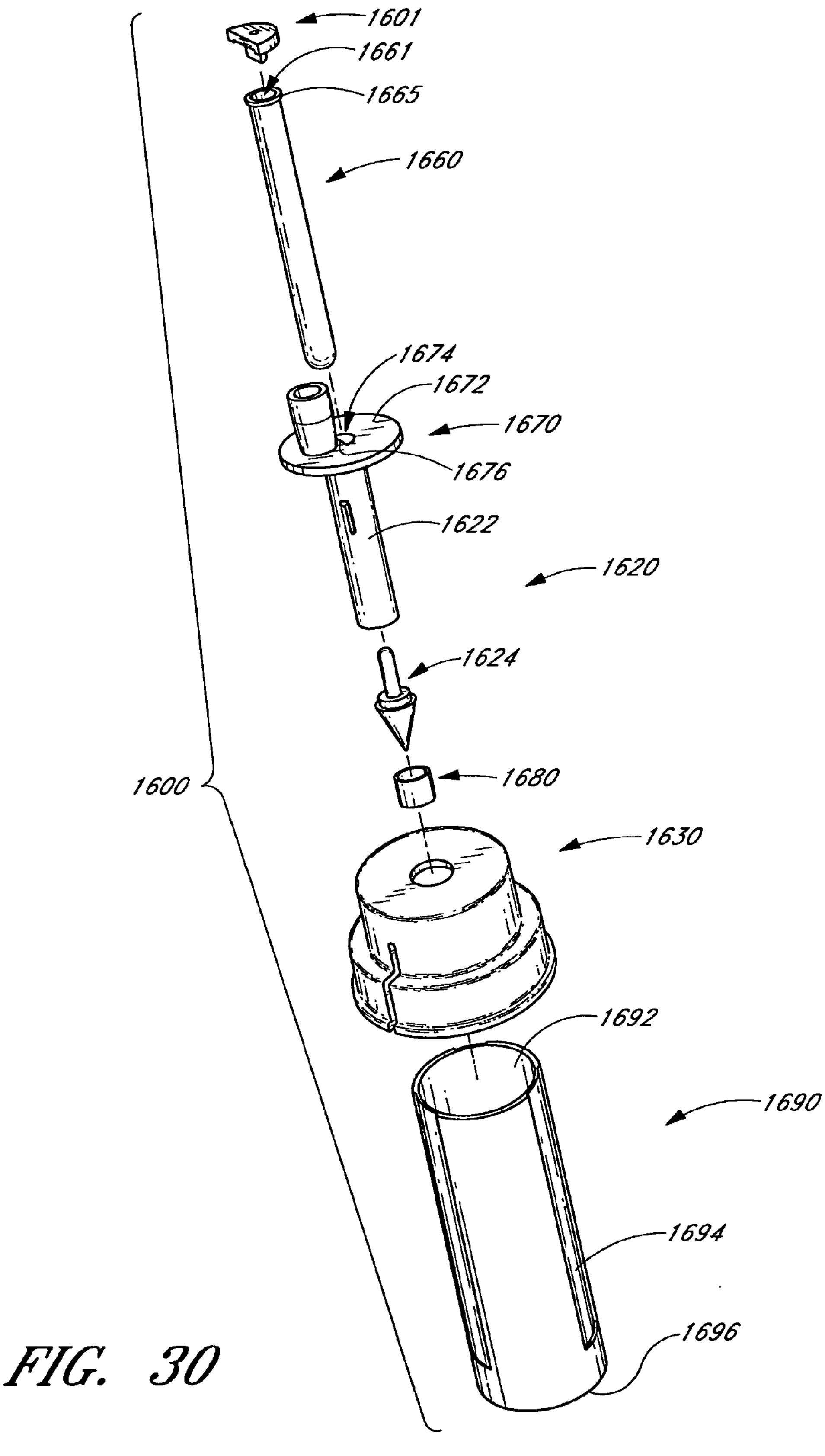
FIG. 30 is an exploded perspective view of a vial adaptor.

FIG. 30 illustrates an embodiment of an adaptor 1600 in a disassembled state. The adaptor 1600 can be coupled with a vial, such as the vial 210 described above. The adapter 1600 resembles the adaptors described above in many ways, but differs in manners such as those discussed hereafter. Any suitable combination of features, structures, or characteristics described with respect to the adaptor 1600 and/or any other adaptor described herein is possible. In certain embodiments, the adaptor 1600 comprises a plug 1601, a bag 1660, a channel housing member 1670, a tip 1624, a sleeve 1680, a cap connector 1630, and a shroud 1690. In other embodiments, the adaptor 1600 comprises fewer than all of these features or structures. For example, in some embodiments, the adaptor 1600 does not comprise the plug 1601, the sleeve 1680, and/or the shroud 1690. In some arrangements, the channel housing member 1670 and the cap connector 1630 comprise separate pieces, as shown. In other arrangements, the channel housing member 1670 and the cap connector 1630 are integrally formed of a unitary piece of material.

In certain embodiments, the adaptor 1600 comprises a piercing member 1620. In some embodiments, the piercing member 1620 comprises the tip 1624 and the sheath 1622, while in other embodiments, the piercing member 1620 does not comprise the tip 1624. In certain arrangements, the tip 1624 is separable from the sheath 1622. In some instances, the tip 1624 is secured to the sheath 1622 by a sleeve 1680. The sleeve 1680 can be configured to cling to the septum 216 as the sheath 1622 is inserted through the septum 216, thereby remaining on the exterior of the vial 210. In some instances, the sleeve 1680 can resemble the jacket 505 described above. In various arrangements, the sleeve 1680 comprises heat shrink tubing, polyester, polyethylene, polypropylene, saran, latex rubber, polyisoprene, silicone rubber, or polyurethane.

Figure 31:
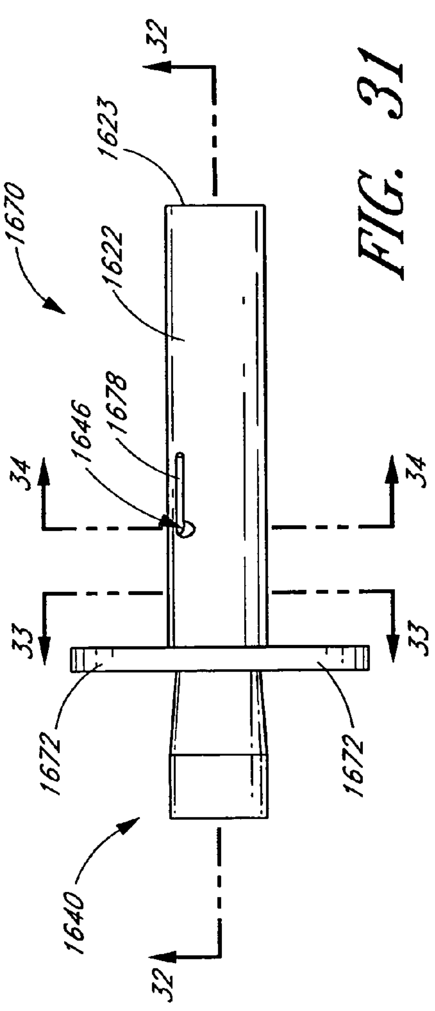
FIG. 31 is a side plan view of a housing member of the vial adaptor of FIG. 30.
Figure 32:
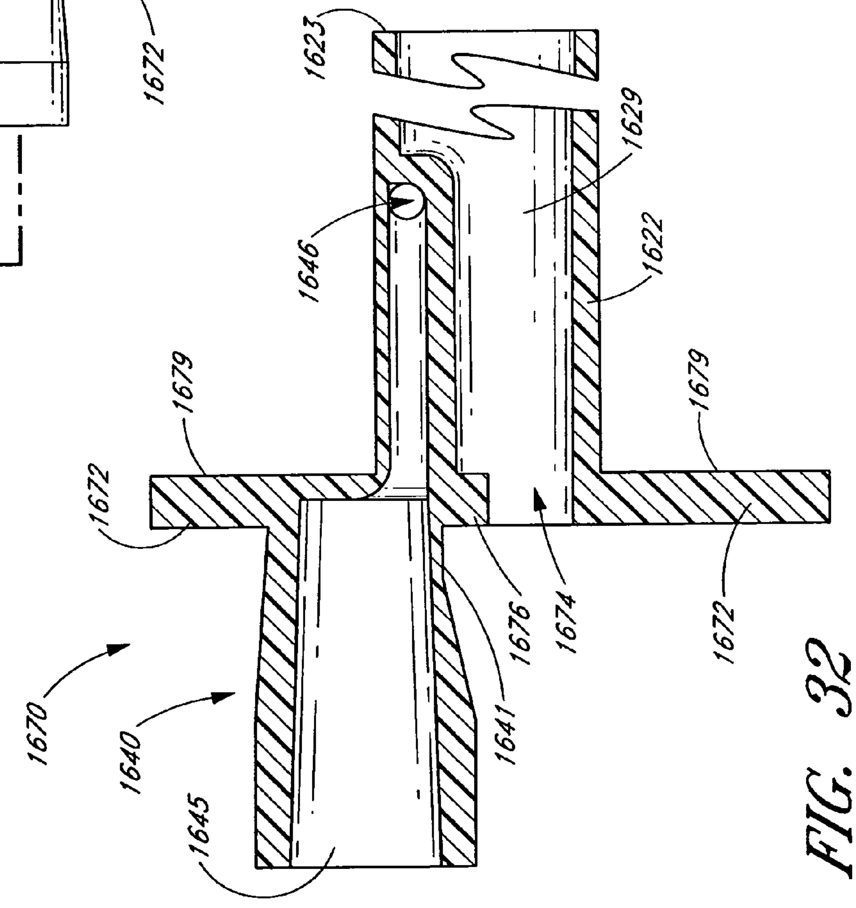
FIG. 32 is a partial cross-sectional view of the housing member of FIG. 31.

With reference to FIGS. 31 and 32, in certain embodiments, the channel housing member 1670 comprises a medical connector interface 1640, a radial extension 1672, and a sheath 1622. In some instances, the medical connector interface 1640, the radial extension 1672, and the sheath 1622 are integrally formed of a unitary piece of material. In many instances, the channel housing member 1670 comprises a stiff material, such as polycarbonate plastic.

The medical connector interface 1640 can resemble other medical connector interfaces described herein in many respects. In certain arrangements, the medical connector interface 1640 defines a proximal end of an extractor channel 1645. In some arrangements, the medical connector interface 1640 is offset from an axial center of the channel housing member 1670.

In some arrangements, the medical connector interface 1640 is asymmetric, and in some instances, comprises an indentation 1641 at a base thereof. In certain instances, the indentation 1641 results from one side of the medical connector interface 1640 having a more tapered and/or thinner sidewall than another side thereof, as illustrated in FIG. 32. In other instances, the indentation 1641 results from the sidewall being shaped differently on two or more sides of the medical connector interface 1640, while the thickness of the sidewall does not substantially vary at any given latitudinal cross-section of the medical connector interface 1640. As described below, in some instances, the indentation 1641 facilitates assembly of the adaptor 1600 and/or permits the use of a larger bag 1660.

Figure 33:
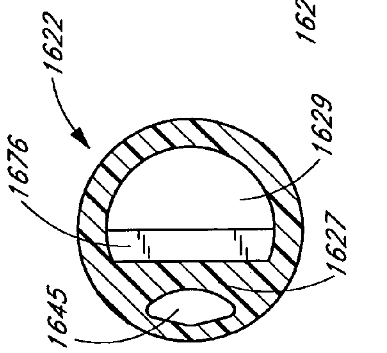
FIG. 33 is a cross-sectional view of the housing member of FIG. 31.

In certain embodiments, the radial extension 1672 projects outward from an axial center of the channel housing member 1670. In some arrangements, the radial extension 1672 is located at the base of the medical connector interface 1640 such that the extractor channel 1645 extends through the radial extension 1672. In further arrangements, the radial extension 1672 defines a bag insertion aperture 1674. In some instances, a ledge 1676 (shown in FIGS. 30, 32, and 33) separates the bag insertion aperture 1674 from the base of the medical connector interface 1640. The bag insertion aperture 1674 can assume any of a variety of shapes. In the illustrated embodiment, the bag insertion aperture 1674 is substantially semicircular with the ledge 1676 defining a flat portion of the semicircle (see FIG. 30).

With reference to FIGS. 31 through 34, the sheath 1622 can resemble other sheaths disclosed herein in many respects. In some embodiments, an axial length of the sheath 1622 is substantially perpendicular to the radial extension 1672. In some arrangements, the sheath 1622 defines at least a distal portion of the extractor channel 1645. In some instances, the portion of the sidewall of the sheath 1622 defining a portion of the extractor channel 1645 is thinner than other portions of the sidewall (see FIGS. 32 and 33). In further arrangements, the sheath 1622 defines a cavity 1629 for housing at least a portion of the bag 1660. In some instances, the extractor channel 1645 and the cavity 1629 are separated by an inner wall 1627. The sheath 1622 can be generally hollow and terminate at a distal end 1623.

Figure 34:
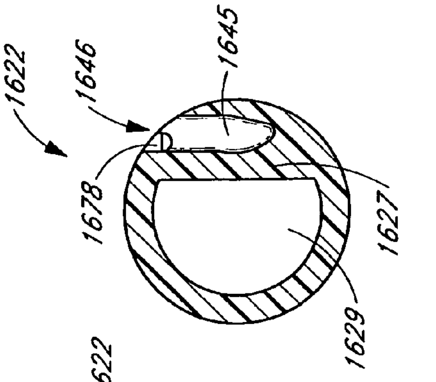
FIG. 34 is another cross-sectional view of the housing member of FIG. 31.

With reference to FIGS. 31, 32, and 34, in some embodiments, an extractor aperture 1646 extends through a sidewall of the sheath 1622 at a distal end of the extractor channel 1645. In some arrangements, the extractor aperture 1646 is substantially circular. In various instances, the diameter of the extractor aperture 1646 is between about 0.020 inches and about 0.060 inches, between about 0.030 inches and about 0.050 inches, or between about 0.035 inches and about 0.045 inches. In other instances the diameter is greater than about 0.020 inches, greater than about 0.030 inches, or greater than about 0.035 inches. In still other instances, the diameter is less than about 0.060 inches, less than about 0.050 inches, or less than about 0.045 inches. In some instances, the diameter is about 0.040 inches.

As described below, in certain arrangements, the extractor aperture 1646 is configured to be adjacent the septum 216 when the adaptor 1600 is coupled with the vial 210. In various instances, a center of the extractor aperture 1646 is spaced from a distal surface 1679 of the radial extension 1672 (see FIG. 32) by a distance of between about 0.25 inches and about 0.35 inches, between about 0.28 inches and about 0.32 inches, or between about 0.29 inches and about 0.31 inches. In other instances, the distance is greater than about 0.25 inches, greater than about 0.28 inches, or greater than about 0.29 inches. In still other instances, the distance is less than about 0.35 inches, less than about 0.32 inches, or less than about 0.31 inches. In some instances, the distance is about 0.305 inches.

With reference to FIGS. 31 and 34, in certain embodiments, a groove 1678 extends distally from the extractor aperture 1646. In some arrangements, the groove 1678 extends along the length of the sheath 1622. In other arrangements, the groove 1678 extends at an angle with respect to the length of the sheath 1622. The groove 1678 can be substantially straight, or it can be curved. In some arrangements, the groove 1678 has a substantially constant depth and width. In other arrangements, the depth and/or width vary along a length of the groove 1678. In some instances, the cross-sectional profile of the groove 1678 is asymmetrical, as shown in FIG. 34. Accordingly, the depth of the groove 1678 can vary from one side of the groove 1678 to the other.

In various arrangements, the length of the groove 1678 is between about 0.15 inches and about 0.35 inches, between about 0.20 inches and about 0.30 inches, or between about 0.23 inches and about 0.27 inches. In other arrangements, the length is greater than about 0.15 inches, greater than about 0.20 inches, or greater than about 0.23 inches. In still other arrangements, the length is less than about 0.35 inches, less than about 0.30 inches, or less than about 0.27 inches. In some embodiments, the length is about 0.25 inches.

In various arrangements, the width of the groove 1678 is between about 0.010 inches and about 0.030 inches, between about 0.015 inches and about 0.025 inches, or between about 0.018 inches and about 0.022 inches. In other arrangements, the width is greater than about 0.010 inches, greater than about 0.015 inches, or greater than about 0.018 inches. In still other arrangements, the width is less than about 0.030 inches, less than about 0.025 inches, or less than about 0.022 inches. In some embodiments, the width is about 0.020 inches.

In various arrangements, the depth of the groove 1678, as measured between the highest point and the lowest point of the cross-sectional profile of the groove 1678, is between about 0.020 inches and about 0.040 inches, between about 0.025 inches and about 0.035 inches, or between about 0.030 inches and about 0.034 inches. In other arrangements, the depth is greater than about 0.020 inches, greater than about 0.025 inches, or greater than about 0.030 inches. In still other arrangements, the depth is less than about 0.040 inches, less than about 0.035 inches, or less than about 0.034 inches. In some embodiments, the depth is about 0.032 inches.

In some instances, it is desirable to remove substantially all of the fluid within the vial 210, such as when the fluid is a costly medication. Accordingly, in certain arrangements, it is desirable for the extractor aperture 1646 to be as close as possible to the septum 216 when the adaptor 1600 is coupled with the vial 210 so that a maximum amount of fluid can be removed from the vial 210. However, the precise dimensions of the septum 216 or, more generally, of the cap 214 can vary among different vials 210 of the same make and size. Further, the adaptor 1600 can be configured to couple with an assortment of vials 210 that vary by size or by source of manufacture. These variations can also result in variations in cap dimensions and, as a result, the location of the extractor aperture 1646 with respect to the septum 216. Advantageously, the groove 1678 can provide a fluid passageway to the extractor aperture 1646, even if the extractor aperture 1640 is partially or completely obstructed by the septum 216. In many instances, the groove 1678 allows the removal of substantially all of the fluid contents of the vial 210, regardless of the precise orientation of the extractor aperture 1646 with respect to the septum 216.

In some instances, the groove 1678 is sized and dimensioned such that the septum 216 does not obstruct the flow of fluid through the groove 1678. In many arrangements, the septum 216 comprises a compliant material that conforms to the shape of an item inserted therethrough, often forming a liquid-tight seal with the item. Accordingly, in some instances, the edges of the groove 1678 are angled sufficiently sharply and the depth of the groove 1678 is sufficiently large to prevent the septum 216 from completely conforming to the shape of the groove 1678. Accordingly, a fluid passageway remains between the septum 216 and the volume of the groove 1678 that is not filled in by the septum 216.

In some instances, the groove 1678 extends into the sheath 1622 at an angle, rather than directly toward the center of the sheath 1622. In some instances, an angled configuration allows the groove 1678 to be deeper than it could be otherwise. In some instances, the depth of the groove 1678 is greater than the thickness of the sheath 1622.

Figure 35:
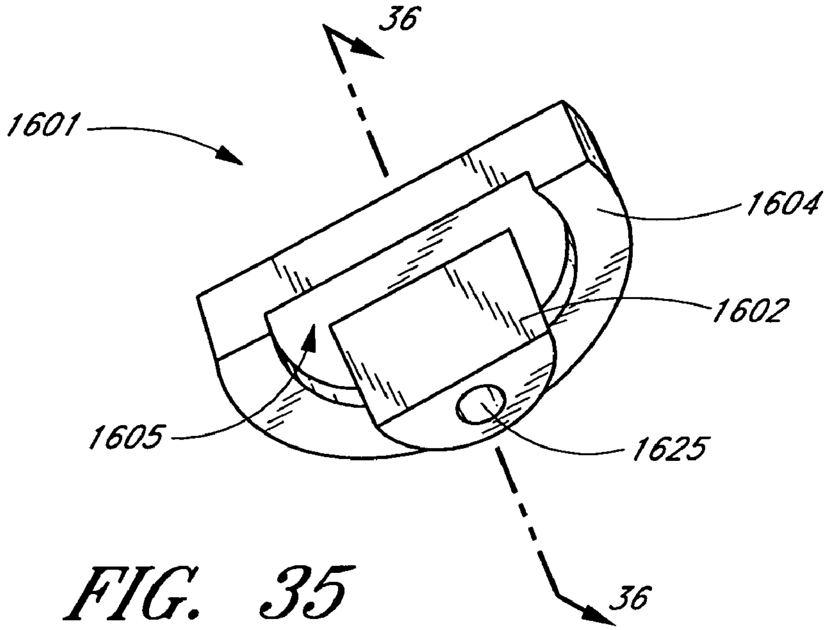
FIG. 35 is a perspective view of a plug of the vial adaptor of FIG. 30.
Figure 36:
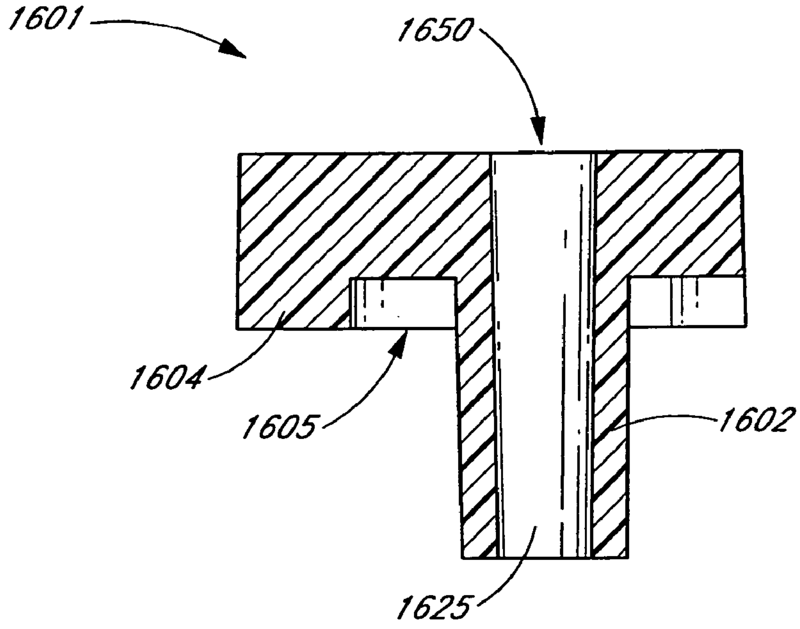
FIG. 36 is a cross-sectional view of the plug of FIG. 35.
Figure 37:
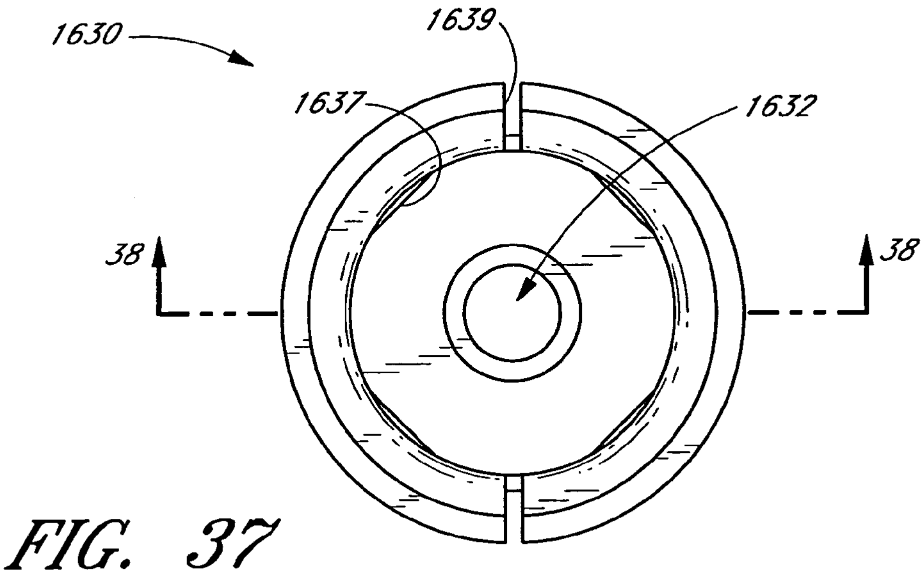
FIG. 37 is a bottom plan view of a cap connector of the vial adaptor of FIG. 30.
Figure 38:
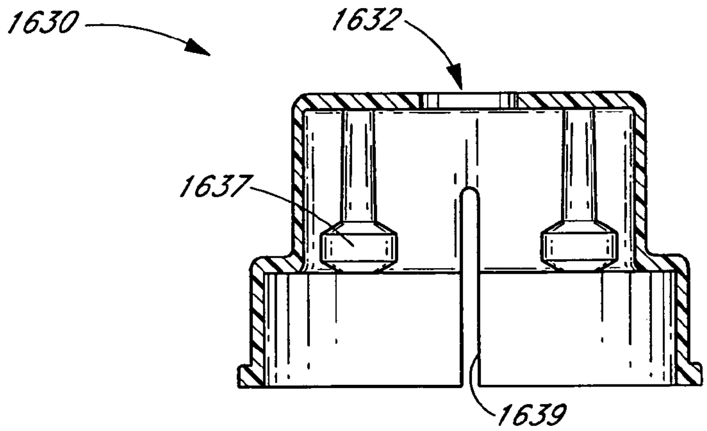
FIG. 38 is a cross-sectional view of the cap connector of FIG. 37.
Figure 39:
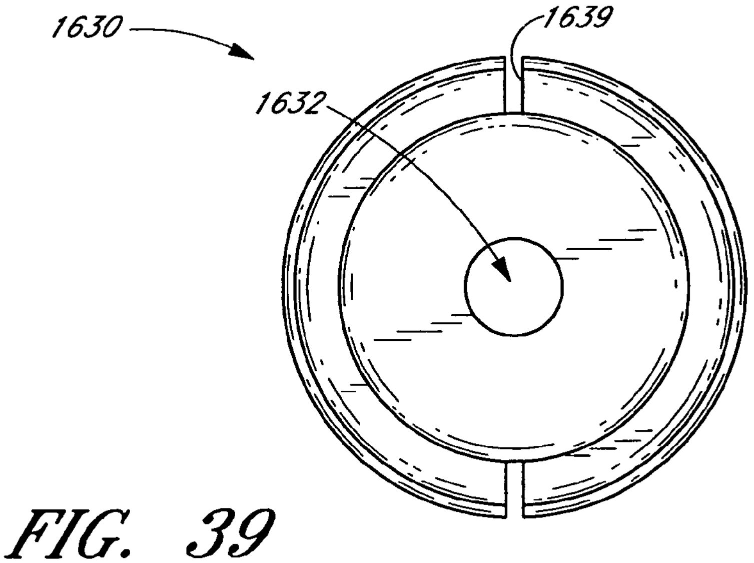
FIG. 39 is a top plan view of the cap connector of FIG. 37.

With reference to FIGS. 30, 35, and 36, the plug 1601 is configured to secure the bag 1660 to the channel housing member 1670. In some arrangements, the plug 1601 comprises a projection 1602 and a rim 1604.

In certain arrangements, the projection 1602 is configured to be inserted into an opening 1661 of the bag 1660 and to tension the bag 1660 against the bag insertion aperture 1674 (see FIG. 30). In some instances, the cross-sectional profile of the projection 1602 is substantially complementary to that of the bag insertion aperture 1674. In the illustrated embodiment, the cross-sectional profile of the projection 1602 is substantially semicircular. The projection 1602 can taper toward a distal end thereof, allowing the projection to be inserted into the bag insertion aperture 1674 with relative ease. In many instances, contact between the projection 1602 and the bag 1660 creates a substantially airtight seal, and contact between the bag 1660 and the channel housing member 1670 creates a substantially airtight seal. In some instances, glue or some other adhesive is applied to the plug 1601, the bag 1660, and/or the channel housing member 1670 to ensure a substantially airtight seal.

In some instances, the semicircular arrangement of the projection 1602 and the bag insertion aperture 1674 facilitates assembly of the adaptor 1600. The asymmetry of the arrangement can help to ensure that the plug 1601 is oriented properly upon insertion thereof into the channel housing member 1670. The asymmetry can also prevent the plug 1601 from rotating within the channel housing member 1670. Other arrangements are also possible for the interface between the plug 1601 and the channel housing member 1670.

In certain arrangements, the rim 1604 extends along a portion of the perimeter of the plug 1601 and defines a recess 1605. In some instances, the recess 1605 is configured to accept a flange 1661 of the bag 1660 (see FIG. 30), thereby allowing a distal surface of the rim 1604 to contact a proximal surface of the radial extension 1672. In some instances, an adhesive is applied to the distal surface of the rim 1604 to help secure the plug 1601 to the channel housing member 1670.

In certain embodiments, the plug 1601 defines a regulator channel 1625. The regulator channel 1625 can extend from a regulator aperture 1650 into the bag 1660 of an assembled adaptor 1600. In certain arrangements, the regulator aperture 1650 is exposed to the environment at the exterior of the assembled adaptor 1600. The regulator channel 1625 can permit air to ingress to and/or egress from the bag 1660.

With reference to FIGS. 30 and 37 through 39, the cap connector 1630 can resemble the cap connectors described above in many ways. In various instances, the cap connector comprises one or more projections 1637 and/or one or more slits 1339. In some arrangements, the cap connector 1630 comprises a piercing member aperture 1632. In some instances, the piercing member 1620 is inserted through the piercing member aperture 1632 during assembly of the adaptor 1600.

In some instances, a proximal surface of the cap connector 1630 is substantially planar. In further instances, a distal surface of the radial projection 1672 of the channel housing member 1670 is also substantially planar. The two planar surfaces can abut one another in an assembled adaptor 1600. Advantageously, a large area of contact between the cap connector 1630 and the radial projection 1672 can permit a secure attachment between these pieces via application of an adhesive, ultrasonic welding, or some other method.

With reference to FIG. 30, in some embodiments, the shroud 1690 is configured to couple with the cap connector 1630. The shroud 1690 can frictionally engage the cap connector 1630, snap into the cap connector 1630, or couple with the cap connector 1630 by any other suitable means. In some arrangements, the shroud 1690 comprises one or more indentations 1694 that can provide traction for removing the shroud 1690 prior to using the adaptor 1600. The shroud can be open at a proximal end 1692 and closed at a distal end 1696. In certain arrangements, the shroud 1690 is configured to enclose the piercing member 1620 without contacting the piercing member 1620. The shroud 1690 can prevent contamination or damage of the piercing member 1620 that may result from accidental contact with the piercing member 1620 prior to use of the adaptor 1600.

Discussion of the various embodiments disclosed herein has generally followed the embodiments illustrated in the figures. However, the particular features, structures, or characteristics of any embodiments discussed herein may be combined in any suitable manner, as would be apparent to one of ordinary skill in the art from this disclosure, in one or more separate embodiments not expressly illustrated or described.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Thus, it is intended that the scope of the inventions herein disclosed should not be limited by the particular embodiments described above, but should be determined only by a fair reading of the claims that follow.

What is claimed is:

1. A pressure regulating adaptor for coupling with a closed vial, the adaptor comprising:

a base portion comprising a cap connector configured to secure the adaptor to a cap of the closed vial;

a first piercing member extending from the base portion, the first piercing member configured to be inserted through the cap of the vial and to provide a regulator channel in fluid communication with the environment outside the vial;

a second piercing member extending from the base portion, the second piercing member configured to be inserted through the cap of the vial and to provide an extractor channel for removal of fluid from the vial; and a bag secured to the adaptor, the bag configured to move between a stored position, in which the bag is housed at least partially within the first piercing member, and a deployed position, in which at least a portion of the bag expands within the vial as fluid is removed from the vial;

wherein the first piercing member and the second piercing member are positioned and shaped such that the piercing members puncture the cap of the vial in two distinct locations when the adaptor is coupled to the closed vial.

2. The pressure regulating adaptor of claim 1, wherein the first piercing member is longer than the second piercing member.

3. The pressure regulating adaptor of claim 1, further comprising a projection extending from the adaptor, the projection configured to provide a connection between the bag and the regulator channel.

4. The pressure regulating adaptor of claim 3, wherein a bag connector attaches the bag to the projection in substantially airtight engagement.

5. The pressure regulating adaptor of claim 4, wherein the bag connector comprises a chamber configured to accept a distal extension of the projection.

6. The pressure regulating adaptor of claim 1, wherein the first piercing member comprises a sleeve comprising a proximal base from which a plurality of sleeve members extend.

7. The pressure regulating adaptor of claim 6, wherein the plurality of sleeve members cooperate to form a cavity for housing the bag when the bag is in the stored position.

8. The pressure regulating adaptor of claim 6, wherein distal ends of the plurality of sleeve members opposite the proximal base are configured to form a tip of the first piercing member when the plurality of sleeve member are in a closed position.

9. The pressure regulating adaptor of claim 6, wherein the plurality of sleeve members are biased toward an open configuration, and wherein a jacket is used to retain the plurality of sleeve members in a closed configuration until the first piercing member is inserted through the cap of the vial.

10. The pressure regulating adaptor of claim 1, wherein the second piercing member is significantly smaller than the first piercing member.

11. The pressure regulating adaptor of claim 1, wherein the second piercing member is configured to extend just beyond a distal surface of the cap of the vial when the pressure regulating adaptor is coupled to the vial.

12. The pressure regulating adaptor of claim 1, wherein the cap connector comprises a skirt configured to encircle a portion of the closed vial.

13. The pressure regulating adaptor of claim 1, wherein the cap of the closed vial comprises a septum.

* * * * *

UNITED STATES PATENT AND TRADEMARK OFFICE

CERTIFICATE OF CORRECTION

PATENT NO. : 7,569,043 B2
APPLICATION NO. : 11/415969
DATED : August 4, 2009
INVENTOR(S) : Thomas F Fangrow It is certified that error appears in the above-identified patent and that said Letters Patent is hereby corrected as shown below:

On Page 2, Column 1 at line 36 change "11/416,622," to --11/415,622,--.

Signed and Sealed this

Sixth Day of April, 2010

David J. Kappos
*Director of the United States Patent and Trademark Office*